US010851402B2

(12) United States Patent
Baur et al.

(10) Patent No.: US 10,851,402 B2
(45) Date of Patent: Dec. 1, 2020

(54) METHOD FOR IN VITRO DETECTION AND MONITORING OF A DISEASE BY MEASURING DISEASE-ASSOCIATED PROTEASE ACTIVITY IN EXTRACELLULAR VESICLES

(71) Applicant: Friedrich-Alexander-Universitaet Erlangen-Nuernberg, Erlangen (DE)

(72) Inventors: Andreas Baur, Erlangen (DE); Kalle Saksela, Espoo (FI); Gerold Schuler, Spardorf (DE)

(73) Assignee: Friedrich-Alexander-Universitaet Erlangen-Nuernberg, Erlangen (DE)

( * ) Notice: Subject to any disclaimer, the term of this patent is extended or adjusted under 35 U.S.C. 154(b) by 0 days.

(21) Appl. No.: 14/760,054

(22) PCT Filed: Jan. 9, 2014

(86) PCT No.: PCT/EP2014/050335
§ 371 (c)(1),
(2) Date: Jul. 9, 2015

(87) PCT Pub. No.: WO2014/108480
PCT Pub. Date: Jul. 17, 2014

(65) Prior Publication Data
US 2015/0337356 A1    Nov. 26, 2015

(30) Foreign Application Priority Data

Jan. 9, 2013   (EP) ..................................... 13000071
Jan. 9, 2013   (EP) ..................................... 13000072

(51) Int. Cl.
C12Q 1/37       (2006.01)
G01N 33/574     (2006.01)
C07K 7/06       (2006.01)
G01N 33/542     (2006.01)
G01N 33/569     (2006.01)
G01N 33/68      (2006.01)

(52) U.S. Cl.
CPC .................. C12Q 1/37 (2013.01); C07K 7/06 (2013.01); G01N 33/542 (2013.01); G01N 33/56988 (2013.01); G01N 33/574 (2013.01); G01N 33/5743 (2013.01); G01N 33/6893 (2013.01); G01N 2333/96494 (2013.01)

(58) Field of Classification Search
CPC ...................................................... C12Q 1/37
USPC ......................................................... 435/5
See application file for complete search history.

(56) References Cited

U.S. PATENT DOCUMENTS

2003/0143651 A1   7/2003  Steward et al.
2010/0086956 A1   4/2010  Newman et al.
2010/0203529 A1*  8/2010  Kuslich ................ C12Q 1/6886
                                              435/6.12

FOREIGN PATENT DOCUMENTS

EP        2943585 B1    7/2018
WO    WO 2006/019379   2/2006
WO    WO 2007/059313   5/2007
WO    WO 2008/065540   6/2008
WO    WO 2014/108480   7/2014

OTHER PUBLICATIONS

Ginestra et al. (Anticancer Research. 1999; 19: 3439-3446).*
Myochin et al (J Am Chem Soc, 2012, 13730-13737).*
Lee et al (Chem Commun, 2008, 4250-4260).*
Bohm et al (Thrombosis Research, 2003, 111: 33-37).*
Kobayashi et al (Thrombosis Research, 2007, 119: 447-452).*
Futaki (Advanced Drug Delivery Reviews, 2005, 57: 547-558).*
Arduise et al., "Tetraspanins Regulate ADAM10-mediated Cleavage of TNF-alpha and Epidermal Growth Factor," J. Immunol., vol. 181, 7002-7013 (2008).
Atay et al., "Human Trophoblast-Derived Exosomal Fibronectin Induces Pro-Inflammatory IL-1beta Production by Macrophages," Am. J. Reprod. Immunol., vol. 66, 259-269 (2011).
Baur et al., "The N-terminus of Nef from HIV-1/SIV Associates with a Protein Complex Containing Lck and a Serine Kinase," Immunity, vol. 6, 283-291 (1997).
Blobel, C.P., "ADAMs: Key Components in EGFR Signalling and Development," Nat. Rev. Mol. Cell Biol., vol. 6, 32-43 (2005).
Caswell et al., "Integrins: Masters and Slaves of Endocytotic Transport," Nat. Rev. Mol. Cell Biol., vol. 10, 843-853 (2009).
de Hoog et al., "RNA and RNA Binding Proteins Participate in Early Stages of Cell Spreading Through Spreading Initiation Centers," Cell, vol. 117, 649-662 (2004).
Deacon et al., "Genomic Structure of an Attenuated Quasi Species of HIV-1 from a Blood Transfusion Donor and Recipients," Science, vol. 270, 988-991 (1995).
Deakin and Turner, "Paxillin Comes of Age," J. Cell Sci., vol. 121, 2435-2444 (2008).
Diaz-Rodriguez et al., "Extracellular Signal-Regulated Kinase Phosphorylates Tumor Necrosis Factor Alpha-Converting Enzyme at Threonine 735: A Potential Role in Regulated Shedding," Mol. Biol. Cell, vol. 13, 2031-2044 (2002).
Dong et al., Paxillin Nuclear-Cytoplasmic Localization is Regulated by Phosphorylation of the LD4 Motif: Evidence that Nuclear Paxillin Promotes Cell Proliferation, Biochem. J., vol. 418, 173-184 (2009).
Fernandez-Valle et al., "Paxillin Binds Schwannomin and Regulates its Density-dependent Localization and Effect on Cell Morphology," Nat. Genet., vol. 31, 354-362 (2002).

(Continued)

Primary Examiner — Sean E Aeder
(74) Attorney, Agent, or Firm — Jenkins, Wilson, Taylor & Hunt, P.A.

(57) ABSTRACT

The present invention relates to a method for in vitro detection and/or monitoring of a disease in a sample, based on measurement of enzymatic activity of proteases activated and secreted upon disease development, to modified peptides used for the enzymatic detection of the proteases, the use of the peptides, a kit comprising such peptides and the use of ADAM-protease activity as a surrogate marker for disease burden and activity in infectious, inflammatory, and malignant diseases, such as HIV infection and melanoma.

2 Claims, 39 Drawing Sheets
Specification includes a Sequence Listing.

(56) References Cited

OTHER PUBLICATIONS

Glushakova et al., "Nef Enhances Human Immunodeficiency Virus Replication and Repsonsiveness to Interleukin-2 in Human Lymphoid Tissue Ex Vivo," J. Virol., vol. 73, 3968-3974 (1999).
Graziosi et al., "Kinetics of Cytokine Expression During Primary Human Immunodeficiency Virus Type 1 Infection," Proc. Natl. Acad. Sci. U.S.A., vol. 93, 4386-4391 (1996).
Higginbotham et al., "Amphiregulin Exosomes Increase Cancer Cell Invasion," Curr. Biol., vol. 21, 779-786 (2011).
Ishibe et al., "Paxillin Serves as an ERK-regulated Scaffold for Coordinating FAK and Rac Activation in Epithelial Morphogenesis," Mol. Cell, vol. 16, 257-267 (2004).
Jacob et al., "Dual Function of Polycomb Group Proteins in Differentiated Murine T helper (CD4+) Cells," J. Mol. Signal., vol. 6, 5 (2011).
Kestler et al., "Improtance of the Nef Gene for Maintenance of High Virus Loads and for Development of AIDS," Cell, vol. 65, 651-662 (1991).
Kissil et al., "Merlin, the Product of the Nf2 Tumor Suppressor Gene, is an Inhibitor of the p21-activated Kinase, Pak1," Mol. Cell, vol. 12, 841-849 (2003).
Koumangoye et al., "Detachment of Breast Tumor Cells Induces Rapid Secretion of Exosomes which Subsequently Mediate Cellular Adhesion and Spreading," PLoS. One 6, e24234 (2011).
Le Gall et al., "ADAMs 10 and 17 Represent Differentially Regulated Somponents of a General Shedding Machinery for Membrane Proteins Such as Transforming Growth Factor Alpha, L-selectin, and Tumor Necrosis Factor Alpha," Mol. Biol. Cell, vol. 20, 1785-1794 (2009).
Lee et al., "HIV Hef, Paxillin, and Pak1/2 Regulate Activation and Secretion of TACE/ADAM10 Proteases," Molecular Cell, vol. 49, No. 4, 668-679 (2013).
Lenassi et al., "HIV Nef is Secreted in Exosomes and Triggers Apoptosis in Bystander CD4+ T cells," Traffic, vol. 11, 110-122 (2010).
Manninen et al., "SH3-Domain Binding Function of HIV-1 Nef is Required for Association with a PAK-related Kinase," Virology, vol. 250, 273-282 (1998).
Moss et al., "Drug Insight: Tumor Necrosis Factor-Converting Enzyme as a Pharmaceutical Target for Rheumatoid Arthritis," Nat. Clin. Pract. Rheumatol., vol. 4, 300-309 (2008).
Muratori et al., "Massive Secretion by T Cells is Caused by HIV Nef in Infected Cells and by Nef Transfer to Bystander Cells," Cell Host. Microbe, vol. 6, 218-230 (2009).
Murphy, G., "The ADAMs: Signalling Scissors in the Tumour Microenvironment," Nat. Rev. Cancer, vol. 8, 929-941 (2008).
Nayal et al., "Paxillin Phosphorylation at Ser273 Localizes a GIT1-PIX-PAK Complex and Regulates Adhesion and Protrusion Dynamics," J. Cell Biol., vol. 173, 587-589 (2006).
Notification of Transmittal of the International Search Report and the Written Opinion of the International Searching Authority, or the Declaration, corresponding to PCT/EP2014/050335, dated Mar. 24, 2014.
Ostergaard et al., "Paxillin Phosphorylation and Association with Lck and Pyk2 in anti-CD3- or anti-CD45-stimulated T cells," J. Biol. Chem., vol. 273, 5692-5696 (1998).
Philipp et al., "The Polycomb Group Protein EED Couples TNF Receptor 1 to Neutral Sphingomyelinase," Proc. Natl. Acad. Sci. U.S.A., vol. 107, 1112-1117 (2010).
Qazi et al., "Proinflammatory Exosomes in Bronchoalveolar Lavage Fluid of Patients with Sarcoidosis," Thorax, vol. 65, 1016-1024 (2010).
Raymond et al., "HIV Type 1 Nef is Released from Infected Cells in CD45(+) Microvesicles and is Present in the Plasma of HIV-Infected Individuals," AIDS Res. Hum. Retroviruses, vol. 27, 167-178 (2011, published online Oct. 21, 2010).
Renkema et al., Human Immunodeficiency Virus Type 1 Nef Selectively Associates with a Catalytically Active Subpopulations of p21-Activated Kinase 2 (PAK2) Independently of PAK2 Bindig to Nck or Beta-PIX, J. Virol., vol. 75, 2154-2160 (2001).
Renkema et al., "Identification of the Nef-Associated Kinase as p21-Activated Kinase 2," Curr. Biol., vol. 9, 1407-1410 (1999).
Rietzler et al., "The Human WD Repeat Protein WAIT-1 Specifically Interacts with the Cytoplasmic Tails of Beta7-Integrins," J. Biol. Chem., vol. 273, 27459-27466 (1998).
Sawai et al., "Human Immunodeficiency Virus Type 1 Nef Associates with a Cellular Serine Kinase in T Lymphocytes," Proc. Natl. Acad. Sci. U.S.A., vol. 91, 1539-1543 (1994).
Schiavoni et al., "HIV-1 Nef Enhances Both Membrane Expression and Virion Incorporation of Env Products. A Model for the Nef-dependent Increase of HIV-1 Infectivty," J. Biol. Chem., vol. 279, 22996-23006 (2004).
Skog et al., "Glioblastoma Microvesicles Transport RNA and Proteins that Promote Tumour Growth and Provide Diagnostic Biomarkers," Nat. Cell Biol., vol. 10, 1470-1476 (2008).
Solomon et al., "The Fate of Pro-TNF-alpha Following Inhibition of Metalloprotease-Dependent Processing to Soluble TNF-alpha in Human Monocytes," J. Immunol., vol. 159, 4524-4531 (1997).
Stoeck et al., "A Role for Exosomes in the Constitutive and Stimulus-Induced Ectodomain Cleavage of L1 and CD44," Biochemical Journal, vol. 393, No. 3, 609-618 (2006).
Thery et al., "Isolation and Characterization of Exosomes from Cell Culture Supernatants and Biological Fluids," Curr. Protoc. Cell Biol., Chapter 3, Unit. (2006).
Tian et al., "Visualizing of the Cellular Uptake and Intracellular Trafficking of Exosomes by Live-Cell Microscopy," J. Cell Biochem., vol. 111, 488-496 (2010).
Trajkovic et al., "Ceramide Triggers Budding of Exosome Vesicles into Multivesicular Endosomes," Science, vol. 319, 1244-1247 (2008).
Tumbarello et al., "The Paxillin LD Motifs," FEBS Lett., vol. 513, 114-118 (2002).
Turner et al., "Paxillin LD4 Motif Binds PAK and PIX Through a Novel 95-kD Ankyrin Repeat, ARF-GAP Protein: A Role in Cytoskeletal Remodeling," J. Cell Biol., vol. 145, 851-863 (1999).
Turner, C.E. "Paxillin and Focal Adhesion Signalling," Nat. Cell Biol., vol. 2, E231-E236 (2000).
Van den Broeke et al., "An Emerging Role for p21-activated Kinases (Paks) in Viral Infections," Trends Cell Biol., vol. 20, 160-169 (2010).
Wei et al., "Activation of p21-activated Kinase 2 by Human Immunodeficiency Virus Type 1 Nef Induces Merlin Phosphorylation," J. Virol., vol. 79, 14976-14980 (2005).
Witte et al., "HIV-1 Nef Mimics an Integrin Receptor Signal that Recruits the Polycomb Group Protein Eed to the Plasma Membrane," Mol. Cell, vol. 13, 179-190 (2004).
Wolf et al., "HIV Nef Enhances Tat-mediated Viral Transcription Through a hnRNP-K-nucleated Signaling Complex," Cell Host. Microbe, vol. 4, 398-408 (2008).
Wolf et al., "HIV-1 Nef Associated PAK and PI3-Kinases Stimulate Akt-Independent Bad-Phosphorylation to Induce Anti-Apoptotic Signals," Nat. Med., vol. 7, 1217-1224 (2001).
Wolf et al., "Novel (n)PKC Kinases Phosphorylate Nef for Increased HIV Transcription, Replication, and Perinuclear Targeting," Virology, vol. 370, 45-54 (2008).
Wu and Marsh, "Selective Transcription and Modulation of Resting T Cell Activity by PreintegratedHIV DNA," Science, vol. 293, 1503-1506 (2001).
Zangerle et al., "Increased Serum Concentrations of Soluble Tumor Necrosis Factor Receptors in HIV-Infected Individuals are Associated with Immune Activation," J. Acquir. Immune. Defic., Syndr., vol. 7, 79-85 (1994).
International Preliminary Report on Patentability corresponding to International Application No. PCT/EP2014/050335 dated Jul. 14, 2015.
Baur, A.S., "HIV-Nef and AIDS Pathogenesis: Are We Barking Up the Wrong Tree?" Trends Microbiol., vol. 19, 435-440 (2011).
Cocucci et al., "Shedding microvesicles: artefacts no more," Review Cell Press, Trends in Cell Biology, vol. 19, No. 2, pp. 43-51 (2009).

(56) References Cited

OTHER PUBLICATIONS

Jin et al., "A continuous Fluorimetric Assay for Tumor Necrosis Factor-αConverting Enzyme," Analytical Biochemistry, 302, pp. 269-275 (2002).
Moss et al., "Fluorescent substrates for the proteinases ADAM17, ADAM10, ADAM8, and ADAM12 useful for high-throughput inhibitor screening," Analytical Biochemistry, 366, pp. 144-148 (2007).
Neumann et al., "Characterization of Mca-Lys-Pro-Leu-Gly-Leu-DPa-Ala-Arg-NH2, a flurogenic substrate with increased specificity constants for collagenases and tumor necrosis factor converting enzyme," Analytical Biochemistry, 328, pp. 166-173 (2004).
Valadi et al., "Exosome-mediated transfer of mRNAs and microRNAs is a novel mechanism of genetic exchange between cells," Nat Cell Biol., 9(6), pp. 654-659 (Jun. 2007).
Lee et al., "HIV-Nef and ADAM17-Containing Plasma Extracellular Vesicles Induce and Correlate with Immune Pathogenesis in Chronic HIV Infection," EBioMedicine, vol. 6, pp. 103-113 (2016).
Communication pursuant to Article 94(3) EPC corresponding to European Patent Application No. 14700197.8 dated Jan. 16, 2017.
Ostalecki et al., "HIV Nef- and Notch1-dependent Endocytosis of ADAM17 Induces Vesicular TNF Secretion in Chronic HIV Infection," EBioMedicine, pp. 1-11 (2016).
Communication pursuant to Article 71(3) EPC corresponding to European Patent Application No. 14700197.8 dated Jan. 29, 2018.
Cvjetkovic et al., "Detailed Analysis of Protein Topology of Extraclualar Vesicles—Evidence of Unconventional Membrane Protein Orientation," Scientific Reports, vol. 6, No. 36338, pp. 1-12 (2016).
Office Action corresponding to Canadian Patent Application No. 2897304 dated Oct. 23, 2019.

* cited by examiner

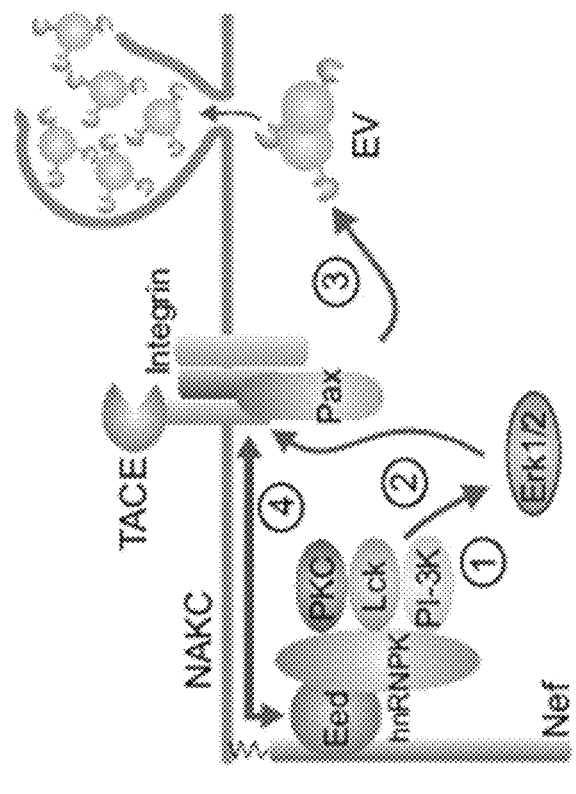
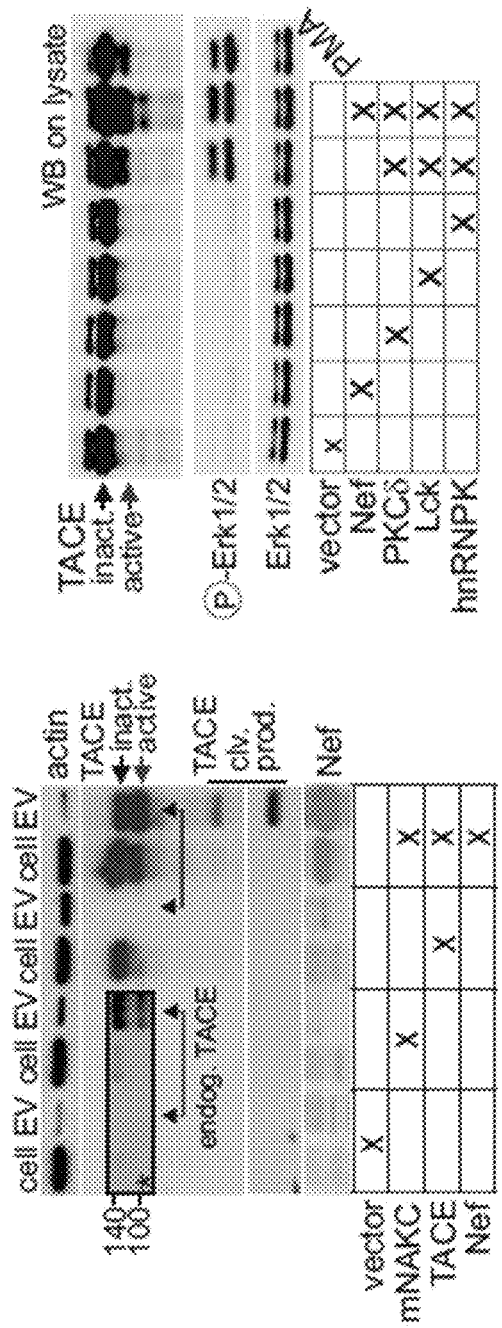
FIG. 1A
FIG. 1B
FIG. 1C

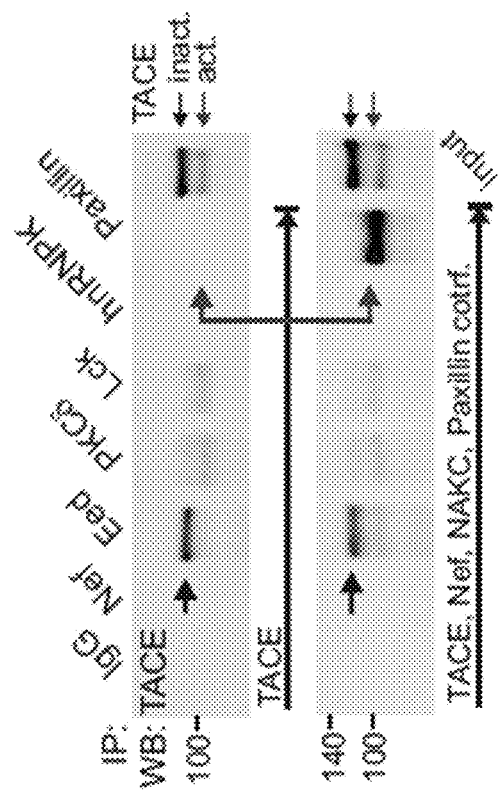
FIG. 1D
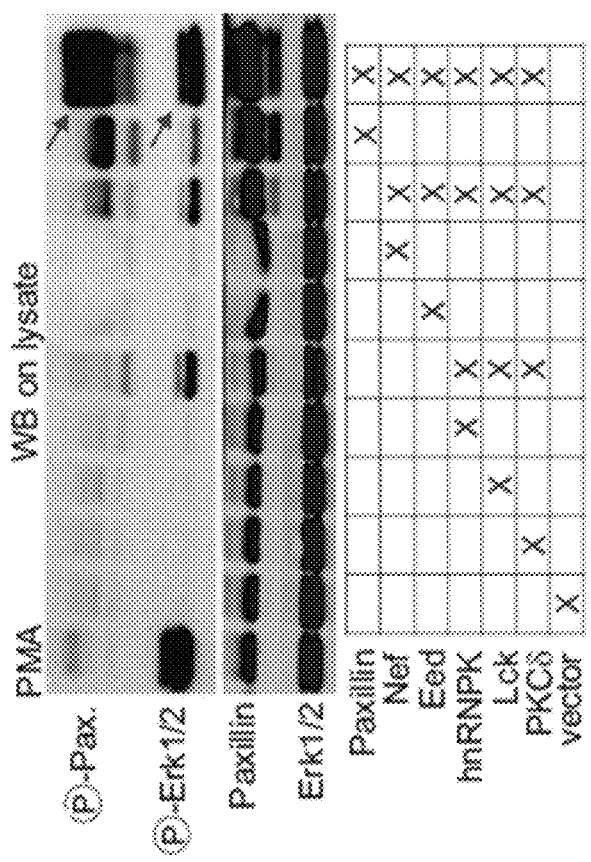
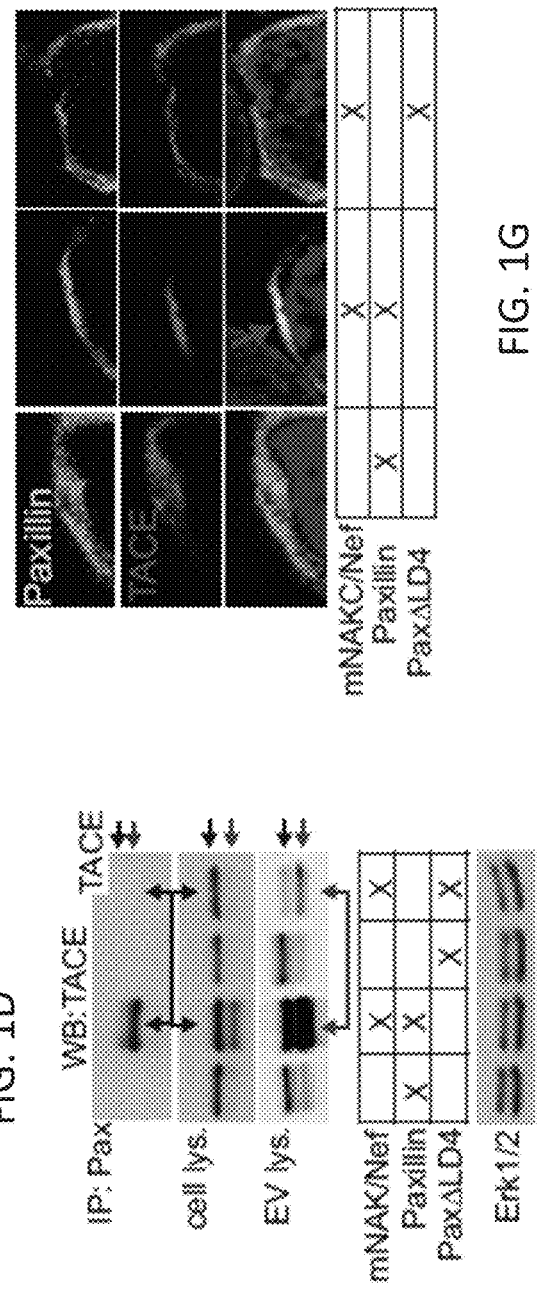
FIG. 1E
FIG. 1G
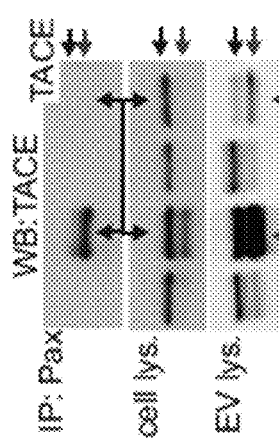
FIG. 1F

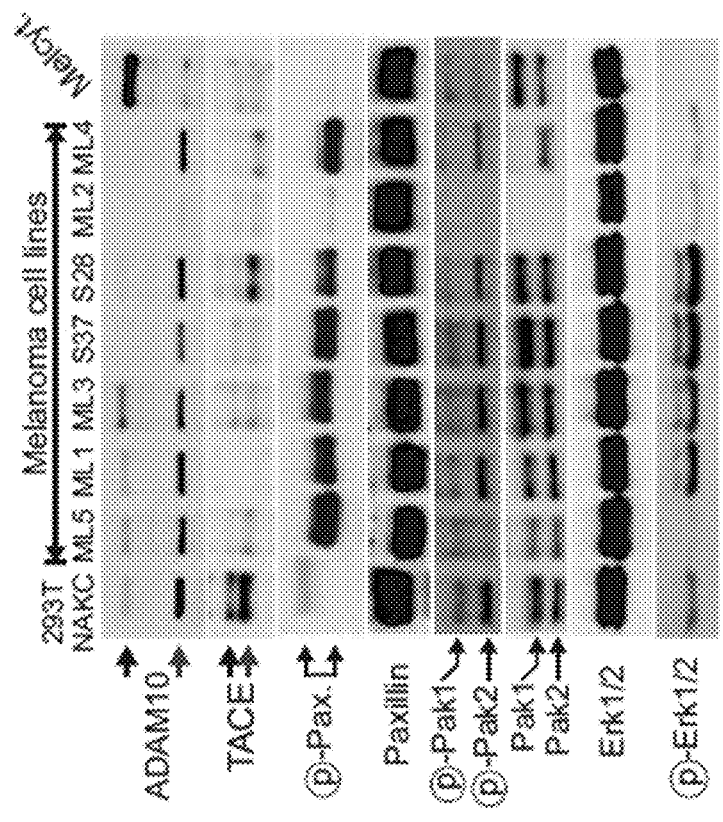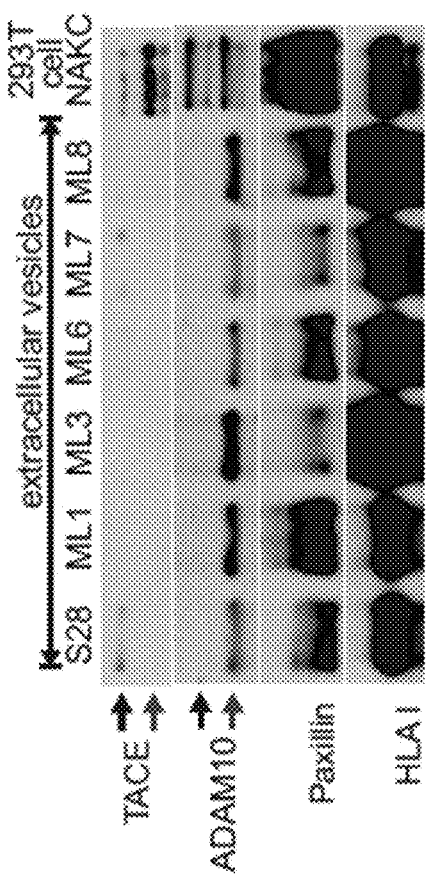
FIG. 4A
FIG. 4B

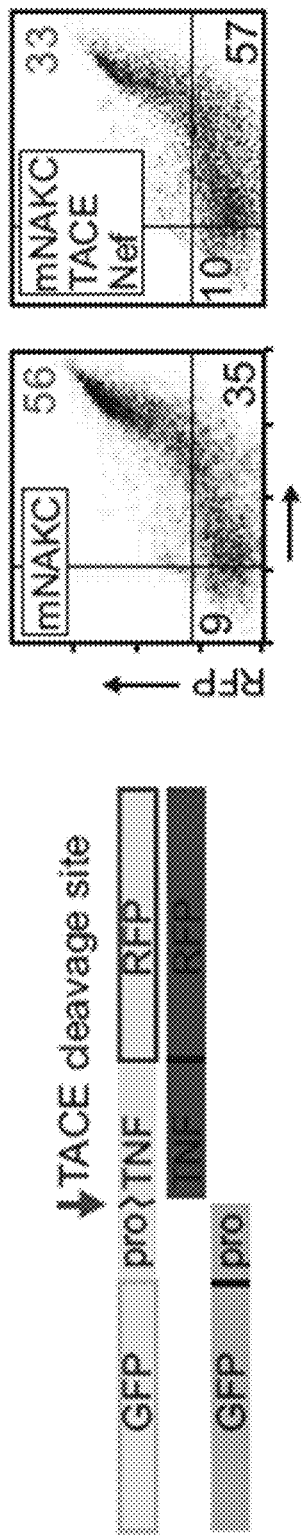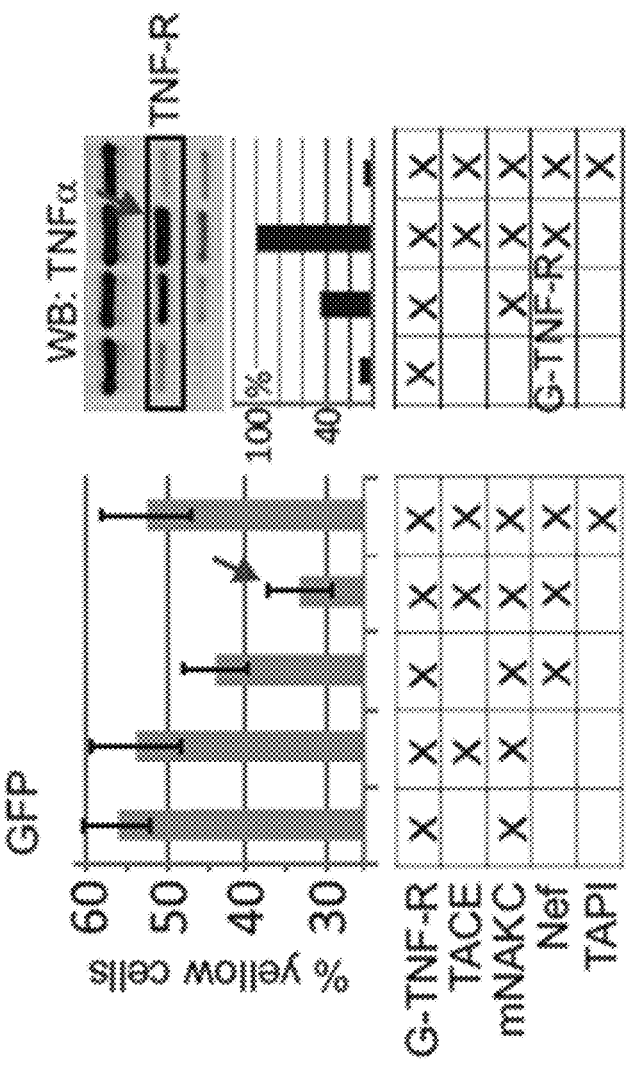
FIG. 5A
FIG. 5B
FIG. 5C
FIG. 5D

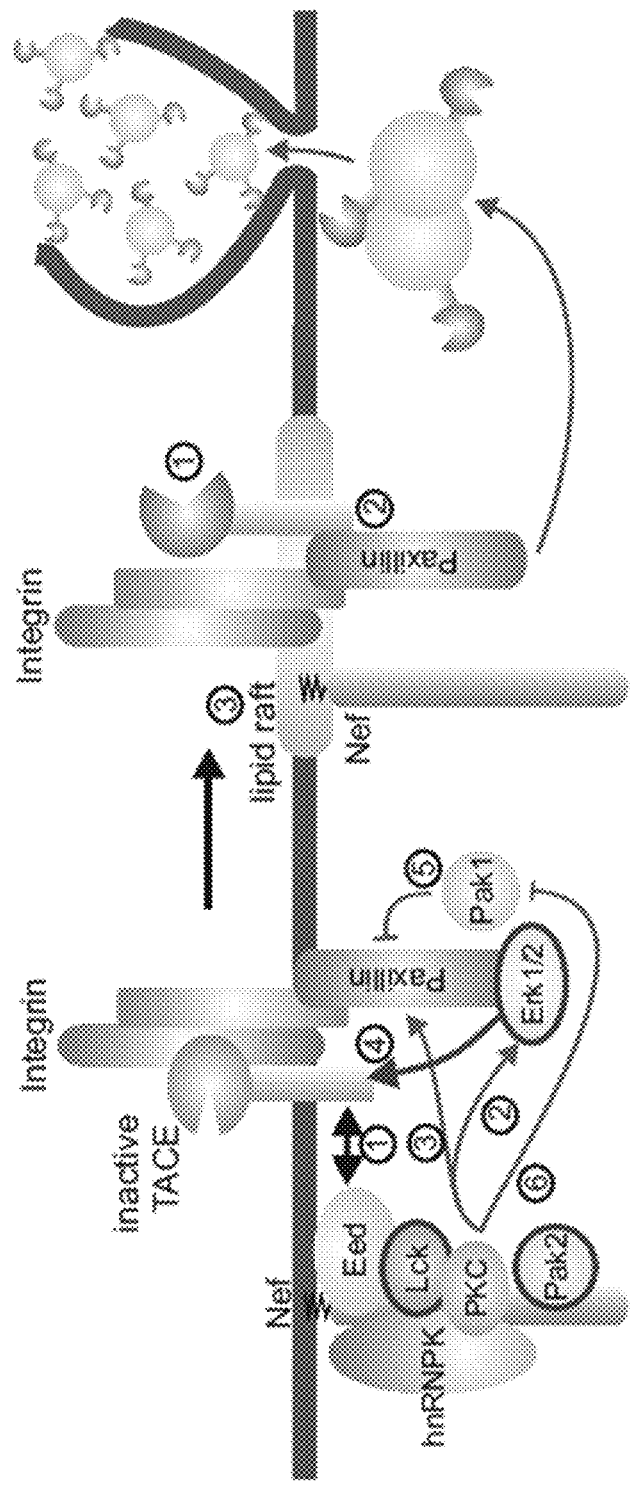

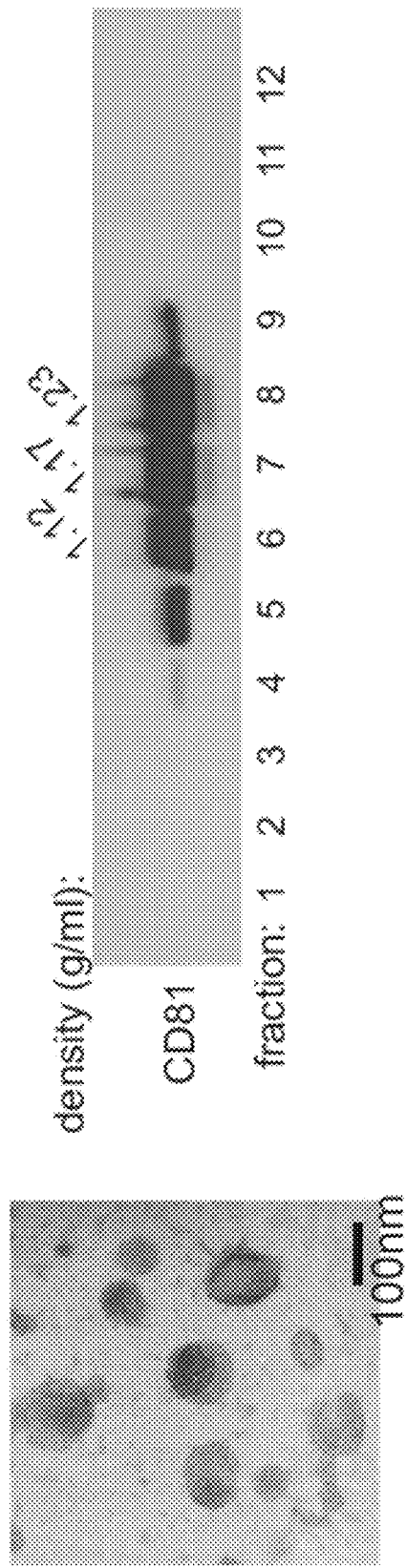
FIG. 15E
FIG. 15D
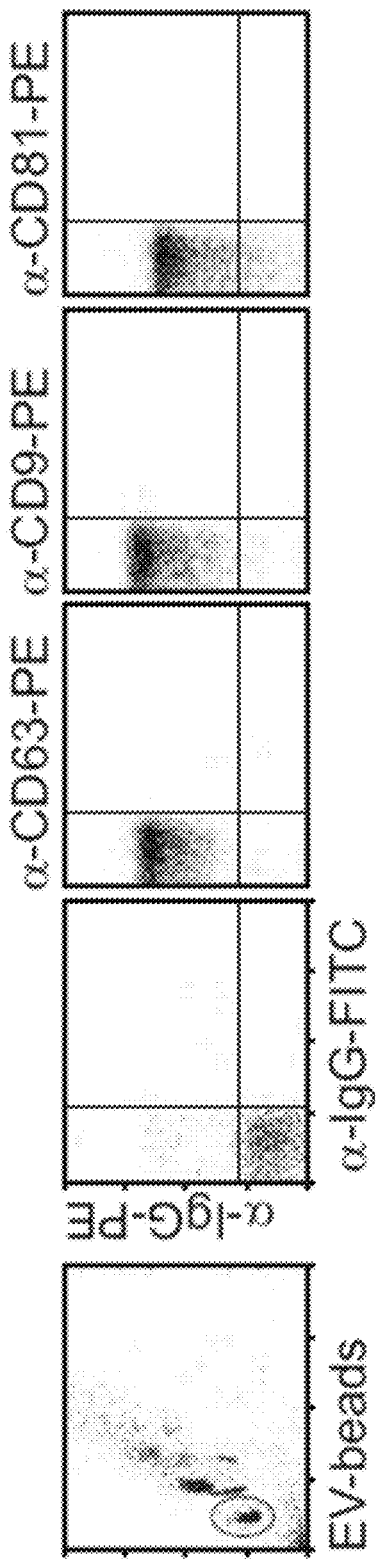
FIG. 15F

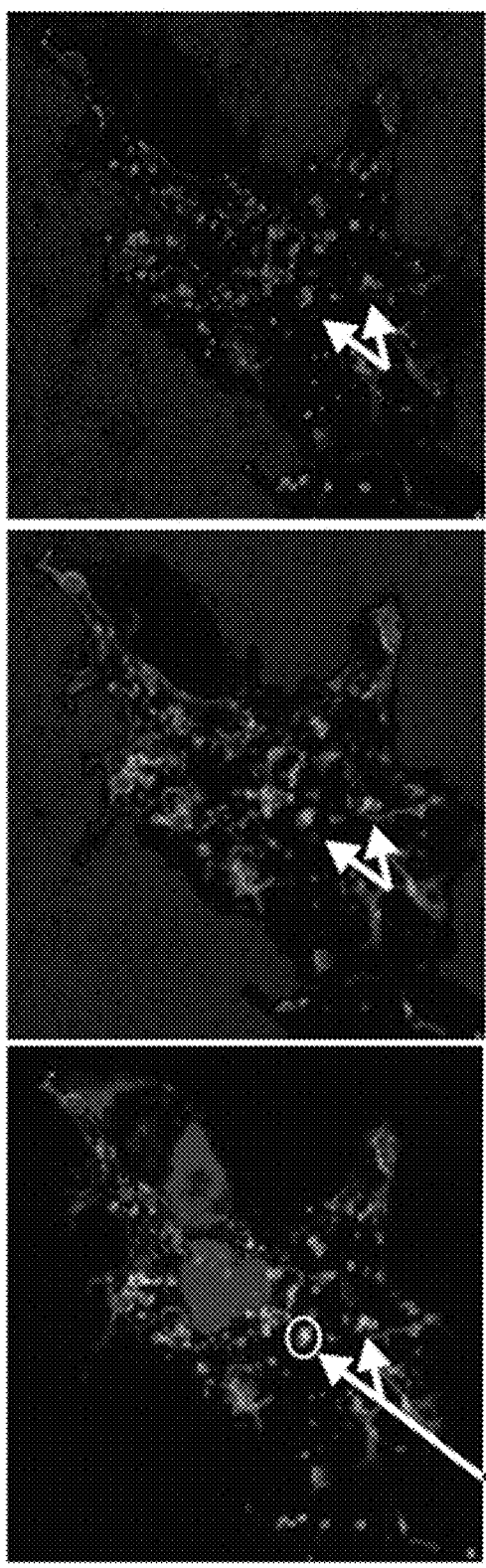
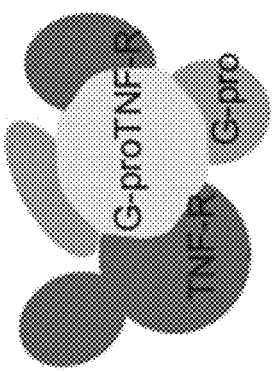
FIG. 21

SEQUENCE LISTING

<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Protease specific peptide

<400> SEQUENCE: 1

Arg Ser Ser Ser Arg Val Ala Gln Ala Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Protease specific peptide

<400> SEQUENCE: 2

Lys Ser Lys Gln Ala Met Gln Asp Gly His
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Protease specific peptide

<400> SEQUENCE: 3

Arg Ala Leu Gly Leu Pro Lys
1               5

<210> SEQ ID NO 4
<211> LENGTH: 16
<212> TYPE: PRT
<213> ORGANISM: Artificial Sequence
<220> FEATURE:
<223> OTHER INFORMATION: Protease specific peptide

<400> SEQUENCE: 4

Lys Lys Trp Lys Met Arg Arg Asn Gln Phe Trp Ile Lys Ile Gln Arg
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Membrane penetrating amino acids

<400> SEQUENCE: 5

Gly Arg Lys Lys Arg Arg Gln Arg Arg Pro Pro Gln
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Membrane penetrating amino acids

<400> SEQUENCE: 6

Arg Arg Arg Arg Arg Arg Arg Arg
1               5

```
<210> SEQ ID NO 7
<211> LENGTH: 9
<212> TYPE: PRT
<213> ORGANISM: Artificial Sequence
<220> FEATURE:
<223> OTHER INFORMATION: Membrane penetrating amino acids

<400> SEQUENCE: 7

Arg Arg Arg Arg Arg Arg Arg Arg Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Membrane penetrating amino acids

<400> SEQUENCE: 8

Arg Arg Arg Arg Arg Arg Arg Arg Arg Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Membrane penetrating amino acids

<400> SEQUENCE: 9

Arg Arg Arg Arg Arg Arg Arg Arg Arg Arg Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Membrane penetrating amino acids

<400> SEQUENCE: 10

Arg Arg Arg Arg Arg Arg Arg Arg Arg Arg Arg Arg
1               5                   10

<210> SEQ ID NO 11
<211> LENGTH: 15
<212> TYPE: PRT
<213> ORGANISM: Artificial Sequence
<220> FEATURE:
<223> OTHER INFORMATION: C-terminus of ADAM17

<400> SEQUENCE: 11

Lys Leu Gln Arg Gln Asn Arg Val Asp Ser Lys Glu Thr Glu Cys
1               5                   10                  15
```

METHOD FOR IN VITRO DETECTION AND MONITORING OF A DISEASE BY MEASURING DISEASE-ASSOCIATED PROTEASE ACTIVITY IN EXTRACELLULAR VESICLES

CROSS-REFERENCE TO RELATED APPLICATIONS

This application is a national stage application of PCT International Patent Application No. PCT/EP2014/1050335, filed on Jan. 9, 2014, which claims priority to European Patent Application No. 13000071.4, filed on Jan. 9, 2013 and European Patent Application No. 13000072.2 filed on Jan. 9, 2013.

TECHNICAL FIELD

The present invention relates to a method for in vitro detection and/or monitoring of a disease in a sample, based on measurement of enzymatic activity of proteases activated and secreted upon disease development, to modified peptides used for the enzymatic detection of the proteases, the use of the peptides, a kit comprising such peptides and the use of ADAM-protease activity as a surrogate marker for disease burden and activity in infectious, inflammatory, and malignant diseases, such as HIV infection and melanoma.

BACKGROUND ART

For efficient replication in infected hosts, HIV and SIV require the accessory Nef protein which is expressed early in the viral life cycle and targeted to the plasma membrane (Kestler, III et al., 1991; Deacon et al., 1995). However, the molecular function of Nef has not been satisfyingly explained yet. In their previous work the inventors have demonstrated that Nef assembles a peculiar set of kinases and adaptor proteins (NAKC for Nef-associated kinase complex or Nef signaling complex, see FIG. 15A) that stimulate viral replication by transcriptional derepression. Important steps in this mechanism were the cytoplasmic recruitment of the transcriptional repressor Eed and the subsequent association and activation of hnRNPK, Lck, PKC, PI3K and Erk1/2 (Baur et al., 1997; Wolf et al., 2001; Witte et al., 2004; Wolf et al., 2008). Since Eed, hnRNPK and Lck are also recruited by activated integrins we assumed that Nef mimicked an integrin receptor signal (Witte et al., 2004; de Hoog et al., 2004; Rietzler et al., 1998).

While the cytoplasmic recruitment of Eed seemed a logical step in transcriptional derepression, the precise role of the whole Nef-assembled complex remained obscure. Recently Eed's cytoplasmic role was further analyzed, demonstrating its involvement in T cell activation and coupling of the TNFR1 to neutral sphingomyelinase (nSMase2) (Philipp et al., 2010). In this context Eed bound nSMase2 and mediated its activation after TNFR1/TNFα stimulation. One of the functions of nSMase2 is the generation of ceramide which stimulates the formation of vesicles that are bound for secretion (Trajkovic et al., 2008).

The inventors and others have previously demonstrated that HIV Nef induces the secretion of extracellular vesicles (EV) in vitro and in vivo (Muratori et al., 2009; Lenassi et al., 2010; Raymond et al., 2010). A remarkably similar phenomenon was reported for cancer cells in vitro and in patients (Skog et al., 2008). While the molecular function of tumor-derived EV is still explored, several reports demonstrated the presence of ADAM (a disintegrin and metalloprotease) proteases therein (Higginbotham et al., 2011; Stoeck et al., 2006). Since integrins associate with ADAM proteases (Murphy, 2008) and also induce the formation of vesicles (Caswell et al., 2009), these findings suggested a potential link between integrins, Nef-induced EV and ADAM proteases.

ADAM proteases are key factors in innate immunity, cancer and cell development. They cleave numerous cytokines, receptors and ligands (Murphy, 2008; Blobel, 2005) and are a prime target for drug intervention (Moss et al., 2008). Among the most analyzed family members are TNFα converting enzyme (TACE/ADAM17) and its close relative ADAM10, which cleave proTNFα among many other substrates (Arduise et al., 2008; Le Gall et al., 2009). Mechanisms that activate TACE are not understood in detail, but phosphorylation by Erk1/2 (Diaz-Rodriguez et al., 2002) and cleavage of an inhibitory pro-domain (Blobel, 2005) are crucial steps.

ADAM proteases are a subfamily of Matrix metalloproteinases (MMPs). MMPs belong to a larger family of proteases known as the metzincin superfamily.

Many cells, in particular when activated, secrete 40-120 nm sized extracellular vesicles (hereafter referred as EV) that contain mRNA, miRNA, and proteins, including active enzymes. EVs are found in all body fluids at rather high concentrations ($>10^7$/ml) and are considered an important source of molecules for diagnostic procedures and assays.

While vesicles shed by living cells have been detected several decades ago, it was only recently (Valadi H, Ekström K, et al. Nat Cell Biol. 2007 June; 9(6):654-9; Skog J, Würdinger T, et al. Nat Cell Biol. 2008 December; 10(12): 1470-6).) that they were rediscovered as a valuable source of biomarkers (proteins, mRNAs, miRNAs). At present the field is trying to extract disease-relevant information especially from the miRNA content of EVs using array technology or real-time PCR.

Before 2010 vesicles shed by living cells were predominantly termed "exosomes" based on the definition that they are derived from multivesicular bodies (MVB). The scientific field defined these vesicles by the following criteria (see Thery et al. 2006, Isolation and characterization of exosomes from cell culture supernatants and biological fluids. Curr. Protoc. Cell Biol. Chapter 3, Unit.):

1) Accumulation and release by multivesicular bodies (MVB). MVB are intracellular compartments that are found in almost any cell. When cells are in a resting stage, these compartments are usually empty. However, they "fill up" quickly with small vesicles once the cell is active or activated. Vesicle-filled MVB can move to—and fuse with the outer plasma membrane and release their content, namely the vesicles, into the extracellular space. These vesicles are then called exosomes. Vesicles released by other means were not considered to be exosomes. For example, Vesicles budding directly from the plasma membrane were termed "microvesicles" (Cocucci et al., 2009).

2) Exosomes have certain defining surface markers including: CD63, CD9, CD81 and HLA class I.

3) Exosome surface markers have the same orientation as in the plasma membrane of the shedding cell, meaning their extracellular domain is facing towards the extravesicular space.

In 2011 the newly established International Society for Extracellular Vesicles (ISEV) conceded that the term "exosome" cannot be applied to all forms of vesicles shed by living cells since differences in surface markers and release modes were apparent and described. Hence the term "extracellular vesicle" (EV) became the internationally accepted description of all vesicular structures that are released by living cells. The term "extracellular vesicle" (EV) as used in this patent application describes all vesicles that are released by a living cell (in contrast to a dying or apoptotic cell), there is no restriction or exclusion criteria based on size (in nanometer), markers (e.g. surface marker) or release mechanism (e.g. MVB-derived).

The term EVP, as used in this patent application, describes a subgroup of EV that contain an enzymatically active protease (e.g. matrix metalloprotease). EVP may be released by any cellular release mechanism. However, the present inventors previously found that EVPs are preferably released by a mechanism that differs from exosomes-like (derived from MVB) or microvesicle-like (derived from the plasma membrane) mechanism, more preferably the EVP are released by a distinct mechanism described and demonstrated in detail in Muratori et al. Cell Host Microbe. 2009; 6(3):218-30). Muratori et al. could show that, for example, the HIV-Nef-induced EVP-release mechanism resembled a budding-like process, which occurred very often at the site of microvilli formation and protrusions. First, small vesicles were seemingly transported from the cytoplasm to the plasma membrane (PM) and bulged the PM into a ball-like structure. Then the PM apparently ruptured and released the EVP eventually leaving an empty membrane compartment behind. Surprisingly, the released EVP remained coherent in clusters and attached in whole complexes to cell surfaces of bystander cells (FIG. 8). Thus, that the Nef-induced generation of EVP differed from previously described mechanism.

The activity of proteases like ADAM (A Disintegrin And Metalloproteinase, a subfamily of matrix metalloproteases) can be measured in vitro by providing a suitable peptide substrate in appropriate buffer conditions (Jin et al. Analytical Biochemistry, 2002; 302, 269-275; Neumann et al., Analytical Biochemistry, 2004; 328, 166-173). A known specific peptide substrate for ADAM17 has the following amino acid sequence: RSSSRVAQAL (SEQ ID 1).

Based on this sequence, the use of FRET peptides to assay ADAM activity is a common standard and commercial assay systems are available, for example by the company AnaSpec in Belgium.

A highly specific peptide substrate for ADAM10 has the following sequence: KSKQAMQDGH (SEQ ID 2) (Moss and Rasmussen, Analytical Biochemistry, 2007; 366, 144-148).

The peptide RALGLPK (SEQ ID 3) revealed to be a broad substrate for collagenases and ADAM proteases (Neumann et al., 2004).

Stoeck et al. (Biochem J. 2006; 393: 609-618) have previously described ADAM-containing vesicles and suggested that tumor cells shed these vesicles in a manner in which the active/catalytic center of the protease is located on the surface of the vesicle facing the extravesicular space (FIG. 9).

There are countless diseases known that affect living beings. A disease is any abnormal condition that affects the body of an organism and broadly refers to any condition that impairs normal function, and is therefore associated with dysfunction of normal homeostasis. The disease can be a infectious diseases, which are clinically evident diseases that result from the presence of pathogenic microbial agents, including viruses, bacteria, fungi, protozoa, multicellular organisms, and aberrant proteins known as prions. The disease can be a non-infectious disease, including most forms of cancer, heart disease, and genetic disease.

Viral infections are usually diagnosed by clinical signs (e.g. fever, rash) and, in general, 10-14 days later by the development of, usually, IgM antibodies, and later IgG antibodies, both of which are detected by various in vitro assays. Alternatively, infections may be detected by polymerase chain reaction (PCR) detecting nucleic acids of the invading virus. In either case the clinician has to have an idea which virus may have caused the infection. However, in clinical situations this is often unknown and/or poses a diagnostic challenge. Thus, assuming a bacterial infection, patients are very often treated with antibiotics. There is no general test available indicating a viral infection.

The human immunodeficiency virus (HIV) is a lentivirus (slowly replicating retrovirus) that causes the acquired immunodeficiency syndrome (AIDS), a condition in humans in which progressive failure of the immune system allows life-threatening opportunistic infections and cancers to thrive.

Despite the enormous success of current HIV treatment by Highly Active Anti-Retroviral Therapy (HAART), the immune system of most HIV-infected individuals does not fully recover, and resistance to individual treatment regimens develops frequently. Furthermore, cessation of treatment leads to a rapid reactivation of viral replication, implying that an important viral reservoir cannot be cleared by HAART. The location of the viral reservoir and the reasons for persistent immune deficiency (lower CD4 counts) are unknown. There is currently no assay or test to assess the activity or size of this viral reservoir. Replication activity is measured by assessing the number of viral RNA genomes (copy numbers) in circulating blood/plasma, but HAART treated individuals usually have low to undetectable viral copy numbers.

Cancer is usually discovered by x-ray- or NMR-based imaging technologies as soon as it appears in a sizable/visible mass (at least >6 mm). Before tumors reach that size and after surgical removal of a primary tumor, residual tumor activity cannot be assessed. Thus there is a great need for sensitive biomarkers to detect a growing or relapsing tumor mass. In melanoma, for example, there are currently two tumor markers used, S100 and MIA (melanoma inhibitory factor). Both factors, however, may be negative despite sizable tumor masses, and conversely, both or one factor may be positive despite the lack of an assessable tumor mass.

In clinical terms inflammation is characterized by a painful reddish swelling of a body part or organ, e.g. skin area or limb. In immunological terms it is characterized by the accumulation of activated immune cells of different kind (e.g. CD4 and CD8 T cells, NK cells, dendritic cells and macrophages) that interact with each other and release rather large kind of so-called pro-inflammatory cytokines and chemokines, as for example TNFalpha (the precursor of which, pro-TNF alpha, is cleaved by Adam17). The activity of these cytokines/chemokines cause clinical effects as described above.

In summary there are currently no biomarkers available that would reflect the activity of residual cancer cells either after primary surgery, or before a tumor mass can be detected by conventional imaging techniques. Likewise there is no biomarker available that would reflect the activity of the latent reservoir in HIV—or any other viral infection. In both cases such (a) biomarker(s) would be of paramount importance for detection and treatment purposes. The inherent problem of a small amount of cancer cells or barely replicating latent viruses is the very low level of shedded antigen found in the periphery. Current test systems are simply not sensitive enough to detect these low levels of proteins/antigens. Conventional amplification systems, like quantitative PCR, are restricted to nucleic acids and have not been developed for cancer yet, or do not adequately mirror the latent reservoir of HIV.

DISCLOSURE OF THE INVENTION

Technical Problem

Thus, it is an object of the present invention to provide a simple method with high sensitivity for the in vitro detection and monitoring of a disease in a sample provided from a patient.

Technical Solution

In order to achieve the object, a method for in vitro detection and/or monitoring of a disease in a sample comprises the following steps: providing a sample from a patient, and measuring enzymatic activity of at least one disease-associated protease in extracellular vesicles in the sample.

In a preferred aspect of the present invention the protease-containing extracellular vesicles are enriched and/or purified within the sample prior to measuring enzymatic activity.

In a further preferred aspect of the present invention the enzymatic activity of the disease-associated protease is measured using a specific peptide that serves as a substrate for the disease-associated protease.

In a further preferred aspect of the present invention the specific peptide is modified with chemical groups that enable to detect the proteolytic cleavage of the specific peptide based on Forster resonance energy transfer (FRET).

In a further preferred aspect of the present invention the specific peptide comprises chemical and/or amino acid modifications for translocation of the peptide into the EV.

In a further preferred aspect of the present invention the specific peptide is a FRET peptide comprising lipophilic fluorochrome and quencher moieties conferring membrane translocation potential to the substrate peptide.

In a further preferred aspect of the present invention the specific peptide comprises a sequence selected from the group consisting of a sequence having at least 50% sequence identity to SEQ ID NO: 1, a sequence having at least 50% sequence identity to SEQ ID NO: 2, and/or a sequence having at least 50% sequence identity to SEQ ID NO: 3.

In a further preferred aspect of the present invention the protease is selected from the group consisting of matrixmetalloproteases, preferably MMP2, MMP5, MMP9, ADAM10, ADAM17, ADAM9 and/or ADAM5.

In a further preferred aspect of the present invention the disease is selected from the group consisting of viral infections, cancer, a disease associated with chronic inflammation.

In a further preferred aspect of the present invention the disease/immune-status is characterized by the reactivation of human endogenous retroviruses (HERV). In a further preferred aspect of the present invention the sample is a sample obtained from a body fluid and/or extracellular supernatants.

A further aspect of the present invention relates to a method for in vitro evaluating the size and activity of the remaining HIV reservoirs in patients under retroviral treatment, using the above disclosed method for in vitro detection and/or monitoring of a disease in a sample method.

A further aspect of the present invention relates to a modified peptide obtained by combining a protease-sensitive peptide comprising 5 or more amino acids with a fluorophore-modification and a quencher-modification, wherein the fluorophore-modification is lipophilic, conferring membrane translocation potential to the substrate peptide, and the protease-specific cleavage site of the peptide is located between the fluorophore-modification and the quencher-modification, or a modified peptide obtained by combining a protease-sensitive peptide comprising 5 or more amino acids with an N- and/or C-terminal sequence comprising 5-20 membrane penetrating amino acids with a fluorophore-modification and a quencher-modification, wherein the protease-specific cleavage site of the peptide is located between the fluorophore-modification and the quencher-modification.

A further aspect of the present invention relates to the use of such a modified peptide for the in vitro measurement of enzymatic activity of a protease in extracellular vesicles.

A further aspect of the present invention relates to the use of such a modified peptide as a specific peptide in a method for in vitro detection and/or monitoring of a disease in a sample wherein the specific peptide serves as a substrate for the disease-associated protease.

A further aspect of the present invention relates to a kit comprising the above described modified peptide.

A further aspect of the present invention relates to the use of ADAM-protease activity as an in vitro marker of tumor activity and/or presence of tumor cells, In a further preferred aspect of the present invention the activity of the ADAM-protease is measured within extracellular vesicles.

Advantageous Effects

The inventors of the present invention could show that by using the method according to the present invention which is based on the detection of disease-associated proteases in EVs it is possible to detect and/or monitor a disease in a fast and reliable manner.

The detection method according to the present invention is at least 10-100 times more sensitive compared to known methods not based on enzyme activity.

Using the method according to the present invention it is possible to detect virus activity and viral reservoirs in patients already under antiviral-treatment and without detectable viral antigens as detected by conventional assay systems.

Furthermore, the inventors found out that ADAM-protease can be used as a marker of tumor-activity and/or tumor cell presence.

With the method of the present invention it is possible to detect an enzymatic activity directly in EV of the sample without the need of further vesicle disruption/lysis. This is relevant in order to measure the activity of the protease in its physiological membrane position where it may associate with inhibitors (the TIMP proteins) or activators of their protease activity. Such associations may be lost upon vesicle disruption/lysis. Furthermore, due to its sensitivity, the method enables detection of diseases in patients already under therapy and thus, allowing the indirect assessment, e.g. in the case of a viral infection, of an otherwise undetectable viral activity.

The modified peptide according to the present invention is preferably used as specific peptide in the method for in vitro detection of a disease in a sample of the present invention.

By using the modified peptides it is possible to detect the protease within EVs without disrupting/lysing the EVs.

By using the method for detecting a disease according to the present invention it is possible to evaluate the relative size and activity of the remaining HIV reservoirs in patients under retroviral treatment.

Assessment of an enzymatic activity, rather than a secreted protein, is expected to be much more sensitive than conventional biomarkers/tumor markers. For example, ADAM17 activity in HIV plasma is very high when measurement of viral proteins is negative or just above detection level.

Thus, ADAM activity can be assessed when other markers turn/are negative, like viral copy number in HIV and tumor markers in melanoma.

Measuring ADAM activity correlates with the HIV viral reservoir and the size of the melanoma tumor mass before conventional x-ray-based imaging techniques and tumor markers reflect tumor cell proliferation.

The use of membrane penetrating substrate FRET peptides that recognize either specific or multiple proteases allows the setup of a simple assay procedure even without EV-purification

BRIEF DESCRIPTION OF THE DRAWINGS

FIGS. 1A-1G: The Nef signaling complex and paxillin activate and secrete TACE.

(FIG. 1A) Composition of NAKC and events demonstrated in this report. Coexpression of NAKC factors activates Erk1/2 (1), which is the pivotal kinase activating TACE (2). NAKC also induces the secretion of TACE via extracellular vesicles (EV) (3). Events are triggered by interaction of TACE with Eed and Paxillin (4).

(FIG. 1B) Transfer of TACE into EV after coexpression of mNAKC (hnRNPK, PKCδ, Lck) and Nef. Lysates of transfected 293T cells (cell) and purified EV (EV) were blotted as indicated. Insert*: longer exposure revealing transfer of endogenous TACE into EV (left double-arrow). Transfer of transfected TACE is indicated by the right double-arrow. The black and red single arrows depict precursor (inactive) and active form of TACE (135 vs. 95 kDa).

(FIG. 1C) Immunoblot of TACE and phospho-Erk1/2 on 293T cell lysates transfected as indicated.

(FIG. 1D) Immunoblot for phospho-paxillin (α-Y118) and phospho-Erk1/2 on 293T cell lysates transfected as indicated.

(FIG. 1E) Immunoblot for TACE after immunoprecipitation of paxillin, Nef and NAKC components. Factors were transfected pairwise (e.g. Nef and TACE, upper graph) or in concert with the whole Nef/NAKC complex (lower graph). Input: 293T lysates transfected with TACE and mNAKC.

(FIG. 1F) Immunoblot for TACE in the presence of wt paxillin or a paxillin LD4 deletion mutant (PaxΔLD4) as indicated, scoring for (1) TACE activation (cell lysate, middle panel), (2) TACE binding to paxillin (after Paxillin-immunoprecipitation (IP), upper panel) and (3) presence of TACE in EV (lower panel).

(FIG. 1G) Colocalization of TACE with native paxillin (red arrow) but not PaxΔLD4 by confocal microscopy after co-transfection into 293T cells.

(FIG. 2A) Coimmunoprecipitation of paxillin and TACE using paxillin phosphorylation mutants as indicated. Lower graph: cell lysates blotted for TACE. Input and arrows as in 1E.

(FIG. 2B) Confocal colocalization analysis of TACE (antibody staining) and GFP-paxillin (wt and phosphorylation mutants) after cotransfection with Nef/mNAKC.

(FIG. 2C) Coimmunoprecipitation of paxillin and TACE in the presence of constitutive active (Pak1L107F; Pak2L106F) or transdominant negative (Pak1R; Pak2R) Pak1 and -2 mutants.

(FIG. 2D) Coimmunoprecipitation of paxillin and TACE in the presence of constitutive active Pak1 and -2 and paxillin phosphorylation mutants as indicated. Numbers are explained in the text.

(FIG. 2E) Pak1 and Pak2 activation (phosphorylation) after transfection of NAKC factors (individually and in combination) into 293T cells.

(FIG. 3A) Cartoon depicting paxillin protein domains, interactors and phosphorylation sites based on (Deakin and Turner, 2008).

(FIG. 3B) Presence of TACE in EV lysates purified from supernatants of 293T cells transfected as indicated.

(FIG. 3C) Immunoblot analysis of lipid rafts and cytosol of 293T cells transfected with TACE, paxillin, Nef/mNAKC and wt Pak1 and 2 as indicated. Transferrin receptor (TfR) served as marker for cytosolic—and cholera toxin (CTX) for lipid raft proteins.

FIGS. 4A-4D: Melanoma cells regulate ADAM10 transfer into EV through paxillin/Pak1/2.

(FIG. 4A) Immunoblot on lysates of primary melanocytes (last lane) and 7 primary melanoma cell lines as depicted (ML: Melanoma Line, S28: SK-Mel 28). For comparison a lysate of Nef/mNAKC transfected 293T cells was used (first lane).

(FIG. 4B) Immunoblot on lysates of EV purified from supernatants of 6 primary melanoma lines (ML). For comparison served a lysate of Nef/mNAKC transfected 293T cells (last lane).

(FIG. 4C) Coimmunoprecipitation of ADAM10 by paxillin using melanoma cells (ML1 and 3) that had been transfected with vector, wt and mutant Pak1/2 constructs as indicated.

(FIG. 4D) Cell (cell) and EV (EV) lysates from/derived from two melanoma cell lines (ML1 and 3) blotted for transfected (two days before: GFP-paxillin WT and GFP-paxillinS272/4A) and endogenous paxillin.

FIGS. 5A-5G: Nef/NAKC-activated TACE cleaves proTNF□ in endosomal compartments.

(FIG. 5A) Cartoon depicting the GFP-proTNF-RFP fusion protein and its TACE cleavage site.

(FIG. 5B) FACS analysis of GFP-proTNF-RFP transfected 293T cells and coexpression of mNAKC, TACE and Nef as indicated.

(FIG. 5C) Summary and quantification of FACS analysis as shown in (FIG. 5B). Depicted is the number of GFP/RFP double positive (yellow) cells after coexpression of mNAKC, Nef and TACE as indicated. Error bars (standard deviation) were calculated on the basis of triplicates.

(FIG. 5D) Immunoblot of cell lysates from (FIG. 5C). Expression levels of TNF-R (box) are depicted in % of maximum signal (red arrow, 100%).

(FIG. 5E) Confocal analysis of 293T cells transfected as indicated. For description of arrows see text.

(FIG. 5F) Quantification of yellow (proTNFα) and red (mature TNFα) vesicular compartments on one confocal level/cell. For each condition 20 randomly selected cells were chosen (see examples at the right). Error bars indicate standard deviation of the mean of 20 cells.

(FIG. 5G) Infection of HeLaCD4 cells with HIV-1 wt, HIV-1☐nef or mock after cells had been transfected with GFP-proTNF-RFP. After three days expression of GFP-proTNF-RFP (yellow signal) was assessed by FACS in gp120-positive cells. Error bars (standard deviation) were calculated on the basis of triplicates. Probability of error is expressed as two-tailed P-values. The bar diagram summarizes the FACS analysis.

(FIG. 6A) Quantification (bar diagram) of yellow (proTNFα) and red (mature TNFα) vesicular compartments (examples at the bottom) in 20 randomly selected GFP-proTNF-RFP-containing target cells (per condition) after incubation with purified EV. EV were derived from transfected 293T cells as indicated. Error bars indicate standard deviation of the mean of 20 randomly selected cells.

(FIG. 6B) TNFα secretion of resting PBMC after incubation with EV derived from transfected 293T cells as indicated or stimulated with PHA (5 μg/ml). CN: CD8-Nef. TAPI: ADAM inhibitor, U0126: Erk1/2 inhibitor, IPA-3: Pak inhibitor.

(FIG. 6C) TNFα secretion of resting PBMC after incubation with EV derived from two melanoma cell lines (ML1, ML3). Error bars (standard deviation) in FIGS. 6B and 6C were calculated on the basis of triplicates.

(FIG. 6D) Uptake of Nef-induced and PKH-labeled EV by resting PBMC after 2 h of incubation demonstrated by FACS and confocal microscopy.

(FIG. 6E) Immunoblot of EV lysates (50 μg) purified from 5 ml of plasma of 2 HIV-1 (HIV01, HIV02), 5 melanoma patients (clinical stage IV w/wo tumor burden) and 2 healthy controls. n.s.: non-specific. Gag lys.: 293T cell lysate transfected with HIV-1 gag.

FIGS. 7A-7C: Summary of events leading to TACE activation and secretion via EV.

(FIG. 7A) Membrane-associated Nef first recruits Eed and then the rest of the NAKC complex. Pak2 associates with the Nef core domain (Renkema et al., 2001). Since Eed binds integrin subunits, NAKC complexes with integrin-paxillin-TACE (1). This leads to the activation of Erk1/2 (2) (likely associating with paxillin), the phosphorylation of paxillin by Lck and Pak2 (3) and the phosphorylation of the TACE precursor by Erk1/2 (4). In resting cells paxillin is kept inactive through phosphorylation by Pak1 (5). Nef/NAKC, however, inactivates Pak1 (6).

(FIG. 7B) These the events change the complex leading to the activation of TACE (1), the association of paxillin with activated TACE (2) and their transfer into lipid rafts (3) along with Nef and probably also the integrin complex.

(FIG. 7C) Once transferred to lipid rafts, activated TACE is shuttled into EV via endosomal compartments.

For transmission electron microscopy, cells were fixed in 0.1 M sodium cacodylate buffer containing 2.5% glutaraldehyde (pH. 7.2) at room temperature for 20 min. After washing three times in 0.1 M sodium cacodylate cells were post-fixed in 1% osmium tetroxide in the same buffer. After 1 h of incubation at room temperature, cells were dehydrated through graded series of ethanol solutions and finally embedded in Agar 100 epoxy resin. Thin sections were stained with lead citrate and uranyl acetate and examined with a Philips 208s electron microscope.

Figure 9:
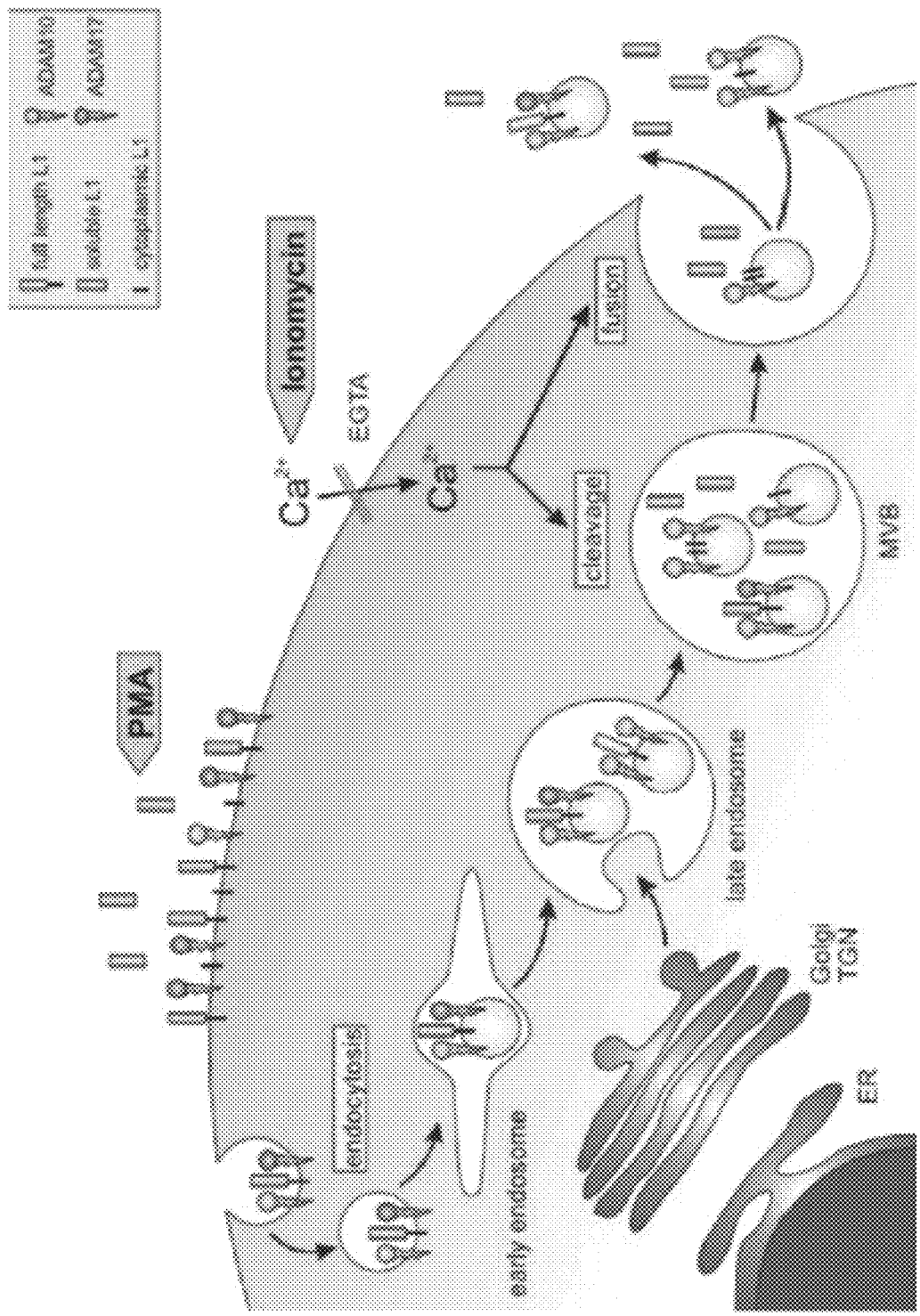

FIG. 9: Ectodomain cleavage in Exosomes: a model (from Stoeck et al. 2006, Biochem J. 2006; 393: 609-618) demonstrating the internationalization (left upper part) and packaging of ADAM 10/17 into Exosomes. After Exosomes are released from multivesicular bodies (MVB) the catalytic center of the proteases is located on the surface of the vesicle.

Figures 10A, 10B:
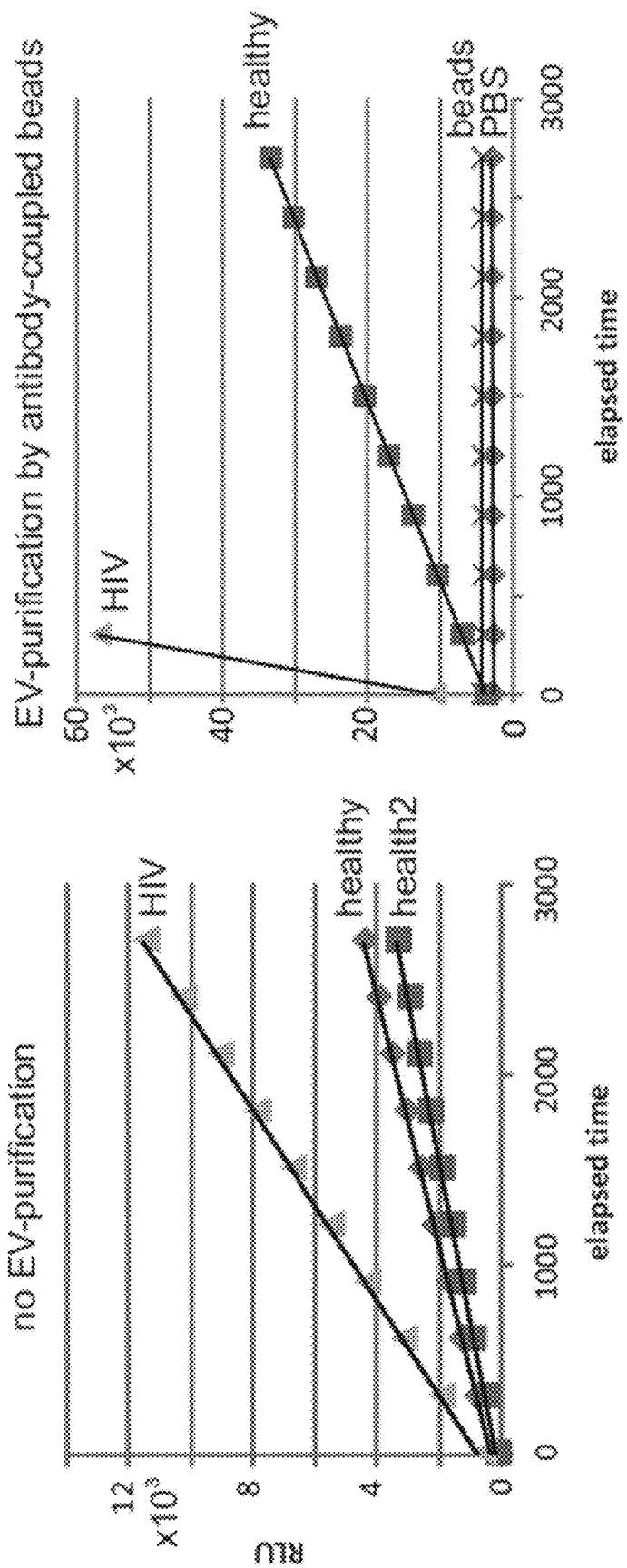

FIGS. 10A-10B: Purification of plasma EV using antibody-coupled magnetic beads increases the sensitivity of an ADAM17 substrate FRET peptide based enzymatic assay. (FIG. 10A) Incubation of the FRET peptide with 1 ml of plasma (1 HIV-infected individual and 2 non-infected controls) EV purification by ultracentrifugation as explained in the text. (FIG. 10B) Incubation of the ADAM17 substrate FRET peptide with EV purified by antibody-couples beads. The antibodies were specifically developed to recognize EVP.

Figure 11:
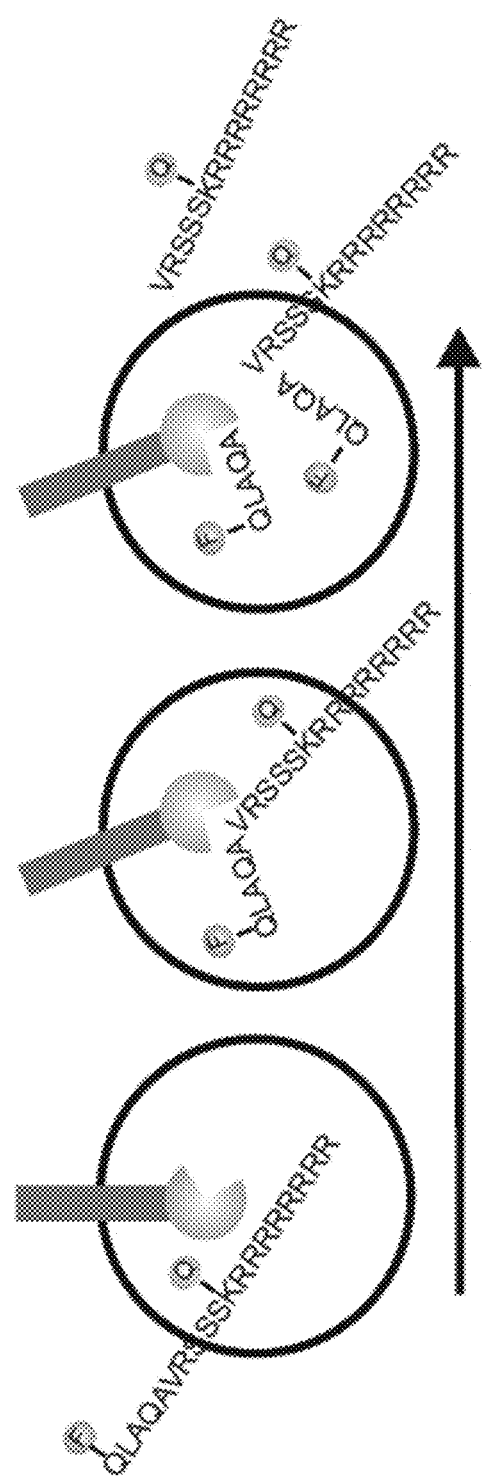

FIG. 11: Cartoon demonstrating membrane penetration of an arginine tagged FRET peptide substrate (SEQ ID NO: 12) of the ADAM17 protease. The FRET peptide is cleaved inside an EV. Placement of the arginine stretch C-terminal to the quencher (Q) may lead to the accumulation of the fluorochrome-modified portion of the substrate (SEQ ID NO: 13) inside the EV, whilst the remainder of the cleaved peptide (SEQ ID NO: 14) is shedded into extravesicular space.

Figure 12:
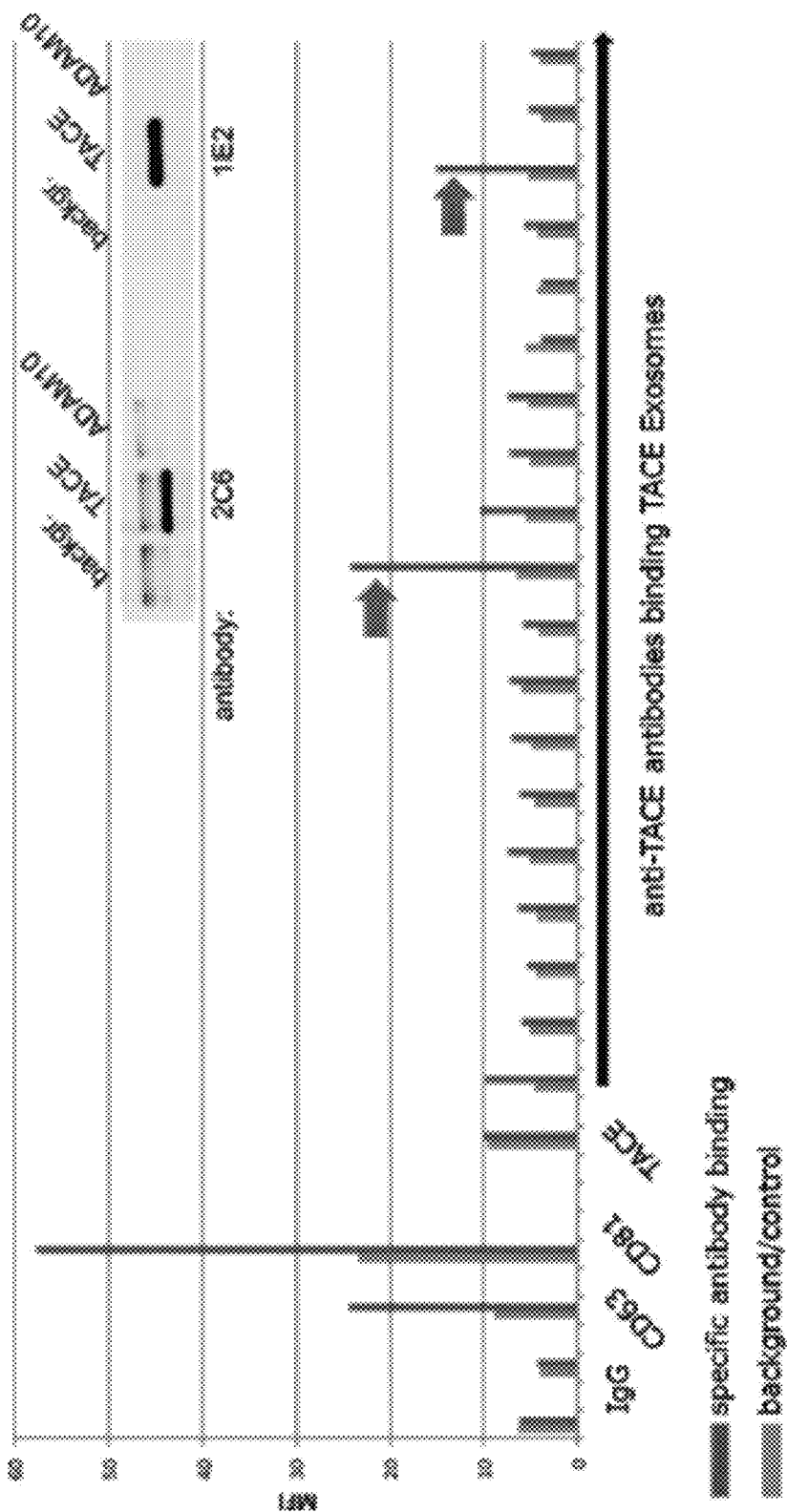

FIG. 12: FACS-Analysis of EVP demonstrating the upside-down orientation of ADAM17. Monoclonal antibodies were raised against the C-terminus of ADAM17 (peptide sequence: KLQRQNRVDSKETEC; SEQ ID NO.: 11). Hybridomas that were obtained were tested if they could stain the EVP by FACS analysis. FACS analysis of bead-coupled EV was performed as previously described (Thery et al., 2006; Muratori et al., 2009). Briefly, 6 μg EV prepared from cell culture supernatants were incubated with 10 μl of 3.9-μm diameter latex beads surfactant-free aldehyde/sulfate (Invitrogen, A37304) in a final volume of 15-20 it for 15 min at room temperature. To each sample 1 ml PBS was added and incubated overnight at 4° C. 110 μl of PBS/1 M glycine was added to each sample followed by incubation for 30 min at room temperature. EV-coated beads were washed 3 times in PBS/0.5% (w/v) BSA and resuspended in 500 μl PBS/0.5% (w/v) BSA. 10 μl EV-coated beads were incubated with 50 μl antibody diluted in PBS/0.5% BSA for 30 min at 4° C., followed when necessary by incubation with a PE or FITC-conjugated antibody, and analyzed by FACS. Two clones (2C6; 1E2) stained EVP (arrows) similar as the positive controls (CD63, CD81). Conversely an antibody directed against the N-terminus of ADAM17 was negative (TACE). The insert (Western blot) shows that both antibodies (2C6, 1E2) recognize the activated form of ADAM17.

Figure 13A:
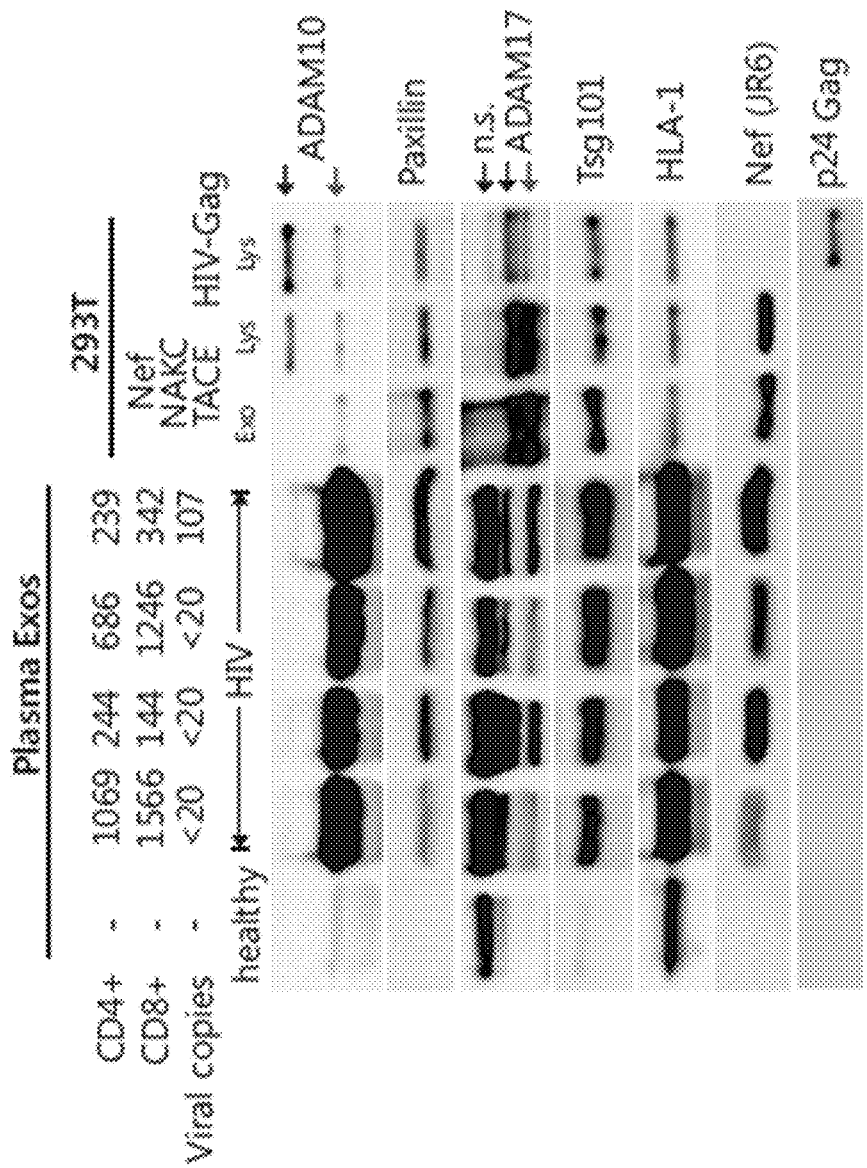
Figure 13B:
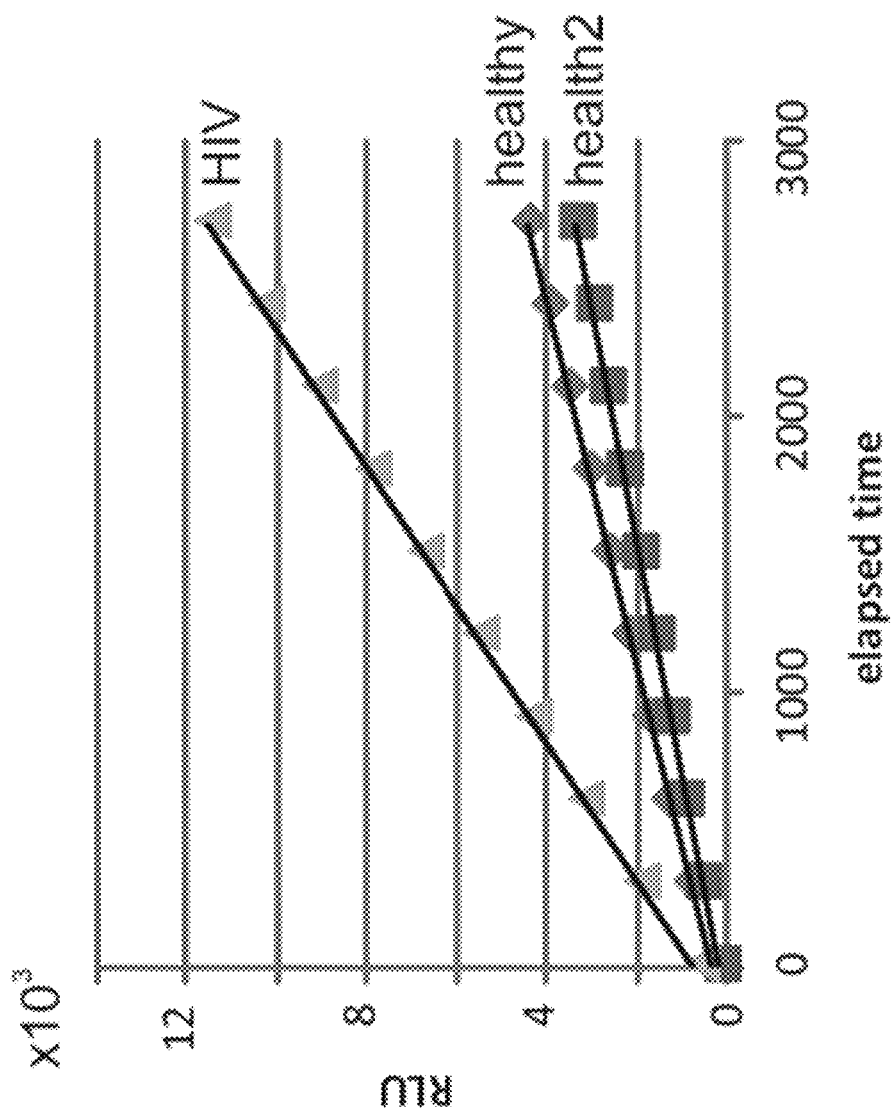

FIGS. 13A-13B: Presence and activity of active ADAM 17 and 10 in EV.

(FIG. 13A) Western blot, performed by standard procedures, of plasma EV from HIV patients and controls for the presence of ADAM17, ADAM10, Nef and control proteins. In general 20 μg of cellular protein lysate and 10 μg of microvesicle lysate were loaded per lane. The blots were incubated with commercial available antibodies as indicated. The monoclonal antibodie α-Tsg101 was purchased from Santa Cruz; α-paxillin (clone 5H11) form Millipore;

α-ADAM10, α-ADAM17, α-Gag and α-Nef from Abcam; α-HLA from Pharmingen. For EV purification from patient samples, 5 ml blood plasma was diluted with 5 ml PBS and centrifuged for 30 min at 2000 g, 45 min at 12000 g and ultra-centrifuged for 2 h at 110,000 g. Pellets were resuspended in 1 ml PBS and 40 μl of antibody-coupled Micro-Beads were added for 1 h and subsequently subjected to magnetic immunoisolation with MACS® Technology (Miltenyi Biotech, Bergisch Gladbach, Germany) using MS columns. The EV were finally eluted with 45 μl of hot (95° C.) loading buffer and all of the vesicle lysate was subsequently analyzed by western blot.

(FIG. 13B) EV-associated ADAM17 enzymatic activity measured by FRET substrate cleavage by EV isolated from 0.5 ml plasma of one HIV patients and two controls. EV were purified as described above. TACE activity was measured using the SensoLyte®520 TACE (α-Secretase) Activity Assay Kit from AnaSpec, according to the manufacturer's procedures.

Figure 14A:
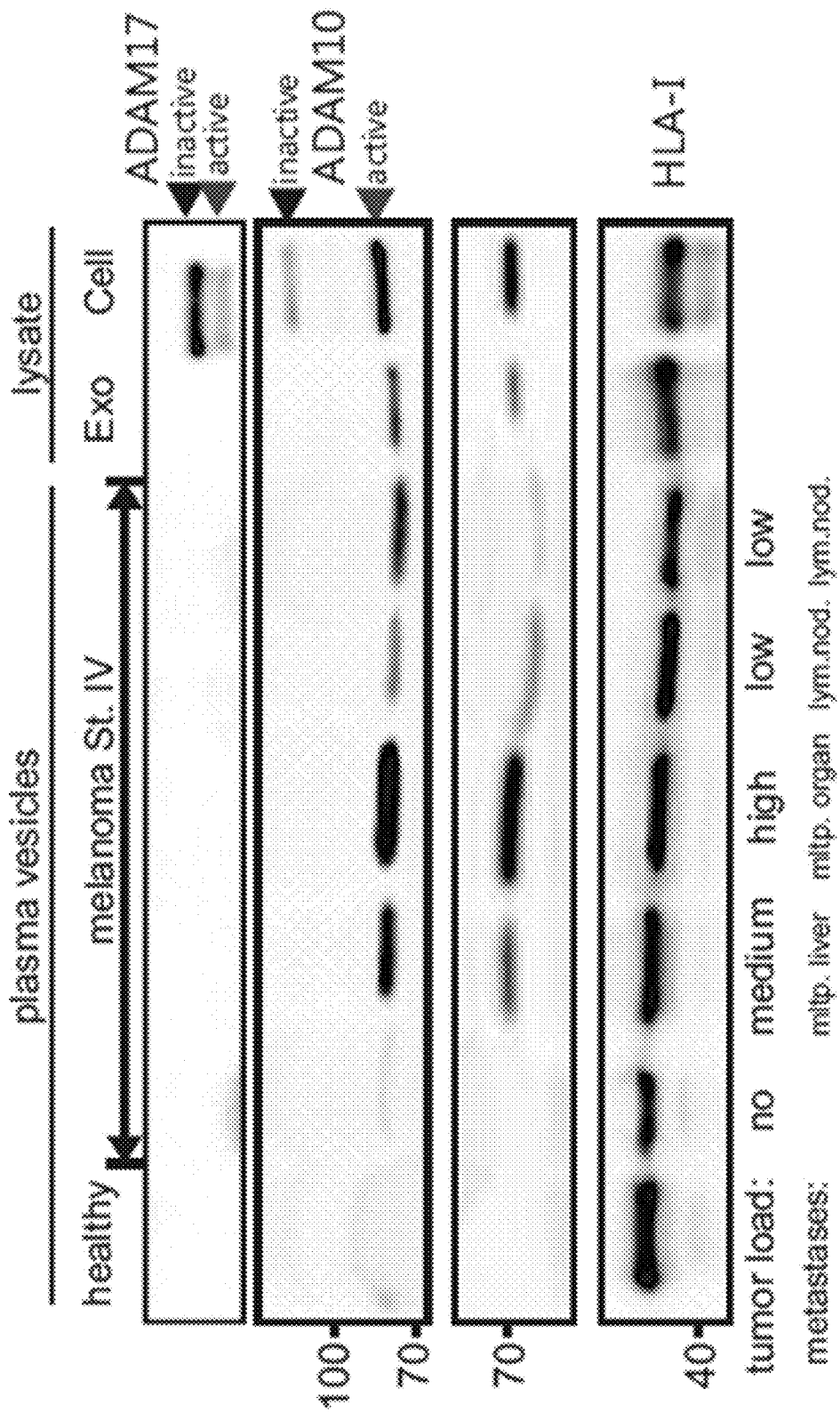
Figure 14B:
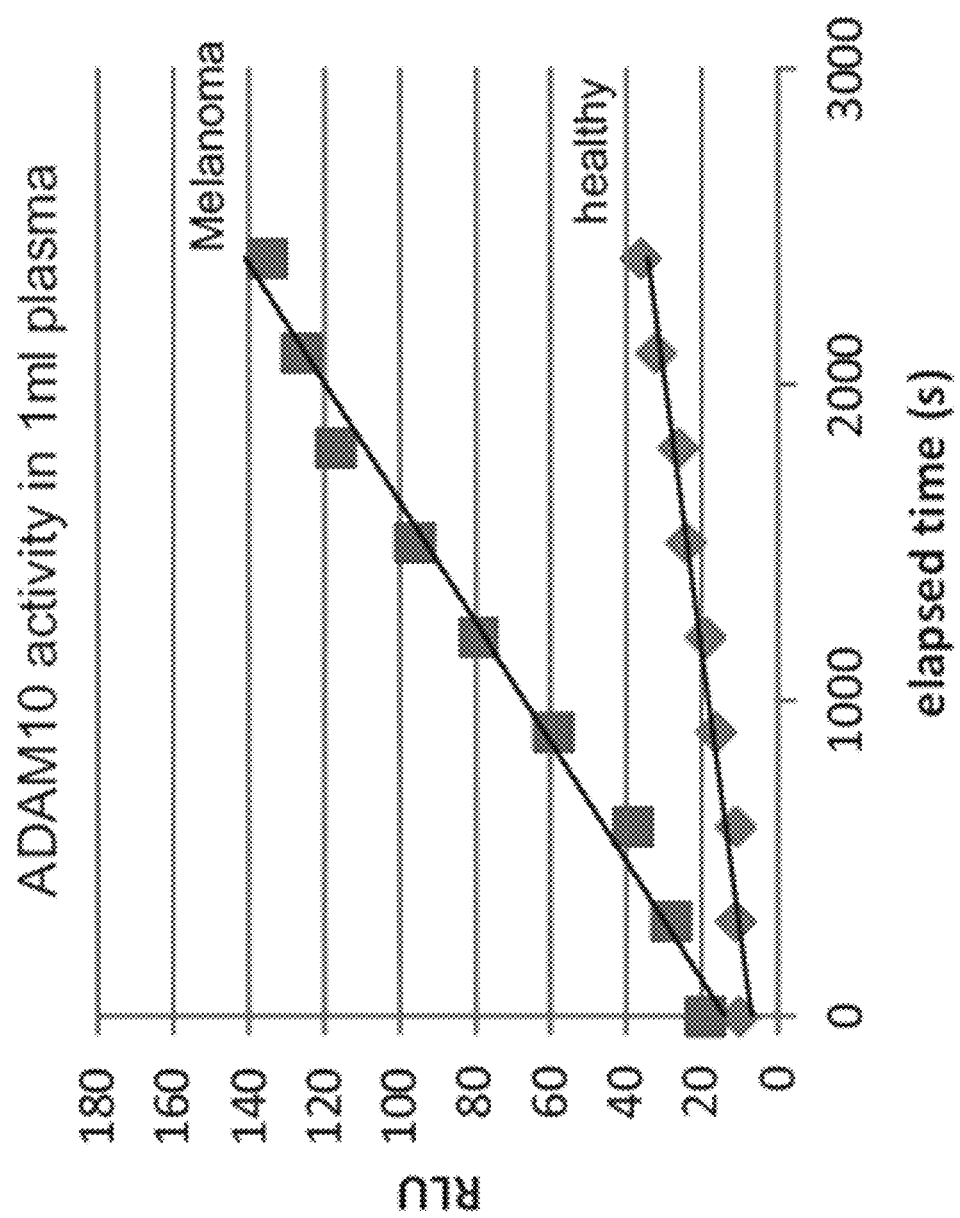

FIGS. 14A-14B: Presence and activity of active ADAM10 in EV from melanoma patients.

(FIG. 14A) Western blot of plasma EV from melanoma patients and controls for the presence of ADAM10 and control proteins. For experimental details see FIG. 13A (FIG. 14B) EV-associated ADAM10 enzymatic activity measured by FRET substrate cleavage in 0.5 ml plasma of one melanoma patient and one control. For experimental details see FIG. 13B.

FIGS. 15A-15D: The Nef-associated kinase complex (NAKC). (FIG. 15A) We first described the complex by demonstrating that the N-terminus of Nef associated with Lck and a serine kinase activity. The Kinases, however, did not bind directly to Nef (Baur et al., 1997). (FIG. 15B) Using a two hybrid screen we found that the NAKC-interacting domain of Nef bound directly the polycomb protein Eed and mimicked an integrin signal (Witte et al., 2004). The serine kinase activity could be identified as PKCδ (Wolf et al., 2008a). (FIG. 15C) The hnRNPK protein was identified as a linker between Eed and the kinases PKCδ, Lck and PI3 kinase. All proteins were found to act as a coherent complex that activated Erk1/2 (Wolf et al., 2008b). (FIG. 15D) The whole complex was found to be essential for the Nef-induced secretion of EV from T cells (Muratori et al., 2009).

FIGS. 16A-16F: After Nef/NAKC expression activated TACE is uploaded into extracellular vesicles (EV). EV were purified from 60 ml culture supernatant of 293T cells by standard differential centrifugation after transfection with vector and TACE, or Nef, mNAKC (PKCδ, hnRNPK, Lck) and TACE, before being further processed through a sucrose gradient. Individual fractions were blotted against HLA class I and TACE.

Figure 17A:
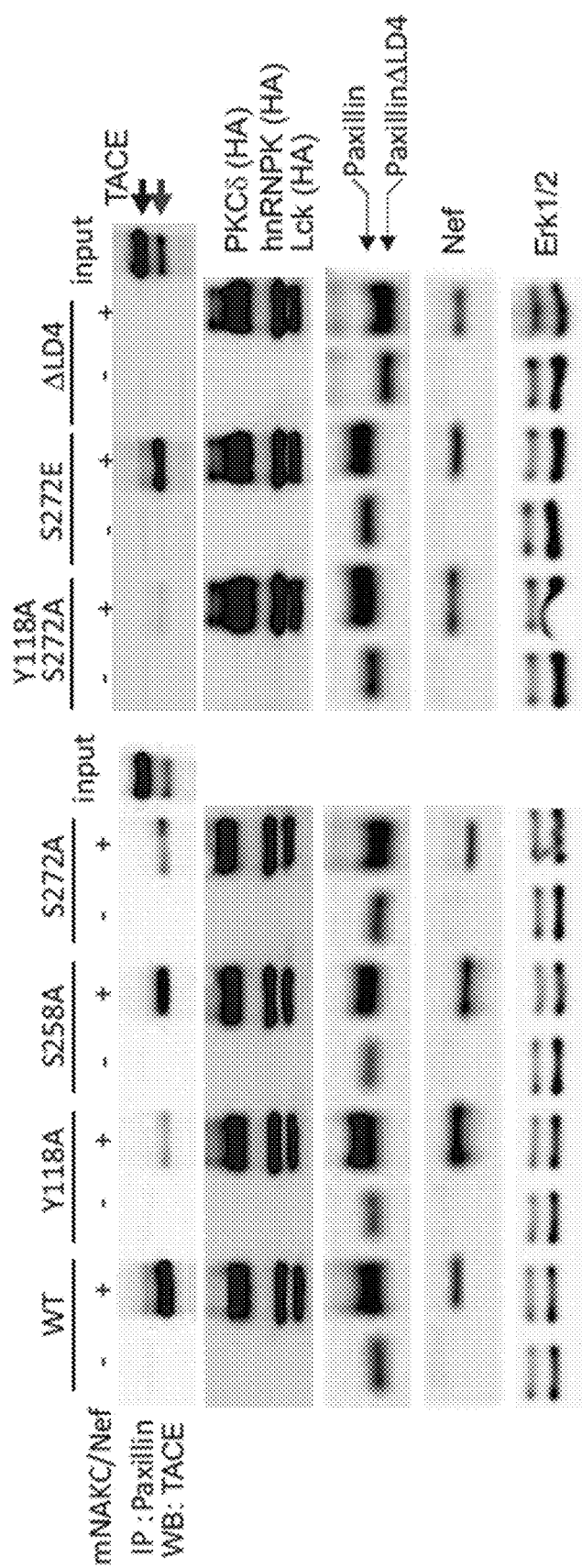
Figure 17B:
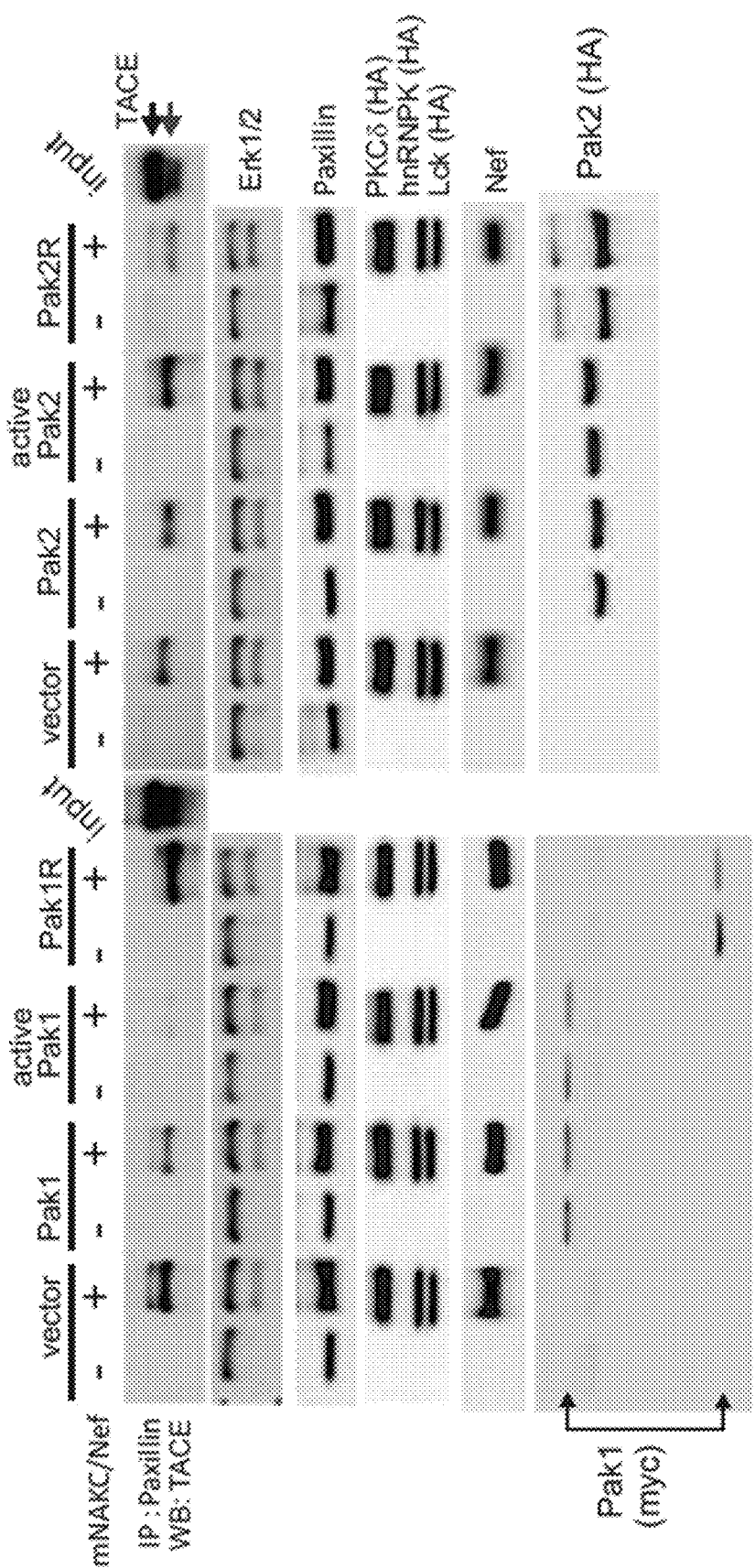

FIGS. 17A-17B: Transfected 293T cells release extracellular vesicles (EV) with characteristics (size, floating properties, surface markers) typical for microvesicles/exosomes. (FIG. 17A) Electron micrographs of EV purified from culture supernatants of 293T cells transfected with Nef and the Nef-associated kinase complex (NAKC). (FIG. 17B) Sucrose gradient of EV obtained as in FIG. 17A. Individual fractions were blotted for CD81.

Figure 18A:
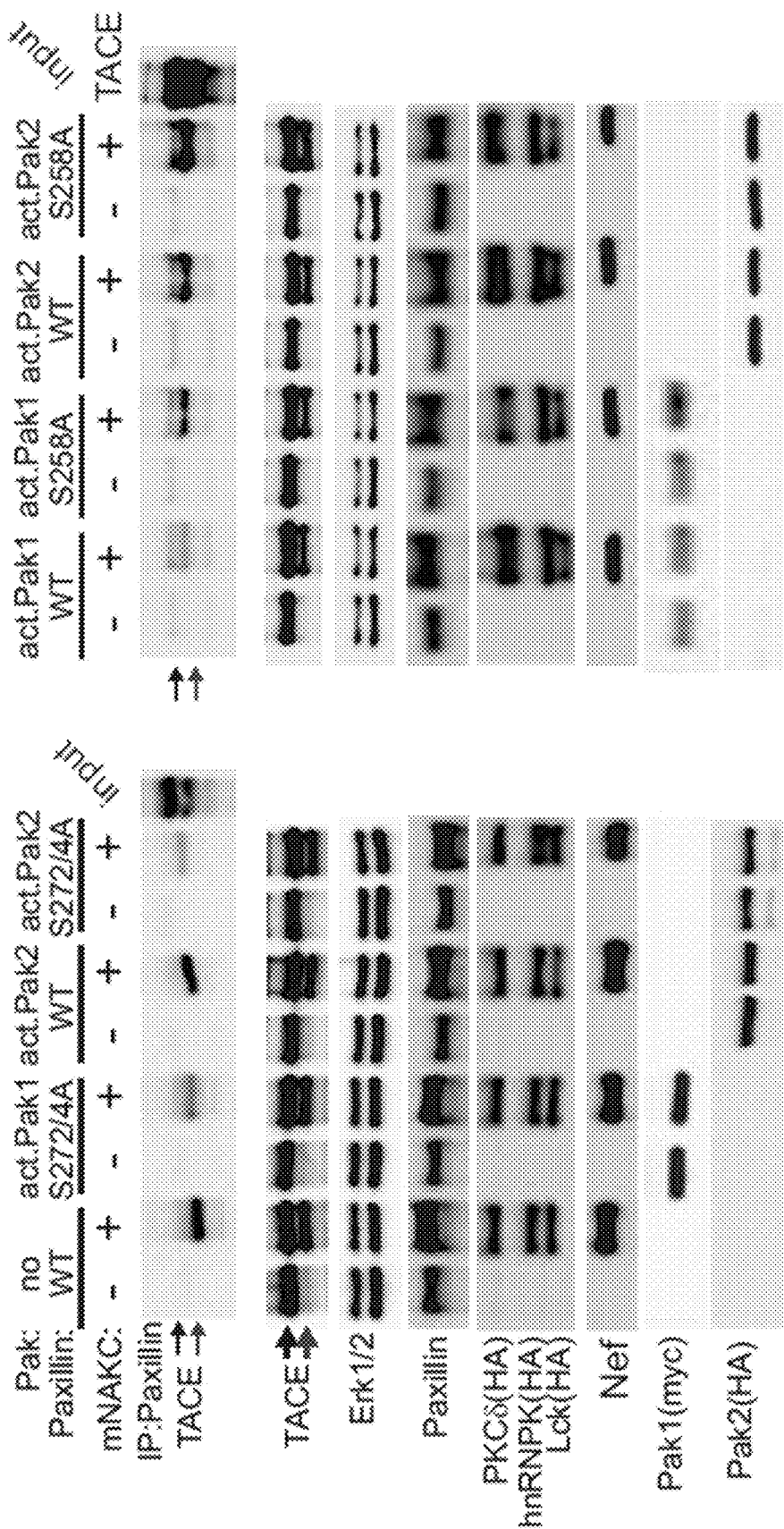
Figure 18B:
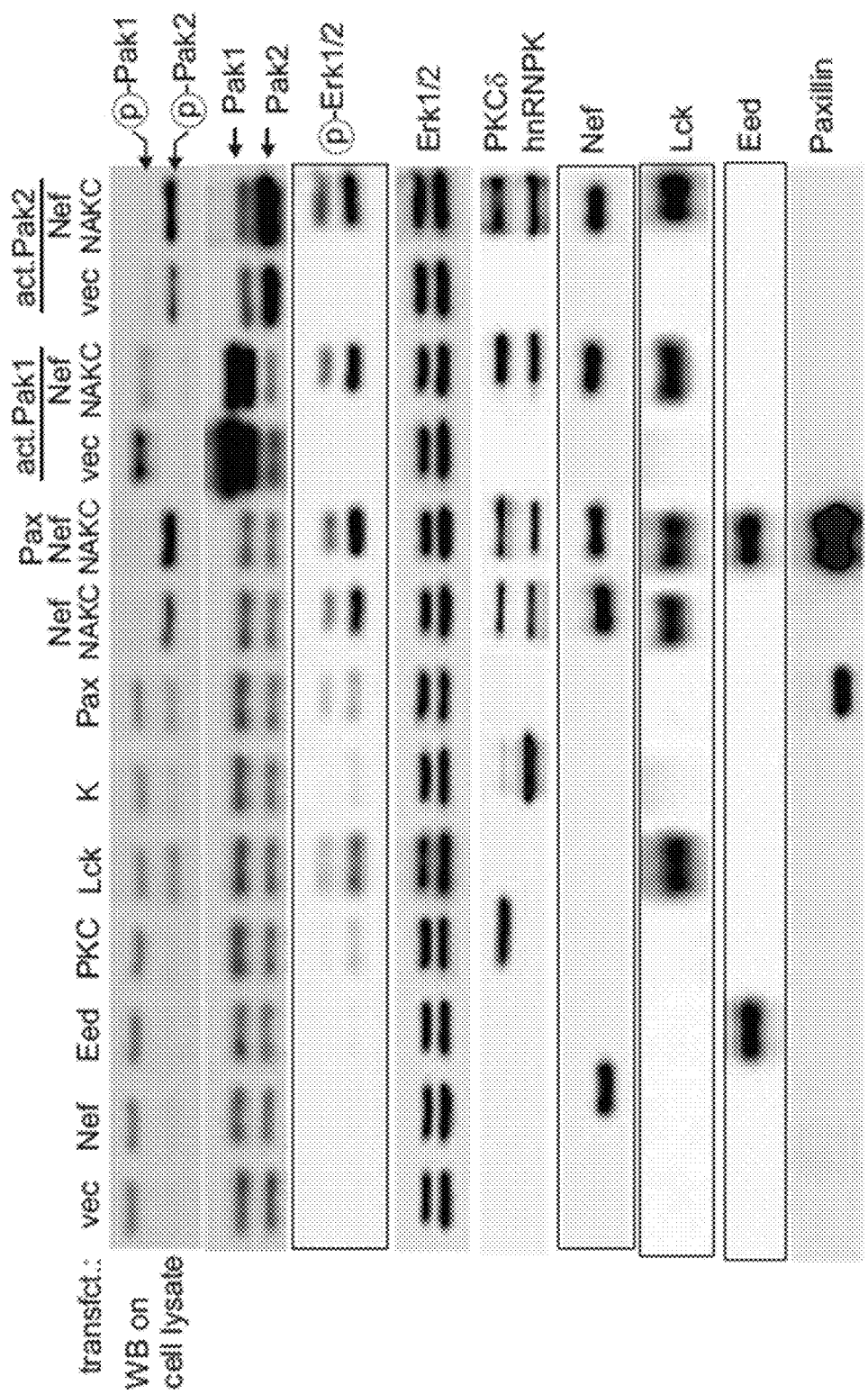

FIGS. 18A-18B: Protein expression control for immunoblotblot analysis shown in FIG. 1B. 293T cells were transfected with NAKC factors alone or in combination as indicated and cytoplasmic lysates were blotted for each factor transfected.

Figure 19A:
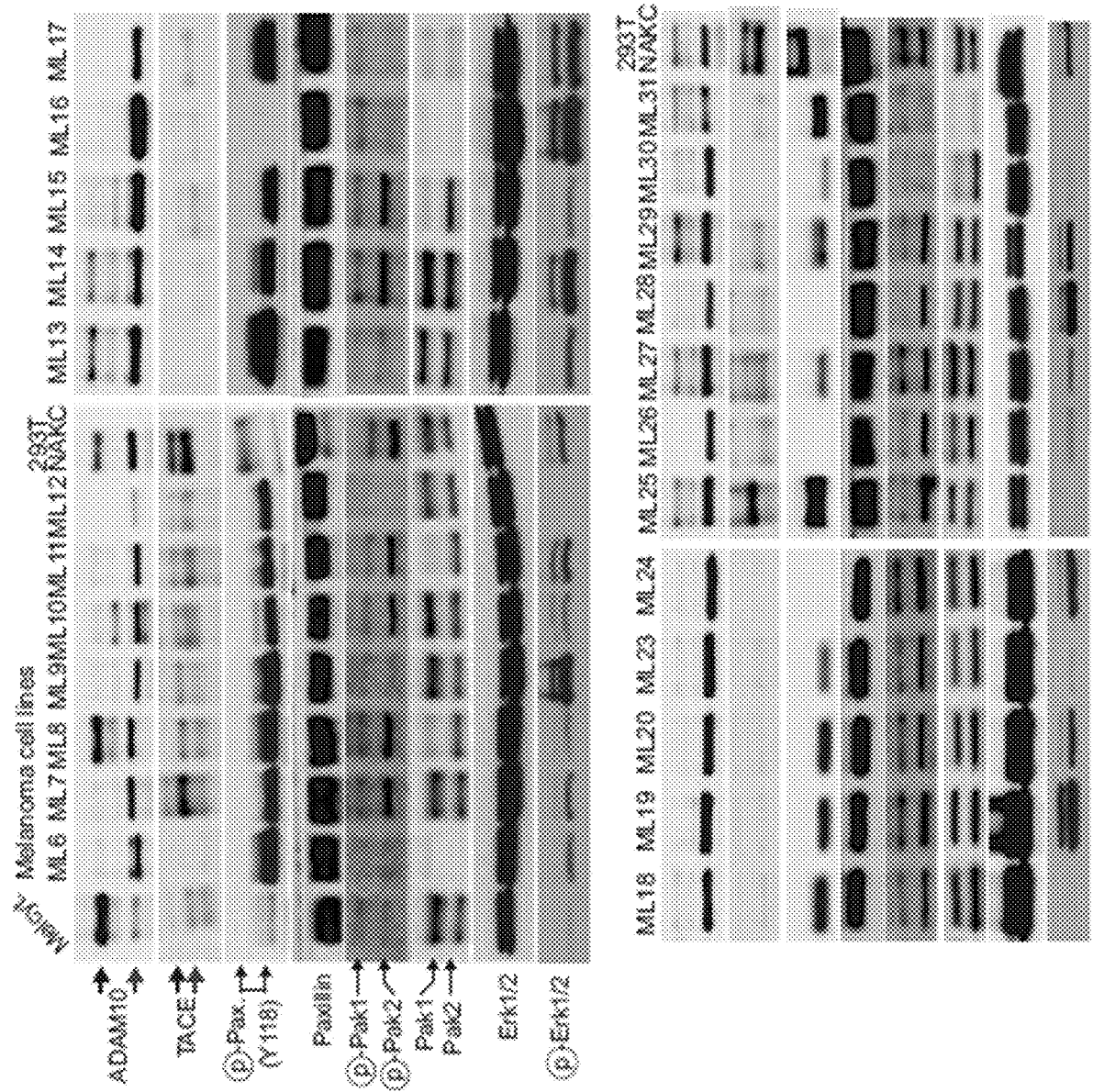
Figure 19B:
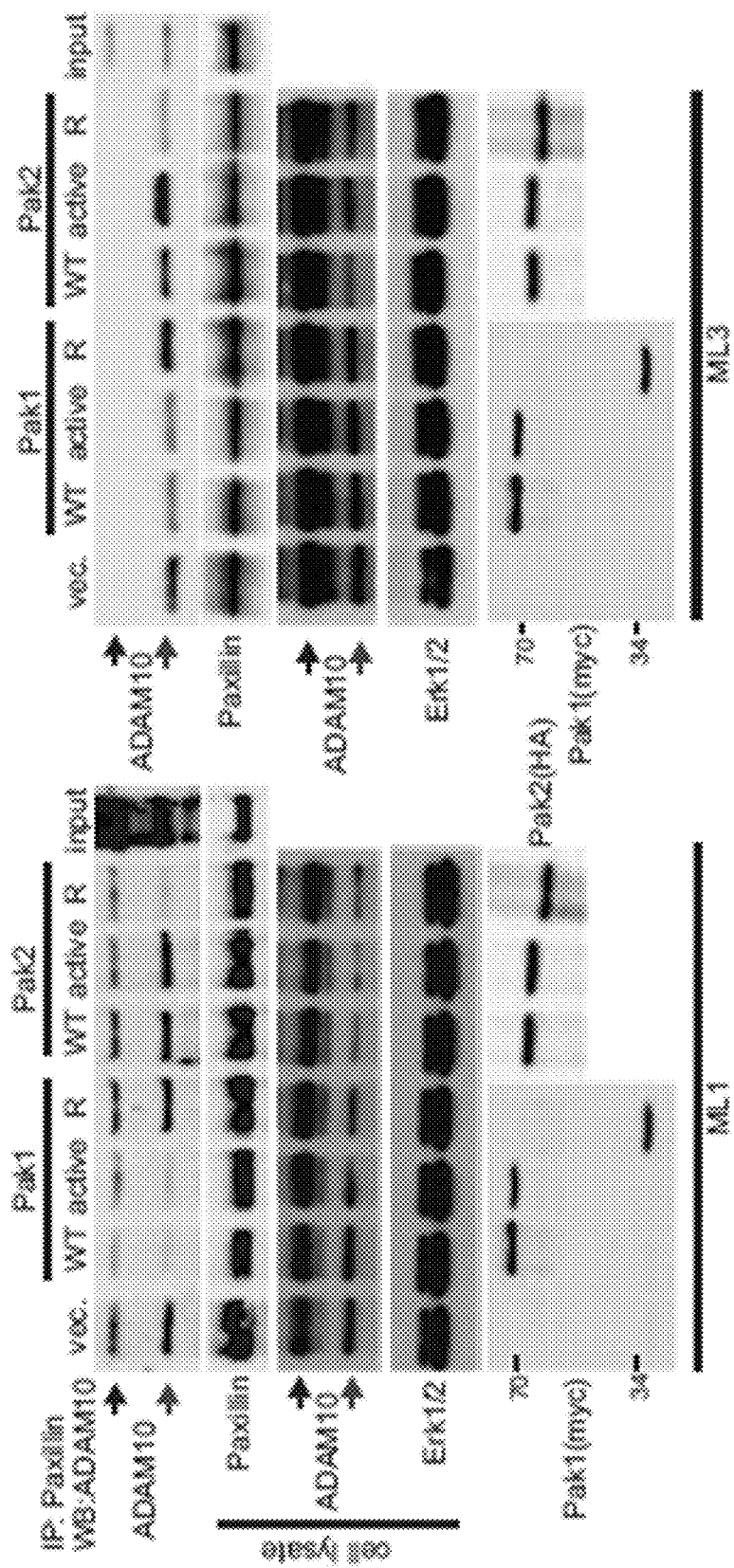

FIGS. 19A-19B: Protein expression control for immunoblot shown in FIG. 10. 293T cells were transfected with paxillin, Nef and NAKC factors as indicated and cell lysates were blotted for each factor transfected, endogenous Erk1/2, endogenous phospho-Erk1/2, paxillin and phospho-paxillin (Y118).

Figures 20A, 20B:
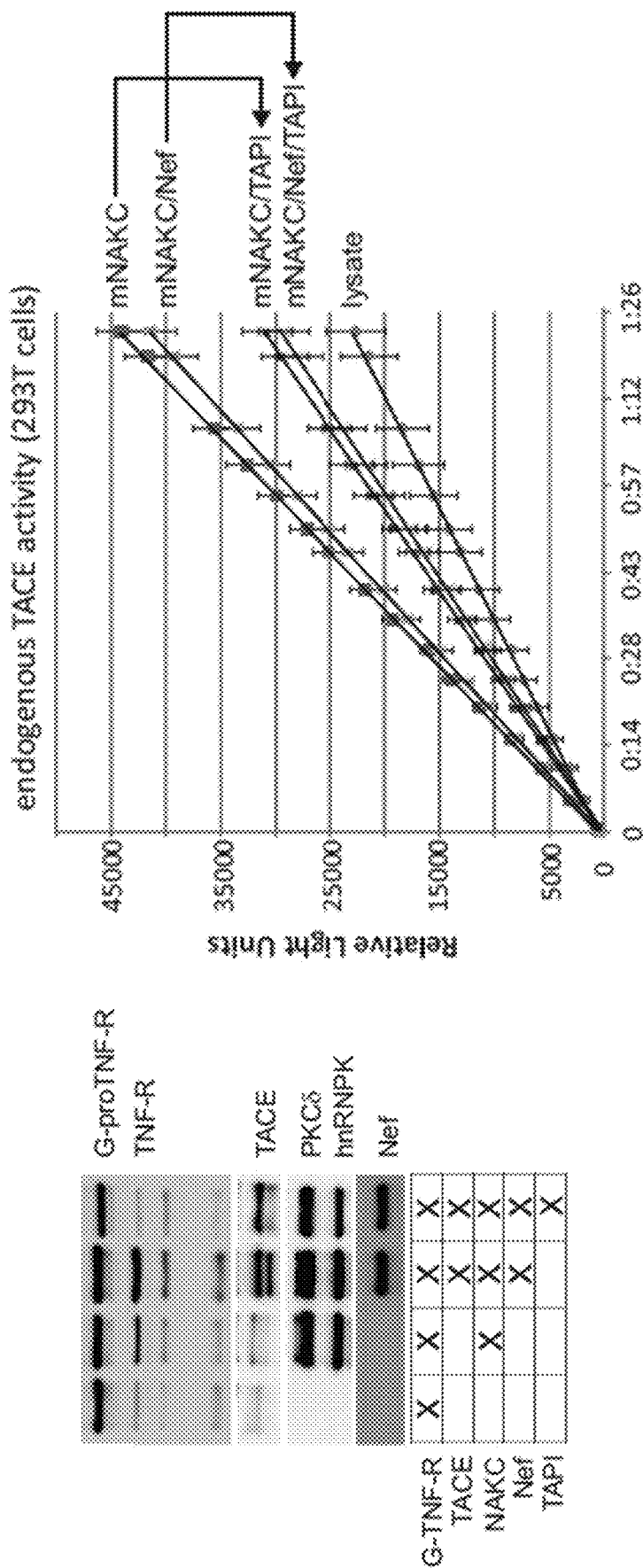
Figure 20C:
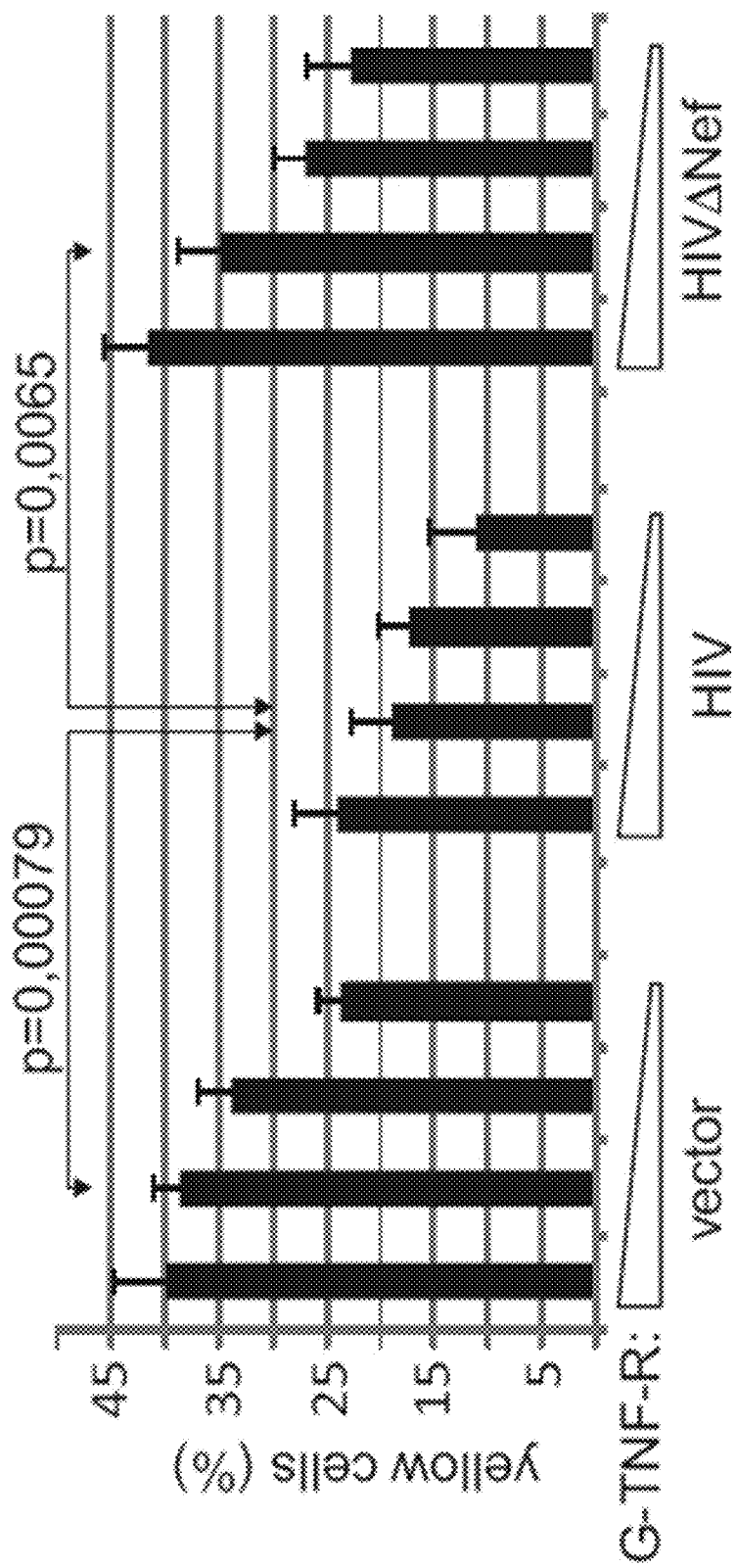

FIGS. 20A-20C: Protein expression control for immunoblot shown in FIG. 5D. 293T cells were transfected with GFP-proTNF-RFP, Nef, mNAKC factors and TACE as indicated and cell lysates were blotted for each factor transfected.

FIG. 21: GFP-proTNF-RFP is cleaved in endosomal compartments. Confocal image and cartoon showing how GFP-proTNF-RFP containing compartments (yellow) successively separate into GFP-prodomain (green) and mature TNFα-RFP (red) vesicular compartments within the cytoplasm.

DETAILED DESCRIPTION OF THE INVENTION

The method according to the present invention for in vitro detection and/or monitoring of a disease in a sample comprises the following steps: (1) providing a sample from a patient, and (2) measuring the enzymatic activity of at least one disease-associated protease in extracellular vesicles in the sample.

The enzymatic activity of the at least one disease-associated protease is measured in extracellular vesicles in the sample, preferably the extracellular vesicle is not an exosome, more preferably the extracellular vesicle is an EVP.

The term "extracellular vesicle" (EV) as used within the present application describes all vesicles that are released by a living cell (in contrast to a dying or apoptotic cell), there is no restriction or exclusion criteria based on size (in nanometer), markers (e.g. surface marker) or release mechanism (e.g. MVB-derived).

The term EVP (Extracellular Vesicle containing Protease), as used within the present application, describes a subgroup of extracellular vesicles (EV) that contain an enzymatically active protease (e.g. matrixmetalloprotease). EVP are not released by an exosomes-like (derived from MVB) or microvesicle-like (derived from the plasma membrane) mechanism, more preferably the EVP are released by a distinct mechanism described and demonstrated in detail in Muratori et al. Cell Host Microbe. 2009; 6(3):218-30). Muratori et al. could show that for example, the HIV-Nef-induced EVP-release mechanism resembled a budding-like process, which occurred very often at the site of microvilli formation and protrusions. First, small vesicles were seemingly transported from the cytoplasm to the plasma membrane (PM) and bulged the PM into a ball-like structure. Then the PM apparently ruptured and released the EVP eventually leaving an empty membrane compartment behind. Surprisingly, the released EVP remained coherent in clusters and attached in whole complexes to cell surfaces of bystander cells. Thus, that the Nef-induced generation of EVP differed from previously described mechanism.

Measuring the enzymatic activity of at least one disease-associated protease in extracellular vesicles in the sample can be performed directly within the extracellular vesicle, that is without disrupting/lysing the extracellular vesicle. Alternately the extracellular vesicle can be disrupted prior to measuring the enzymatic activity of at least one disease-associated protease. Preferably, measuring of the enzymatic activity is performed directly within the extracellular vesicle, without disrupting/lysing the extracellular vesicle and without disrupting/lysing the physiological setting of the protease, which otherwise is potentially activated non-specifically, e.g. by disruption of the protease-associated signaling complex in the vesicle membrane.

The sample provided from a patient can be any sample, preferably a sample obtained from a body fluid, like plasma, serum, urine, saliva, and/or other body fluids, and/or a sample obtained from extracellular supernatants. More preferably the probe is a plasma probe.

The term patient as used within the present application refers to any recipient of health care services. The recipient can be any living being, preferably a human or animal, most preferable a human. The patient can be ill or injured and in need of treatment by a physician, veterinarian, or other health care provider. But the patient can also be a healthy patient, like pregnant women, live organ donor, blood donors, newborns, recipients of preventive services and screening tests, occupational medical checkups, children's screening, dental screening examination, prenatal care or patients who undergo medically not indicated plastic surgery.

The term disease as used within the present application refers to any abnormal condition that affects the body of an organism at the time the sample is taken or in the future thereof. The term disease broadly refers to any condition that impairs or threatens normal function, and is therefore associated with dysfunction of normal homeostasis. The disease can be any infectious disease, which is a clinically evident disease that results from the presence of pathogenic microbial agents, including viruses, bacteria, fungi, protozoa, multicellular organisms, and aberrant proteins known as prions. The disease can be any non-infectious disease, including most forms of cancer, heart disease, and genetic disease. The disease can further be a disease associated with chronic inflammation, including autoimmune and neurodegenerative diseases.

Preferable the disease is a viral infection, cancer, and/or a disease associated with chronic inflammation.

Viral infection is an infection on the basis of patients harboring a virus that contains a DNA or RNA genome (i.e. DNA- or RNA-viruses) typically detected by host cellular nucleic acid sensing systems, as for example the Toll-like (TLR) receptors. Preferably the viral infection is a chronic infection caused for example by HIV virus, another retrovirus like human T-lymphotropic virus type 1 (HTLV1), one of the herpesviruses, pyolyomaviruses or papillomaviruses, or a hepatitis virus, such HBV or HCV. Alternatively, the viral infection may be less chronic in nature, and caused for example by adenoviruses, coronaviruses, picornaviruses, paramyxoviruses, orthomyxoviruses, bunyaviruses, caliciviruses, astroviruses, hepeviruses, rhabdoviruses, flaviviruses, parvoviruses, anelloviruses, togaviruses, bornaviruses, poxviruses, arenaviruses, or filoviruses. More preferably the viral infection is an HIV infection.

In a further preferred aspect of the present invention the disease is the reactivation of human endogenous retroviruses (HERV) characterized by the secretion of HERV RNA in or without vesicles detected by host cellular nucleic acid sensing systems, as for example the TLR receptors.

Preferably the cancer is a melanoma, a glioblastoma, breast cancer, prostate cancer, kidney cancer, lung cancer, oesophagus cancer, and/or gastrointestinal cancer. More preferably the cancer is a melanoma.

The disease associated with chronic inflammation is preferably an autoimmune disease and/or a neurodegenerative disease. Preferred autoimmune diseases are lupus erythematosus, scleroderma, and/or rheumatoid arthritis. Preferred neurodegenerative diseases are Alzheimer's disease, Parkinson's disease, and/or Multiple Sclerosis.

Preferably the disease-status is characterized by the reactivation of human endogenous retroviruses (HERV).

The method comprises a step of detecting at least one disease-associated protease. The disease-associated protease can be any protease which occurrence in extracellular vesicles is linked to a disease. Preferably the disease-associated protease is a matrixmetalloprotease (MMP), more preferably an ADAM-protease (A Disintegrin And Metalloproteinase). Preferred matrixmetalloproteases are MMP2, MMP5 and/or MMP9. Preferred ADAM-proteases are ADAM10, ADAM17, ADAM9 and/or ADAM5, more preferably ADAM10 and/or ADAM17.

ADAM 10 activity in EV is preferably a marker for cancer and more preferably for melanoma Thus, if the specific protease is ADAM10 then the disease is preferably cancer and more preferably melanoma.

ADAM 17 is preferably a marker for active and/or latent HIV activity. Thus, if the disease-associated protease is ADAM17 then the disease is preferably a HIV infection.

In a preferred embodiment of the present invention protease-containing extracellular vesicles are enriched and/or purified within the probe prior to measuring enzymatic activity of the at least one disease-associated protease in extracellular vesicles. The enrichment and/or purification of the proteinase-containing extracellular vesicles can preferably be performed by antibody-based methods and/or by non-antibody-based methods, more preferably the enrichment and/or purification is performed by antibody-based methods.

The enrichment and/or purification of the proteinase-containing extracellular vesicles by antibody-based methods can preferably performed by antibody-coupled beads or antibody-coated plates.

For an enrichment and/or purification using antibody-coupled beads, beads, preferably magnetic beads, are coated with antibodies that bind specifically to antigens on the surface of the proteinase-containing extracellular vesicles. Such antigens are for example activated integrins as for example alpha4beta1 (known to associate with ADAM proteases), or, for example, the specific protease itself (e.g. ADAM17). Alternatively, the assay may be performed in non-specific enrichments of EV either using antibodies directed against conventional antigens found on many vesicles (such as CD63).

A corresponding enrichment and/or purification can be performed using antibody-coated plates, based on plates that are coated with antibodies that bind specifically to antigens on the surface of the proteinase-containing extracellular vesicles.

Alternatively non-antibody-based methods can be used for the enrichment and/or purification of the proteinase-containing extracellular vesicles. These methods precipitate vesicles from a given fluid sample. Such non-antibody-based methods, which are suitable to isolate extracellular vesicles from fluids, and the reagents needed therefor are commercially available e.g. from System Biosciences (SBI) sold under the product name "ExoQuick" or from Life Technologies sold under the product name "exosome isolation reagent".

Enrichment and/or purification of the proteinase-containing extracellular vesicles further increases the sensitivity of the detection by reducing the noise background of the assay as body fluids, like for example plasma, contain many active proteases that would cleave the substrate peptide non-specifically. A physical separation (enrichment) of EV from the rest of the body fluid is therefore preferably performed prior to the measurement of the enzymatic activity of the at least one disease-associated protease in extracellular vesicles.

In a preferred embodiment the disease-associated protease is detected using a specific peptide that serves as a substrate for the disease-associated protease. By using a specific peptide that serves as a substrate for the disease-associated protease, it is possible to measure the activity of the disease-associated protease in the extracellular vesicles. Assessment of enzyme activity is at least 10 to 100 times more sensitive than just detecting a secreted protein.

The length of the specific peptide is not restricted. However, preferably the specific peptide is a protease-sensitive peptide comprising 5-50, more preferably 6-30, even more preferably 7-25, most preferably 8-20 amino acids, even most preferably 8-15 amino acids.

As specific peptide for the disease-associated protease, preferably a peptide comprising a sequence having at least 50% sequence identity to SEQ ID NO: 1 (RSSSRVAQAL), a peptide comprises a sequence having at least 50% sequence identity to SEQ ID NO: 2 (KSKQAMQDGH), and/or a peptide comprises a sequence having at least 50% sequence identity to SEQ ID NO: 3 (RALGLPK) is used.

More preferably a peptide comprising a sequence having at least 70% sequence identity to SEQ ID NO: 1 (RSSSRVAQAL), a peptide comprises a sequence having at least 70% sequence identity to SEQ ID NO: 2 (KSKQAMQDGH), and/or a peptide comprises a sequence having at least 70% sequence identity to SEQ ID NO: 3 (RALGLPK) is used.

Even more preferably a peptide comprising a sequence having at least 80% sequence identity to SEQ ID NO: 1 (RSSSRVAQAL), a peptide comprises a sequence having at least 80% sequence identity to SEQ ID NO: 2 (KSKQAMQDGH), and/or a peptide comprises a sequence having at least 80% sequence identity to SEQ ID NO: 3 (RALGLPK) is used.

Most preferably a peptide comprising a sequence having at least 90% sequence identity to SEQ ID NO: 1 (RSSSRVAQAL), a peptide comprises a sequence having at least 90% sequence identity to SEQ ID NO: 2 (KSKQAMQDGH), and/or a peptide comprises a sequence having at least 90% sequence identity to SEQ ID NO: 3 (RALGLPK) is used.

A peptide comprising a sequence having preferably at least 50%, more preferably at least 70%, even more preferably at least 80%, most preferably at least 90% sequence identity to SEQ ID NO: 1 (RSSSRVAQAL), is preferably a specific peptide substrate for ADAM17.

A peptide comprising a sequence having preferably at least 50%, more preferably at least 70%, even more preferably at least 80%, most preferably at least 90% sequence identity to SEQ ID NO: 2 (KSKQAMQDGH), is preferably a specific peptide substrate for ADAM10.

A peptide comprising a sequence having preferably at least 50%, more preferably at least 70%, even more preferably at least 80%, most preferably at least 90% sequence identity to SEQ ID NO: 3 (RALGLPK), is preferably a broad substrate for collagenases and ADAM proteases.

Preferably the specific peptide that serves as a substrate for the protease is modified with chemical groups that enable to detect the proteolytic cleavage of the specific peptide based on Forster resonance energy transfer (FRET), more preferably the peptide is modified with at least one fluorophore and at least one quencher moiety, wherein the protease-specific cleavage site of the peptide is located between the fluorophore and the quencher moiety. FRET peptides are labelled with two fluorophores. FRET describes the transfer of energy from an initially excited donor (fluorophore 1) to an acceptor (fluorophore 2). Typically, this donor emits light at a wavelength λd that overlaps with the absorption wavelength λa of the acceptor. If donor and acceptor fluorophore are in close proximity (10-100 Å), this energy transfer happens in one of two ways, depending on the chemical structure of the acceptor: a) the transferred energy is converted to molecular vibrations (acceptor is dark quencher) b) the transferred energy is emitted as light with a longer wavelength (acceptor is fluorescent) If the two fluorophores are separated from another (e.g. by protease cleavage of peptide), fluorescent signals are generated. These signals differ depending on the fluorescent characteristics of the fluorophore pair.

The distance dependence of FRET makes FRET peptides a useful tool for investigation of biological studies where evaluation of proximity is important. If donor fluorescence is quenched, it indicates that both donor and acceptor molecule are close (approx. 10-100 Å). If donor fluorescence can be detected, the molecules are more distant. FRET peptides are used as suitable substrates in enzyme studies, such as:

functional characterization of peptidases/proteases
kinetic characterization of peptidases/proteases
screening and detection of new proteolytic enzymes.

The enzyme activity is measured by any UV-based conventional fluorophore-detecting multi-well plate reader. For additional sensitivity time-resolved FRET (TR-FRET) can also be used. In this case the exceptionally long lifetime of fluorescence emitted by certain compounds, such as lanthanide chelates, is exploited by measuring the emission following a delay after the excitation to improve the signal-to-noise ratio of the measurement. Most modern fluorescence plate readers can be also used for TR-FRET.

Preferably the specific peptide that serves as a substrate for the specific protease comprises chemical or amino acid modifications for translocation of the peptide into the EV.

Such modification can be lipophilic fluorophore and quencher moieties which show a high membrane translocation potential.

The present invention further relates to modified peptides which can be used for the in vitro detection of a protease in extracellular vesicles, more preferably the modified peptides can be used in the method for in vitro detection and/or monitoring of a disease in a sample described above.

The modified peptide is obtained by combining a protease-sensitive peptide comprising preferably 5-50, more preferably 6-30, even more preferably 7-25, most preferably 8-20 amino acids, even most preferably 8-15 amino acids with a fluorophore-modification and a quencher-modification, which allows an easy detection using Forster Resonance Energy Transfer (FRET). The lipophilic fluorophore 5-FAM (5-carboxyfluorescein) and the Quencher QXL™ 520 from AnaSpec are prototyes of such lipophilic fluorophores. For increased assay sensitivity and improved signal-to-noise ratio time-resolved FRET (TR-FRET) can be adopted for example by using a luminescent lanthanide, such as europium chelate, as the fluorophore.

Preferably, the protease-specific cleavage site of the peptide is located between the fluorophore-modification and the quencher-modification, and more preferably the fluorophore- and the quencher-modification are located within a distance of 10-100 Å to allow sufficient quenching.

Preferably the fluorophore-modification is lipophilic. By using a lipophilic fluorophore modification the translocation of the modified peptide into the vesicle is promoted and preferably the lipophilic fluorophore modification enables the translocation of the peptide into the vesicle without any further modifications of the peptide.

However, also other, non-lipophilic, modification may penetrate membranes, or, alternatively, vesicle membranes may be lysed in the course of the assay.

In a further preferred embodiment the specific peptide is a modified peptide obtained by combining a protease-sensitive peptide comprising preferably 5-50, more preferably 6-30, even more preferably 7-25, most preferably 8-20 amino acids, even most preferably 8-15 amino acids with an N- and/or C-terminal sequence comprising preferably 5-20, more preferably 6-18, even more preferably 7-16, most preferably 8-16 membrane penetrating amino acids with a fluorophore-modification and a quencher-modification, wherein the protease-specific cleavage site of the peptide is located between the fluorophore-modification and the quencher-modification.

Preferably the N- and/or C-terminal sequence comprises a sequence having at least 80% sequence identity to SEQ ID NO: 4 (KKWKMRRNQFWIKIQR) corresponding to the sequence of Penetratin, a 16 residue peptide, a sequence having at least 80% sequence identity to SEQ ID NO: 5 (GRKKRRQRRRPPQ) corresponding to the 13-amino-acid peptide encompassing the basic domain of HIV Tat (Tat 48-60), and/or an arginine-rich sequence comprising 8-12 arginines (SEQ ID NO:6-10).

More preferably the N- and/or C-terminal sequence comprises a sequence having at least 90% sequence identity to SEQ ID NO: 4 (KKWKMRRNQFWIKIQR) corresponding to the sequence of Penetratin, a 16 residue peptide, a sequence having at least 90% sequence identity to SEQ ID NO: 5 (GRKKRRQRRRPPQ) corresponding to the 13-amino-acid peptide encompassing the basic domain of HIV Tat (Tat 48-60), and/or an arginine-rich sequence comprising 8-12 arginines (SEQ ID NO:6-10).

If the membrane penetrating amino acids are located at the C-terminal end of the modified peptide then the quencher is preferably located C-terminal of the protease-specific cleavage site of the peptide and the fluorophore is preferably located N-terminal of the protease-specific cleavage site of the peptide. However, if the membrane penetrating amino acids are located at the N-terminal end then the quencher is preferably located N-terminal of the protease-specific cleavage site of the peptide and the fluorophore is preferably located C-terminal of the protease-specific cleavage site of the peptide.

This arrangement of the fluorophore and the quencher allows the peptide-fragment containing the quencher to leave the extracellular vesicle after cleavage of the peptide by the protease, while the fragment containing the fluorophore will remain within the vesicle. This allows an easy measurement of enzyme activity based on the fluorescence of the vesicles.

By using an an N- and/or C-terminal sequence comprising membrane penetrating amino acids the translocation of the modified peptide into the vesicle is promoted and preferably the N- and/or C-terminal amino acid modification enables the translocation of the peptide into the vesicle.

The present invention further relates to a kit comprising a modified peptides a described above. More preferably such a kit can be used for the in vitro detection of a protease in extracellular vesicles, more preferably the modified peptides can be used in the method for in vitro detection and/or monitoring of a disease in a sample described above.

Furthermore, from the above disclosure it is comprehensible that the measurement of ADAM-protease activity can be used as an in vitro marker of tumor activity and/or the presence of tumor cells. Preferably the activity of ADAM-protease is measured within extracellular vesicles.

EXAMPLES

Within this invention it is demonstrated that the Nef protein of HIV induces the activation of ADAM17 and 10 proteases as well as their uploading into extracellular vesicles (EV). A similar mechanism is presented for melanoma cells. The inventors found that all melanoma cells activate ADAM10 and shed the protease into EV. For in vivo evidence they showed, that all HIV-infected individuals analyzed (16 individuals), whether HAART-treated or not and whether viremic or not, harbored high levels of ADAM-containing EV in plasma. A similar observation was made with plasma from melanoma patients (31 individuals analyzed).

EVP Purification from Patient Samples

For EVP-purification from patient samples, 5 ml blood plasma was diluted with 5 ml PBS and centrifuged for 30 min at 2000 g, 45 min at 12000 g and ultra-centrifuged for 2 h at 110,000 g. Pellets were resuspended in 45 µl of loading buffer and all of the EVP lysate was subsequently analyzed by immunoblot. Alternatively the pellet was resuspended in protease assay buffer and an aliquot thereof was used to assess ADAM17/10 enzymatic activity.

Measuring ADAM17/10 Enzymatic Activity

EVP-associated ADAM17/10 activity was measured in a 500 µL cell culture supernatant by an in vitro enzymatic assay adding a FRET peptide substrate: Glu(Edans)-LAQAVRSSS-Lys(Dabcyl) for up to 180 minutes and analyzed by an UV-light based ELISA Reader. Using the more lipophilic fluorophore 5-FAM (5-carboxyfluorescein) and the Quencher QXL™ 520 from AnaSpec increased the sensitivity of the assay (SensoLyte®520 TACE (α-Secretase) Activity Assay Kit, AnaSpec, Inc., Fremont, Calif.) (FIG. 10A). Unexpectedly, the inventors noted that 5-FAM could alone provide a sufficiently lipophilic character to the peptide to mediate it transfer across the EV membrane, and disruption/lysis of the EVP was no longer necessary, and rather decreased the readout of the assay. Thus, peptide substrates modified with lipophilic moieties (Fluorophore, Quencher) were able to penetrate the EVP membrane reaching the protease catalytic center within the EVP. These results are in agreement with the experimental observations showing that activated ADAM proteases have an upside-down orientation.

The activity of the test was further increased when EVP were enriched prior to addition of the FRET peptide, as for example by ultracentrifugation. Alternatively, antibody-coupled beads or antibody-coated ELISA-plates were used, which were specifically developed to enrich EVP (FIG. 10B). The enrichment procedure is of relevance when low levels of EVP are expected, as for example in cancer patients with low tumor mass or in the follow-up of cancer treatment.

In the course of these observation the inventors also found, that EV harbor activated ADAM proteases in an upside down fashion (FIG. 11), placing the catalytic protease center within the vesicle. The first evidence for this orientation was found when N-terminal cleavage products of the proteases were detected within EV. These findings were confirmed when monoclonal antibodies directed against the C-terminus of ADAM17 (usually intracellular) recognized/stained EVP in a FACS analysis. Conversely, antibodies directed against the N terminus could not detect these EV (FIG. 12). As these EV define a separate subclass with respect to release mechanism, receptor surface composition and ADAM proteases orientation, they were termed EVP (Extracellular Vesicles containing Proteases).

FACS-Analysis of EVP Demonstrating the Upside-Down Orientation of ADAM17

Monoclonal antibodies were raised against the C-terminus of ADAM17 (peptide sequence: KLQRQNRVD-SKETEC) (SEQ ID NO 11). Hybridomas that were obtained were tested if they could stain the EVP by FACS analysis. FACS analysis of bead-coupled EV was performed as previously described (Thery et al., 2006; Muratori et al., 2009). Briefly, 6 μg EV prepared from cell culture supernatants were incubated with 10 μl of 3.9-μm diameter latex beads surfactant-free aldehyde/sulfate (Invitrogen, A37304) in a final volume of 15-20 it for 15 min at room temperature. To each sample 1 ml PBS was added and incubated overnight at 4° C. 110 μl of PBS/1 M glycine was added to each sample followed by incubation for 30 min at room temperature. EV-coated beads were washed 3 times in PBS/0.5% (w/v) BSA and resuspended in 500 μl PBS/0.5% (w/v) BSA. 10 μl EV-coated beads were incubated with 50 μl antibody diluted in PBS/0.5% BSA for 30 min at 4° C., followed when necessary by incubation with a PE or FITC-conjugated antibody, and analyzed by FACS. Two clones (2C6; 1E2) stained EVP (red arrows) similar as the positive controls (CD63, CD81). Conversely an antibody directed against the N-terminus of ADAM17 was negative (TACE). The insert (Western blot) shows that both antibodies (2C6, 1E2) recognize the activated form of ADAM17.

Thus, the inventors showed that ADAM-loaded EVP appear in the periphery/blood of HIV and cancer patients at highly elevated levels. It is likely that the same will be observed in other chronic infections, diseases and cancers. The ADAM-activity in plasma can be assessed using specific substrate peptides and an enzymatic in vitro assay. The upside-down orientation of the ADAM active catalytic domain allows taking advantage of membrane penetrating peptides in a matter that does not require the disruption/lysis of EV and potentially even EV purification from plasma. The sensitivity of the enzymatic activity is greatly enhanced by purifying EV using antibody-coupled beads or antibody-coated ELISA plates.

The present inventors discovered that activated (ADAM) proteases are surprisingly and unexpected incorporated into EV in an upside down membrane orientation, that is the protease active N-terminus is located inside the EV. This observation is in contrast to all known knowledge regarding the incorporation of proteases into vesicles.

The inventors further showed that the use of substrate FRET peptides that penetrate the EV membrane can provide a simple and fast method to bring the substrate peptide in close proximity to the active protease site, thus ensuring a high substrate turnover. Membrane penetration and accumulation can be achieved by using a polyarginine stretch or a lipophilic chemical modification at either end of the FRET peptide (FIG. 11). Ideally, the fluorophore involved in providing the FRET signal can also serve as the lipophilic modification that allows the peptide to penetrate the EV membrane. By this principle any active protease may be measured using suitable peptide substrates in plasma and cell culture supernatant either with or without EV-purification or EV disruption/lysis.

Figure 8:
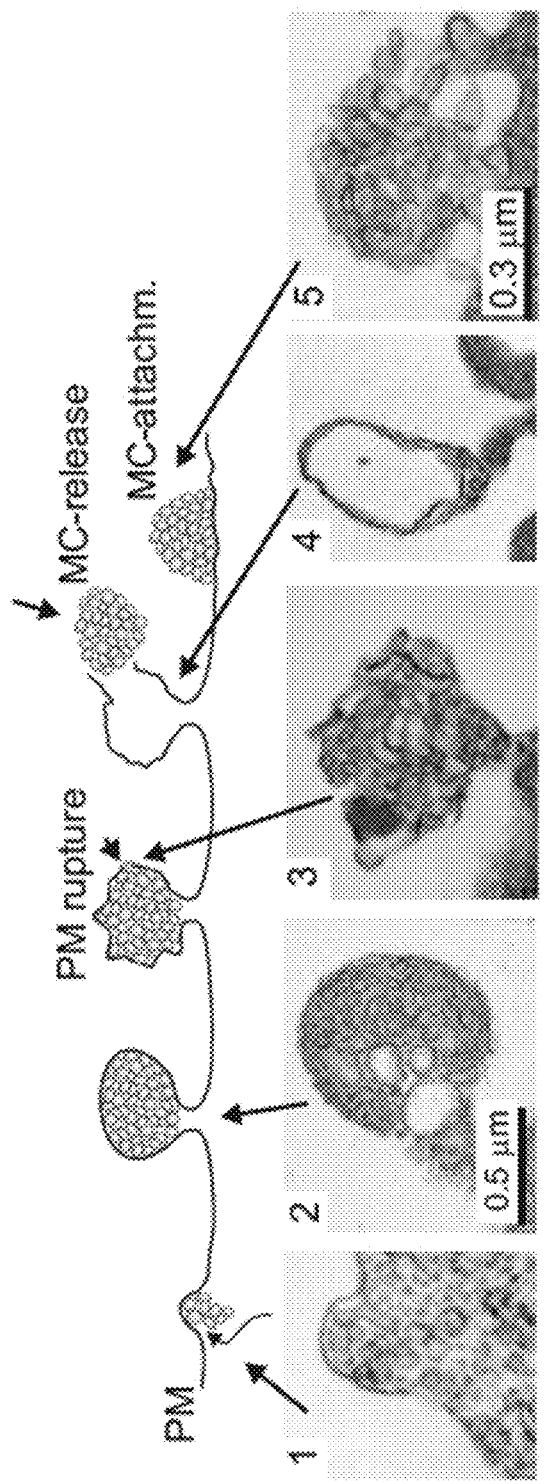
FIG. 8: HIV-Nef-induced exocytosis leads to the secretion of extracellular vesicle (EV) clusters at the plasma membrane of T cells. (1-5) Subsequent stages of EV-cluster generation and release as described in the text. First, small vesicles were seemingly transported from the cytoplasm to the plasma membrane and bulged the plasma membrane into a ball-like structure (1-2). Then the plasma membrane apparently ruptured (3) and released the EV-cluster eventually leaving an empty membrane compartment behind (4). The released EV-clusters remained coherent and attached in whole complexes to cell surfaces of bystander cells (5).

In 2009 some of the inventors published a yet not described mode of vesicle release (Muratori et al. 2009) and characterized this mechanism in great detail by electron microscopy. Now the inventors discovered that these vesicles contain active ADAM proteases. In this new mechanism vesicles of similar size first accumulate under the outer plasma membrane and gradually form a ball-like structure, which subsequently ruptures and releases the vesicles into extracellular space (FIG. 8). The inventors now further discovered that these vesicles, aside from their release mode, differ additionally from known extracellular vesicles like Exosomes by the following criteria:

1) They do not express CD81
2) Contrary to published results and assumptions, some of their membrane proteins, including the ADAM proteases, were inserted into the vesicle membrane in an invert (flipped) orientation, meaning their extracellular domain, in the case of ADAM proteases containing the enzymatic active center, resides in the lumen of the vesicle.

Taken these facts together, the inventors found that ADAM-containing extracellular vesicles differ considerably from exosomes and other known extracellular vesicles and hence form a distinct subclass of EV. Thus, these vesicles were termed "extracellular vesicles containing proteases" (EVP).

Measurement of enzymatic activity of ADAM proteases in EV in probes from HIV patients Western blot (FIG. 13A), performed by standard procedures, of plasma EV from HIV patients and controls for the presence of ADAM17, ADAM10, Nef and control proteins. In general 20 μg of cellular protein lysate and 10 μg of microvesicle lysate were loaded per lane. The blots were incubated with commercial available antibodies as indicated. The monoclonal antibodie α-Tsg101 was purchased from Santa Cruz; α-paxillin (clone 5H11) form Millipore; α-ADAM10, α-ADAM17, α-Gag and α-Nef from Abcam; α-HLA from Pharmingen. For EV purification from patient samples, 5 ml blood plasma was diluted with 5 ml PBS and centrifuged for 30 min at 2000 g, 45 min at 12000 g and ultra-centrifuged for 2 h at 110,000 g. Pellets were resuspended in 1 ml PBS and 40 μl of antibody-coupled MicroBeads were added for 1 h and subsequently subjected to magnetic immunoisolation with MACS® Technology (Miltenyi Biotech, Bergisch Gladbach, Germany) using MS columns. The EV were finally eluted with 45 μl of hot (95° C.) loading buffer and all of the vesicle lysate was subsequently analyzed by western blot.

EV-associated ADAM17 enzymatic activity (FIG. 13B) was measured by FRET substrate cleavage by EV isolated from 0.5 ml plasma of one HIV patients and two controls. EV were purified as described above. TACE activity was measured using the SensoLyte®520 TACE (α-Secretase) Activity Assay Kit from AnaSpec, according to the manufacturer's procedures.

The present inventors demonstrated that the Nef protein of HIV induces the activation of ADAM17 and ADAM10 proteases as well as their uploading into extracellular vesicles. The presence of ADAM proteases and the presence of Nef was demonstrated in EV purified from cell culture supernatant and plasma of non-viremic/HAART-treated infected individuals (100%; 11/11 individuals). The latter was done by Western blot, micro-RNA array and measurement of the enzymatic activity of ADAM17 and ADAM10. None of the non-infected controls (7 individuals) gave a positive result. The presence of ADAM 17 correlated inversely with a level of CD4 and CD8 cells in peripheral blood.

Measurement of Enzymatic Activity of ADAM Proteases in EV in Probes from Melanoma Patients Western blot (FIG. 14A) of plasma EV from melanoma patients and controls for the presence of ADAM10 and control proteins. For experimental details see above (Measurement of enzymatic activity of ADAM proteases in EV in probes from HIV patients and FIG. 13A).

EV-associated ADAM10 enzymatic activity (FIG. 14B) measured by FRET substrate cleavage in 0.5 ml plasma of one melanoma patient and one control. For experimental details above (Measurement of enzymatic activity of ADAM proteases in EV in probes from HIV patients and FIG. 13B).

The inventors demonstrated the presence of ADAM10 in plasma EV of melanoma patients by Western blot and ADAM10 enzymatic activity. The Western blot signal correlated with tumor mass. Furthermore, they demonstrated that almost 100% of 31 melanoma cell lines (30/31) express activated ADAM10 that is secreted into EV. Hence, active and secreted ADAM10 is a hallmark of melanoma tumor growth.

When looking for the cellular source that sheds ADAM-loaded vesicles in the human body, the inventors found that only maturing/mature and or activated dendritic cells release vesicles with activated ADAM17. EV derived from immature dendritic cells, monocytes and macrophages did not bear the active form of ADAM17.

In addition the inventors found that all HIV (including HAART-treated individuals) and all melanoma patients with tumor mass that we have examined revealed the presence of active and measurable ADAM proteases in plasma. These active ADAM proteases reside in unique extracellular vesicles (EVP) that differ from vesicles defined as exosomes based on their mode of release, surface marker composition, and the predominant flipped orientation of their transmembrane proteins, such as ADAMs. These vesicles are predominantly shed by the tumor itself and, in the case of melanoma, contain ADAM10. In the case of HIV they are predominantly shed by maturing dendritic cells. Importantly, EVPs or activated ADAMs were not detected in sera collected from healthy control individuals.

In summary the inventors found out that measuring the activity of activated ADAM proteases in body fluids is a sensitive, easy to perform, and reliable procedure to assess the activity of hidden viral reservoirs (HIV and other viral infections), malignant processes and dendritic cells, as all of these cells shed EVP in vitro and in vivo. Body fluids from healthy individuals had only background activity.

The present inventors have delineated the molecular mechanism that leads to the uploading of ADAM proteases into a distinct subclass termed Extracellular Vesicles containing Proteases (EVP). EVP differ from other EVs described so far, such as exosomes, based on their mechanism of cellular release, their receptor composition and the orientation of their membrane markers, including the active ADAM proteases. They discovered that ADAM proteases are secreted in their active form into EVP and hence can be measured using an enzymatic assay. They found that this enzymatic activity is particularly high in HIV and melanoma patients, and correlates with their disease state and tumor size, respectively. The results show that other cancers, infectious diseases and diseases with acute or chronic immune activation are likely to give similar results. For example, an elevated ADAM activity was detected in a negative/healthy control. Subsequent clinical analysis revealed that this individual suffered from an early form of. oesophagus cancer. In addition, the inventors discovered that maturing dendritic cells (DC) also secrete EVP that contain activated ADAM proteases.

Experimental Procedures

Cell lines, Antibodies and Recombinant proteins. Melanoma cell lines were generated from fresh tumor biopsies obtained directly after surgery. A single cell suspension was produced by mechanical dissociation and enzymatic digestion with DNAse and collagenase. Cells were seeded in RPMI supplemented with 20% human serum into 6-well plates. Passaging of cells was performed according to cell density. Melanocytes were purchased from Promocell (Heidelberg) and cultured in Melanocyte Growth Medium provided by the same supplier (Promocell) at 37° C., 5% $CO_2$. Antibody suppliers: Covance: α-myc (9E11), α-AU-1 and α-HA; Santa Cruz: α-hnRNP-K (D-6), α-Lck (3A5), α-PKC5 (C17), α-Tsg101 (c-2); Cell Signaling: α-phospho-PAK1 (Ser199/204)/PAK2 (Ser192/197), α-PAK1, α-PAK2, α-Erk and α-phospho-Erk (Thr202/204); Millipore: α-phospho-paxillin (Y118), α-paxillin (5H11); Abcam: α-Nef (JR6), α-ADAM10 and α-ADAM17; BD Transduction Laboratories: α-Transferrin receptor; DAKO: anti-HLA-A, B, C (G46-2.6), BD PharMingen: anti-CD63, anti-CD9, anti-CD81; BAbCO: anti-AU-1.

Plasmids. The CD8-Nef fusion proteins as well as Nef-AU1 were described previously (Baur et al., 1997). Pak1, 2 expression plasmids and mutants (PAK1R: aa1-225; Pak2K278R, Pak1L107F, Pak2L106F) were described in (Renkema et al., 2001; Manninen et al., 1998). The paxillin expression plasmids and mutants (PaxΔLD4) were described in (Tumbarello et al., 2002; Turner et al., 1999) and provided by Christopher Turner, Syracuse, USA. Paxillin phosphorylation mutants (Y118A, S258A, S272/4A, Y118/5272/4A, S272/4E) were generated by site directed mutagenesis using the QuikChange Lightning Mutagenesis Kit (Stratagene). Expression plasmids of TACE were provided by A. Pandiella, Salamanca, Spain and A. Ullrich, Munchen, Germany. The GFP-proTNF-RFP fusion protein was constructed by overlapping PCR technique.

Transfections into 293T cells and protein assays. Transient transfections into 293T cells as well as immunoprecipitations and immunoblots were performed as described previously (Baur et al., 1997; Witte et al., 2004; Wolf et al., 2008). In general 20 μg of cellular protein lysate and 10 μg of EV lysate were loaded per lane. The latter corresponded to the secretion from 2-4 mio 293T cells within 48 h. Endogenous TACE activity was measured using SensoLyte®520 TACE (α-Secretase) Activity Assay Kit from AnaSpec, according to the manufacturer's procedures. Cell lysates were generated from 293T cells 24 h after tranfection of Nef/mNAKC. Aliquots of transfected cells were treated with TAPI for 12 h prior to cell lysis.

Patients. Blood was drawn from patients after an informed consent, approved by the local ethics committee, was signed. At the time of blood sampling, both HIV-1 patients (HIV01, HIV02) were under HAART treatment, however showing low to intermediate levels of viral load (3900 and 23000 viral copies/ml blood). All five Melanoma patients were in clinical stage IV N2c. One patient had no tumor load whereas four of them had multiple but not extensive numbers of metastases in different organs including skin, liver, lung and lymph nodes.

Immunofluorescence, Confocal Microscopy and FACS analysis. Immunostainings were performed as described previously (Muratori et al., 2009). Slides were analyzed on LEICA TCS SP5 laser scanning microscope equipped with the LAS-AF software (Leica Microsystems, Mannheim, Germany). For FACS analysis, 105 cells were washed twice in FACS buffer before being analyzed using a FACSCalibur™ flow cytomer (BD Biosciences) and CELLQuest™ software (BD Biosciences).

Virus infections and transfections. HIV-1 molecular clones (NL4-3 WT and Δnef) were described previously (Schiavoni et al., 2004). For viral infections 105 HeLaCD4 cells were seeded/well in a 24 well plate and transfected (Lipofectamine) with 1 µg G-proTNF-R. 12 hours later cells were infected with 500 ng (per well in triplicates) of VSV-G pseudotyped HIV-particles by spinoculation. On day three each well was tested for both, TNFα and HIV expression (using an anti-gp120 mAb). Infection efficiency was 60-70% in both conditions and transfection efficiency was around 18% in infected and uninfected cells. TNFα analysis was assessed in gp120-positive cells. For viral transfections 293T cells were seeded at 105/well in a 24 well plate. On day-1 HIV-1 clones (WT and Δnef; 2 µg) or empty vector (2 µg) and GFP-proTNF-RFP (1 µg, 500, 250, or 125 ng) were transfected by Lipofectamine. On day-3 cells were detached with trypsin and analyzed by FACS. An aliquot of the cells were analyzed for p24 expression by FACS.

FACS analysis of EV. FACS analysis of bead-coupled EV was performed as previously described (Thery et al., 2006; Muratori et al., 2009). Briefly, microvesicles suspensions (6 µg) were incubated with 10 µl of latex beads (Invitrogen, A37304) for 15 min at room temperature. To each sample 1 ml PBS was added and incubated overnight at 4° C. 110 µl of PBS/1 M glycine was added to each sample followed by incubation for 30 min at room temperature. 10 µl EV-coated beads were incubated with 50 µl antibody diluted in PBS/ 0.5% BSA for 30 min at 4° C., followed when necessary by incubation with a PE or FITC-conjugated antibody, and analyzed by FACS.

Isolation and purification of EV. EV purification was performed as previously described (Muratori et al., 2009; Thery et al., 2006). Briefly, supernatants were collected after 48 h and centrifuged for 20 min at 2000 g, 30 min at 10,000 g and ultra-centrifuged for 1 h at 100,000 g. Pellets were resuspended in 35 ml PBS and centrifuged at 100,000 g for 1 h. Pellets were again resuspended in 100 µl PBS and considered as EV preparations. For further purification, EV were diluted in 2 ml of 2.5M sucrose, 20 mM Hepes/NaOH, pH 7.4 and a linear sucrose gradient (2-0.25 M sucrose, 20 mM Hepes/NaOH pH7.4) was layered on top of the EV suspension. The samples were then centrifuged at 210,000 g for 15 h. Gradient fractions were collected and the refractive index was determined. Each fraction was diluted in 10 ml PBS and ultra-centrifuged for 1 h at 110,000 g. Pellets were solubilized in SDS sample buffer and analyzed by SDS-PAGE and immunoblotting.

For EV purification from patient samples, 5 ml blood plasma was diluted with 5 ml PBS and centrifuged for 30 min at 2000 g, 45 min at 12000 g and ultra-centrifuged for 2 h at 110,000 g. Pellets were resuspended in 45 µl of loading buffer and all of the EV lysate was subsequently analyzed by immunoblot. For labeling of EV with PKH (FIG. 6D) we used the Sigma Mini26-1KT" PKH26 Red Fluorescent Cell Linker Mini Kit (Sigma) according to the manufacturers' procedures.

Isolation of lipid rafts via discontinuous sucrose density gradient. Transfected cells were lysed in ice-cold TXNE (1% Triton X-100, 50 mM Tris-HCl pH 7.4, 150 mM NaCl, 5 mM EDTA, protease inhibitors). Lysates was passed 10 times through a 23 gauge needle and centrifuged at 13000 rpm for 1 minute. The supernatant was transferred to ultracentrifuge tubes, mixed well with 2 ml 80% sucrose solution and overlayed with 4 ml 30% sucrose solution and 4 ml 5% sucrose solution. A discontinuous sucrose density gradient tube which included lysate was ultra-centrifuged (SW60 Ti rotor, 40.000 rpm, 4° C., 16 hours). Fractions of 400 µl were collected from the top of the gradient and analyzed by Dot blotting and Western Blotting.

PBMC stimulation with EV and measurement of Cytokine Secretion. PBMC ($1 \times 10^5$) were added to each well of a 96-well-U-bottom plate in a total volume of 200 µl (RPMI). 10 µl of exosome preparation from transfected cells (corresponding to $2 \times 10^6$ cells or one 10 cm dish) were added per well and incubated for 2 hours. When indicated 10 µl PHA (positive control), 50 µM TAPI-1 (Peptides International), or 10 µM U0126 (MAPK-Inhibitor, Promega) were used. Cytokines in the supernatant (200 µl) were measured via the CBA (Cytometric Bead Array) Human Soluble Protein Flex Set System (BD Biosciences).

Results

The inventors demonstrate that the integrin effector paxillin is part of the Nef signaling complex. In concert with Eed, Pak1 and Pak2, Paxillin served to recruit, activate and secrete TACE and ADAM10 via EV. Such vesicles were taken up by PBMC causing a rapid release of TNFα. Notably HIV-1 as well as melanoma cells induced the same signaling complex. Our report describes a mechanism by which pathogens and cancer cells may exploit regulated cytokine release for their own proliferation.

The HIV Nef protein recruits the polycomb protein Eed and mimics an integrin receptor signal for reasons that are not entirely clear. Here we demonstrate that Nef and Eed complex with the integrin effector paxillin to recruit and activate TNFα converting enzyme (TACE/ADAM17) and its close relative ADAM10. The activated proteases cleaved proTNFα and were shuttled into extracellular vesicles (EV). Peripheral blood mononuclear cells that ingested these EV released TNFα. Analyzing the mechanism the inventors found that Pak2, an established host cell effector of Nef, phosphorylated paxillin on Ser272/274 to induce TACE-paxillin association and shuttling into EV via lipid rafts. Conversely, Pak1 phosphorylated paxillin on Ser258, which inhibited TACE association and lipid raft transfer. Interestingly, melanoma cells used an identical mechanism to shuttle predominantly ADAM10 into EV. Thus, HIV-1 and cancer cells exploit a paxillin/integrin-controlled mechanism to release TACE/ADAM10-containing vesicles ensuring better proliferation/growth conditions in their microenvironment.

Nef and NAKC Activate and Secret TACE

Initially we asked whether the Nef signaling complex (NAKC) would induce extracellular vesicles (EV) that contain ADAM proteases (FIG. 1A), similar as seen in tumor-derived vesicles. In our previous work coexpression of a minimum of three NAKC factors (e.g. hnRNPK, PKC and Lck, hereafter referred as minimal NAKC or mNAKC), and more so a combination that included Nef, activated Erk1/2 and Lck (Wolf et al., 2008) (FIG. 1A, C, D). For most of the present study we coexpressed Nef with mNAKC factors (hnRNPK, PKCδ, Lck) in order to study the functional contribution of individual factors.

Figure 15A:
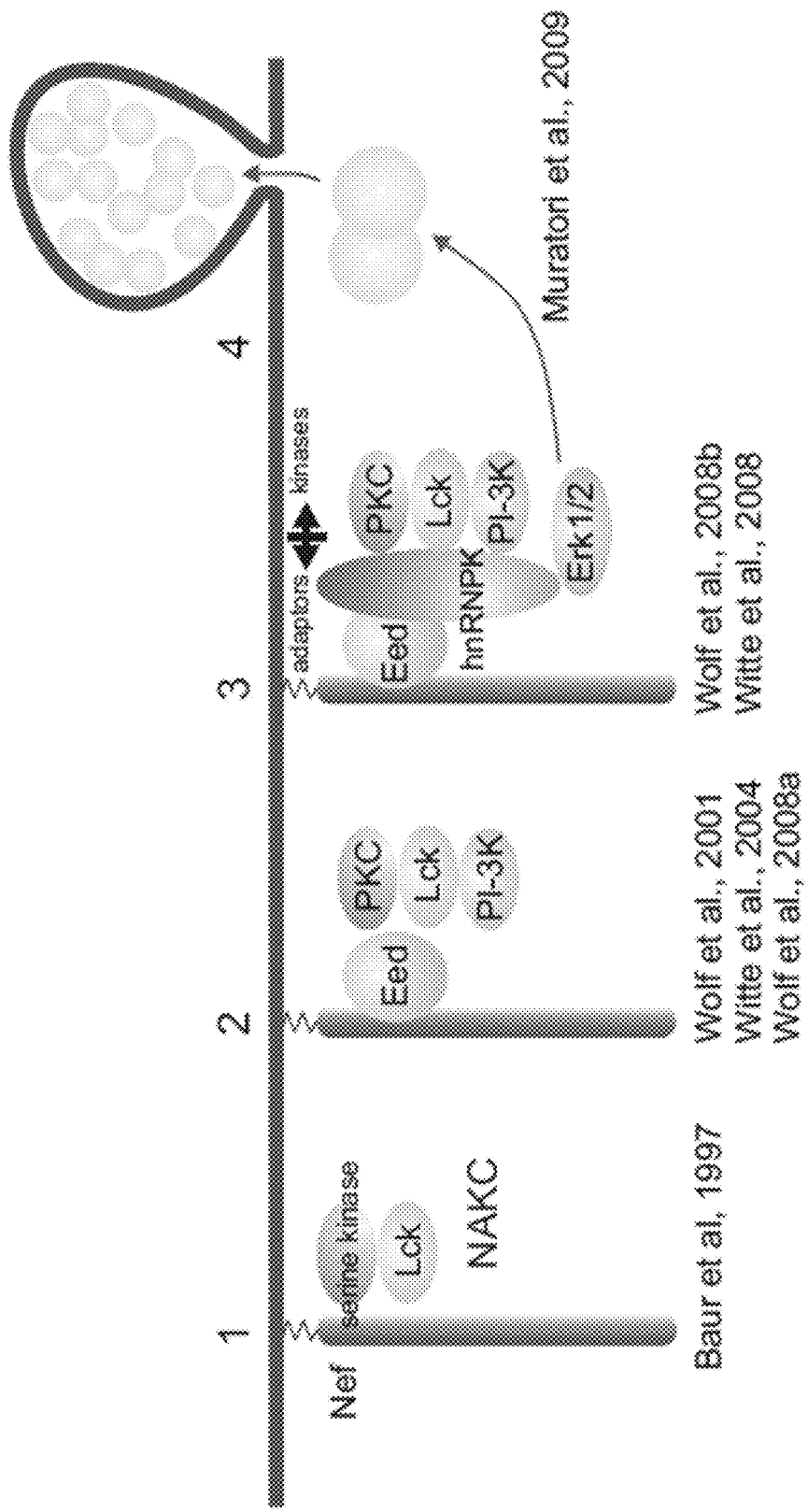
Figures 15B, 15C:
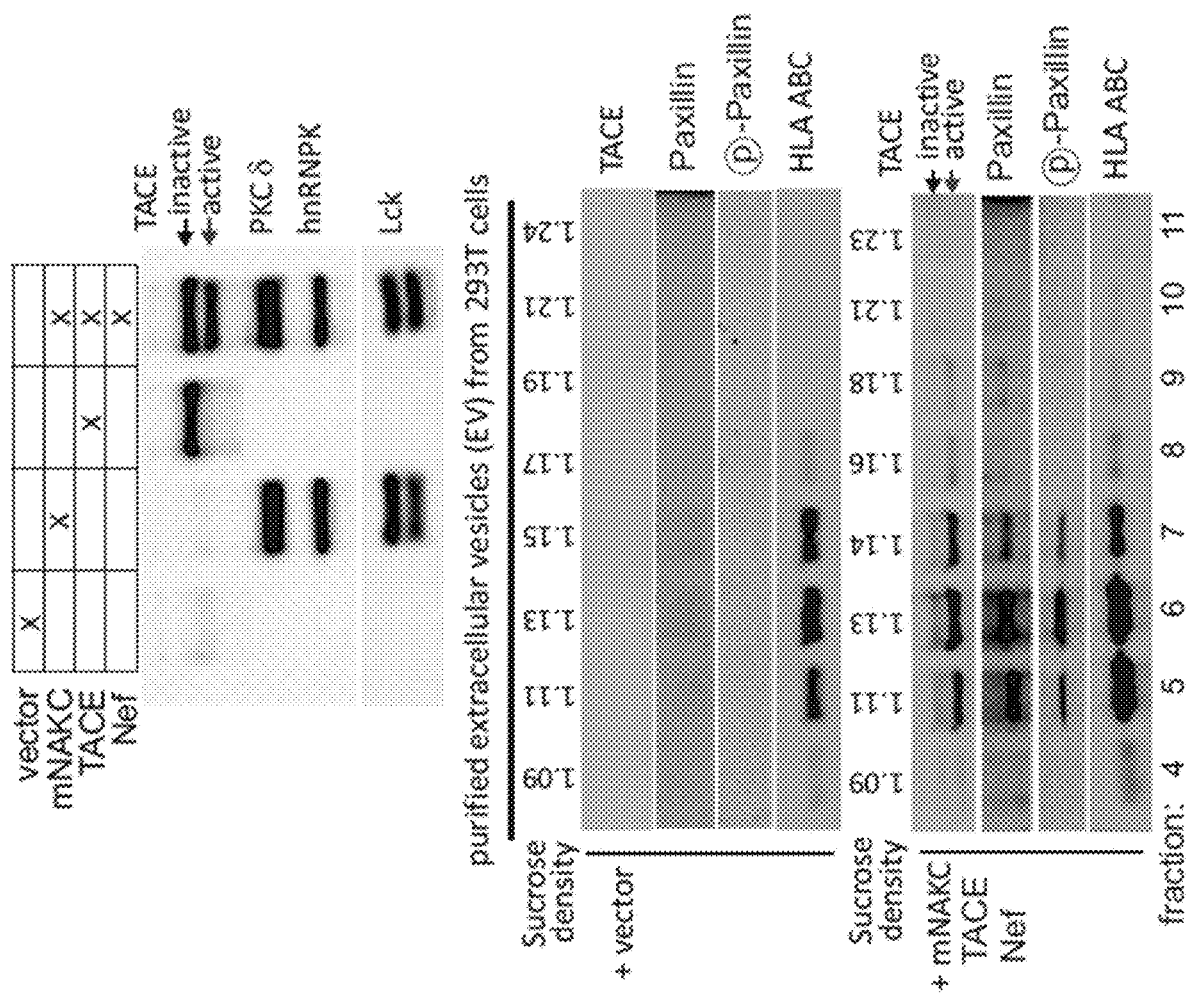

Nef, mNAKC and TACE (ADAM17) were transiently transfected into 293T cells and EV were purified from 10 ml culture supernatant by differential centrifugation. Vesicles were lysed and analyzed by immunoblot. In the presence of Nef and/or mNAKC endogenous as well as transfected TACE were transferred into EV (FIG. 1B, double arrows; expression controls in FIG. 15B). Notably, the activated form of TACE was present, evident by a faster migrating protein lacking the inhibitory N-terminal pro-domain (95 vs 135 kD; FIG. 1B, red arrow). The cleaved pro-domain was detected in the EV lysates as indicated. A sucrose gradient of EV preparations confirmed that foremost active TACE was transferred into floating vesicles (FIG. 15C). Of note, 293T cells secrete EV with the typical shape and size (80-120 nm), surface receptor composition (CD63, CD81, CD9 and HLA I), and floating properties in sucrose gradients as reported for microvesicles and exosomes (FIG. 15D-15F) (Thery et al., 2006).

Figure 16A:
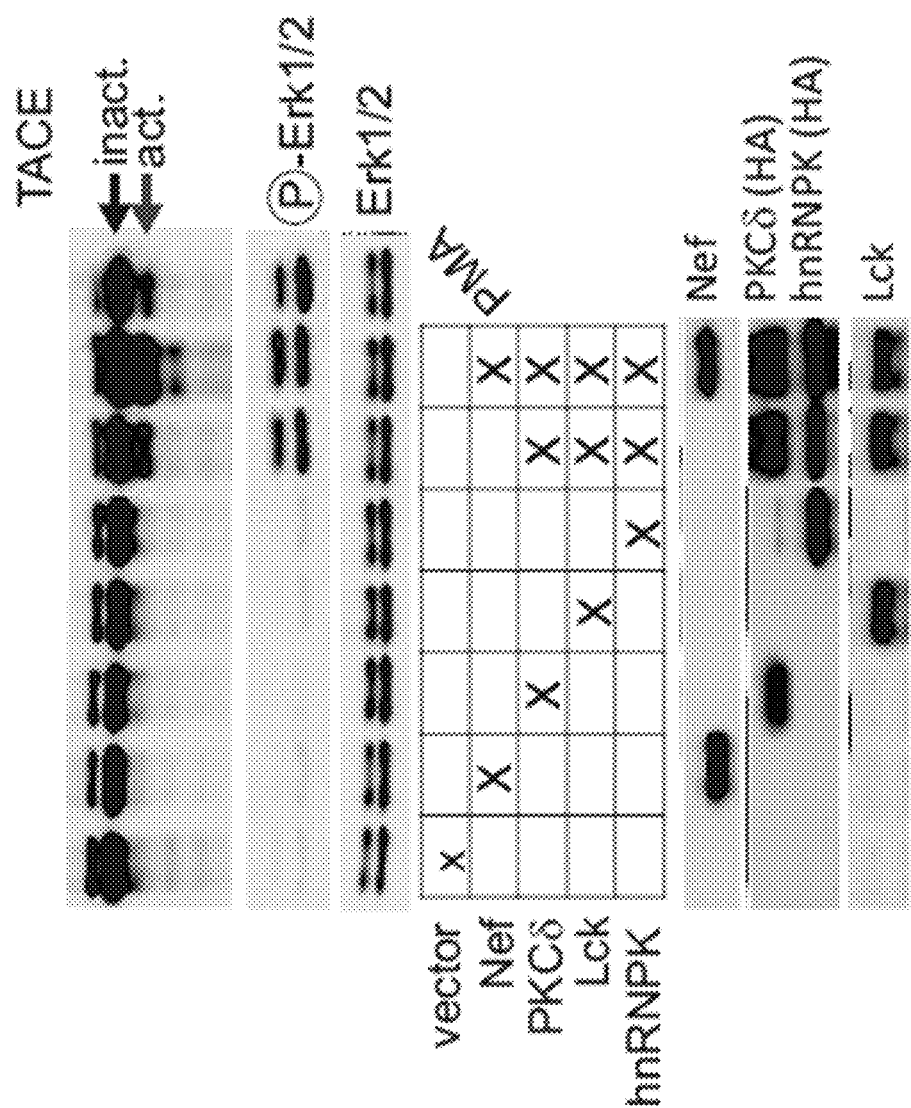

This result suggested that Nef/mNAKC not only shuttled TACE into EV, but activated the protease. For confirmation the previous experiment was repeated and cell lysates were blotted for TACE and its presumed activating kinase Erk1/2. Indeed, the Nef/mNAKC combination activated Erk1/2 and TACE to levels comparable to PMA, an established TACE activator (FIG. 1C; controls in FIG. 16A). For further confirmation we wanted to dissect the mechanism leading to TACE activation.

Paxillin and Eed Link NAKC to TACE

Figure 3A:
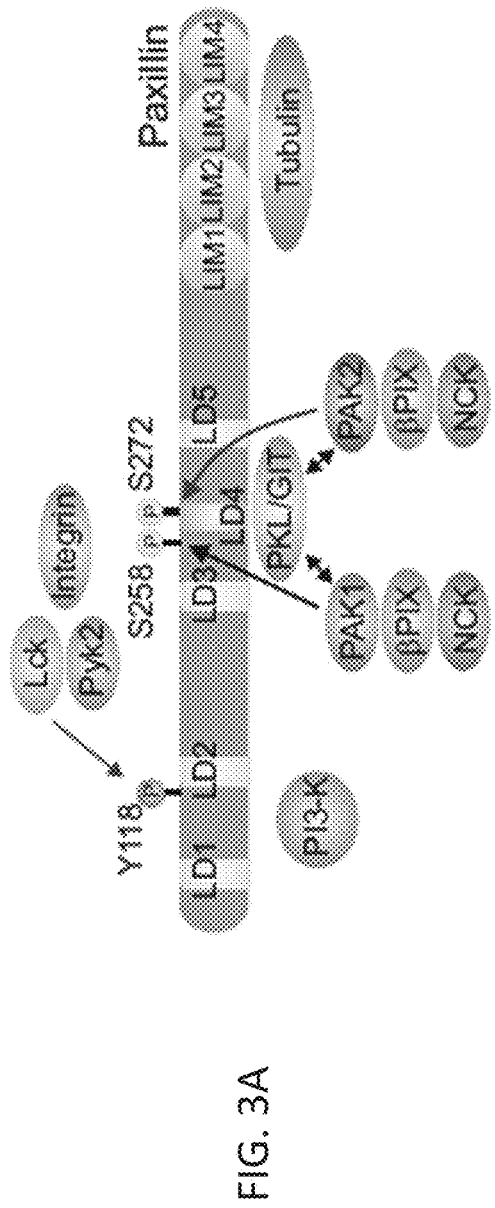
FIGS. 3A-3C: Pak1 and Pak2 regulate transfer of TACE and paxillin into lipid rafts.

Paxillin is an adaptor protein that is important for integrin signaling (Turner, 2000), shares many binding partners with Nef, including Pak2, PI-3 Kinase, Dock180-Elmo and Lck (FIG. 3A), and serves as a scaffold for Erk1/2 (Ostergaard et al., 1998; Ishibe et al., 2004). Furthermore paxillin was found to interact with hnRNPK (de Hoog et al., 2004), a factor in NAKC (FIGS. 1A and 15A). Therefore, we considered paxillin a protein that could connect Nef/NAKC with TACE.

Figure 16B:
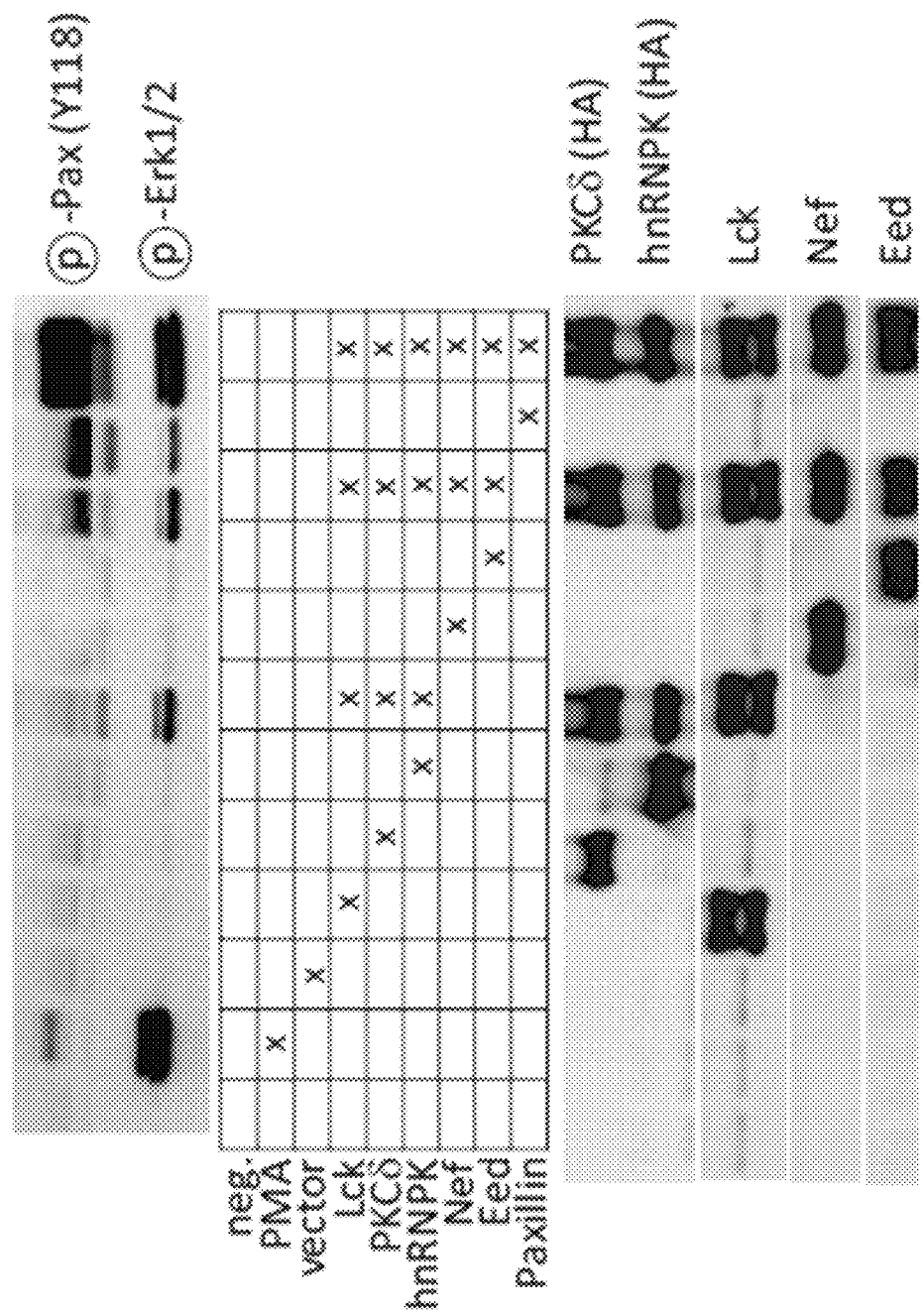
Figures 16C, 16D:
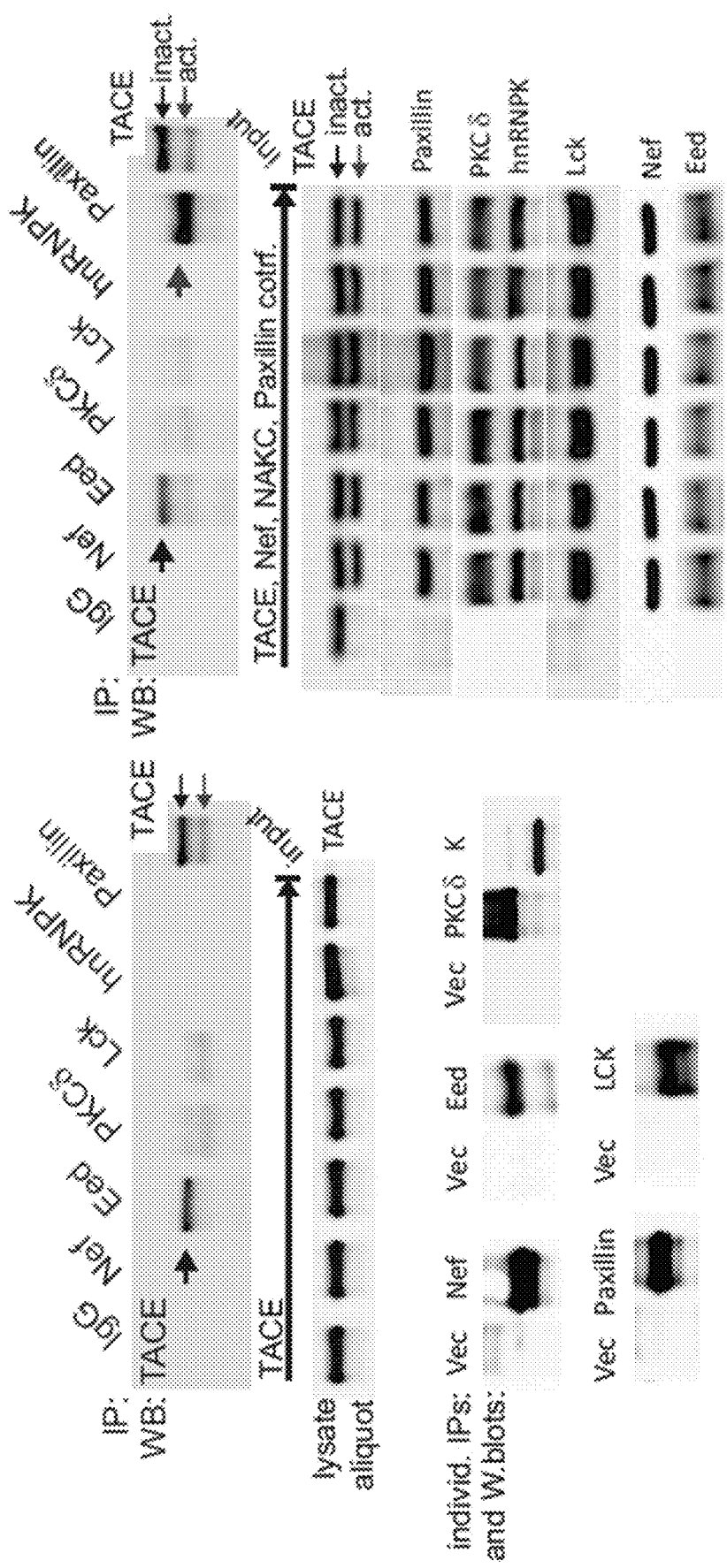

To test this idea we coexpressed paxillin with all NAKC proteins and Nef and examined Erk1/2 activation and paxillin phosphorylation using phospho-specific antibodies. Indeed, coexpression of all proteins activated Erk1/2 and dramatically increased paxillin phosphorylation at Y118, a consensus Src-family phosphorylation site (FIG. 1D, red arrows; controls in FIG. 16B). This implicated paxillin as a functional component of the Nef/NAKC protein network.

Figures 16E, 16F:
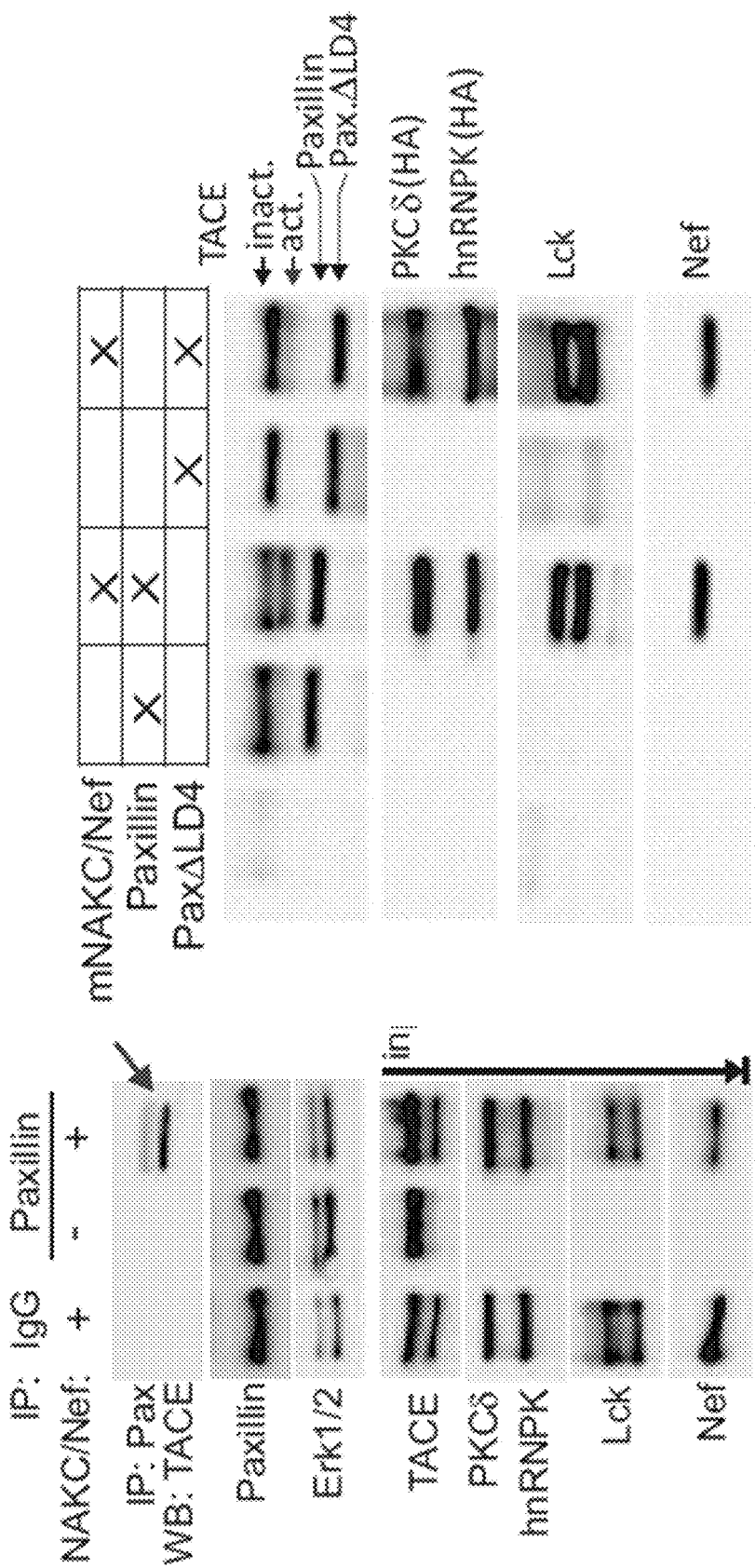

In order to establish a molecular link between NAKC and TACE (FIG. 1A) we performed individual coimmunoprecipitations with all NAKC components. To our surprise, we found that the polycomb protein Eed interacted with the inactive TACE precursor (135 kD) (FIG. 1E, upper panel, black arrow; controls in FIG. 16C). When all NAKC components were coexpressed, the now processed and active protease (95 kD) strongly bound paxillin (1E, lower panel, red double arrow; controls in FIG. 16D), while Eed still recruited the inactive precursor (black arrow). Likewise, immunoprecipitation of endogenous paxillin revealed binding predominantly of the active form of TACE (FIG. 16E, red arrow).

To explore the significance of paxillin in this process, we expressed a paxillin mutant with a deletion of the LD4 protein domain (FIG. 3A) (Tumbarello et al., 2002). Remarkably, in cells transfected with this mutant no paxillin-TACE coimmunoprecipitation or proteolytic activation of TACE by the Nef/mNAKC complex was observed (FIG. 1F, black double arrows; controls FIG. 16F). Furthermore, the LD4-mutant completely abrogated secretion of TACE via EV (FIG. 1F, red double arrow). Confocal analysis further supported these findings (FIG. 1G), revealing that TACE colocalized with native paxillin (red arrow) but not with paxillinΔLD4. Thus paxillin seemed a key factor in activation and secretion of TACE.

Pak2 and Pak1 Regluate Paxillin-TACE Association and Secretion

Figures 2A, 2B, 2C:
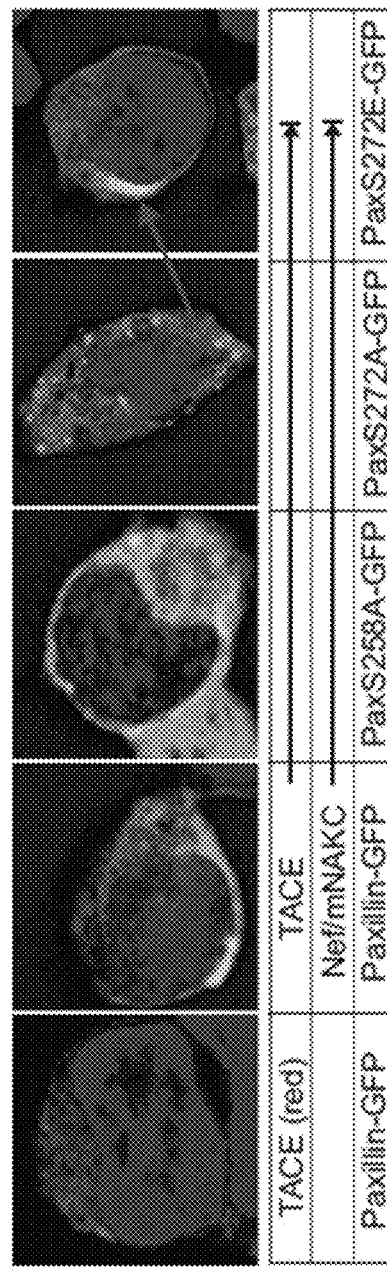
FIGS. 2A-2E: Pak2 and Pak1 regulate the association of paxillin with TACE.

Paxillin LD4 is a conserved binding domain that recruits the GIT1/β-PIX/Pak protein complex (FIG. 3A), facilitating cell migration and adhesion turnover (Tumbarello et al., 2002). The latter involves phosphorylation of paxillin by Pak kinase(s) at serine residues S258 and S272/274 (Nayal et al., 2006; Dong et al., 2009) and phosphorylation of Y118 by a Src kinase, presumably Lck (Ostergaard et al., 1998). To analyze paxillin phosphorylation and TACE recruitment, we abolished the Pak and Src phosphorylation sites (mutants S272/274A, S258A, Y118A) and mimicked S272/274 phosphorylation (mutant S272/274E). As shown in FIG. 2A (controls in FIG. 17A), paxillin mutations Y118A and S272/274A, individually, and especially in combination, greatly reduced or abrogated TACE binding, whereas S258A had no effect. By contrast, the phosphorylation-mimicking S272/274E mutant did not interfere with TACE binding. Confocal analysis supported these conclusions. The S272/274A mutant disrupted but the S272/274E mutant supported colocalization of paxillin and TACE (FIG. 2B, red double arrow). Taken together, phosphorylation of S272/274 and Y118 enabled TACE binding to paxillin.

Phosphorylation of S272/274 was shown to occur by a Pak-family kinase, but seemingly not by Pak1 (Dong et al., 2009), while Nef associated only with Pak2 (Renkema et al., 2001). To identify the Pak kinase(s) phosphorylating paxillin, constitutive active Pak1 or -2 (Pak1L107F, Pak2L106F) and trans-dominant negative Pak1 or -2 (Pak1R, Pak2R) mutants were analyzed for their influence on paxillin-TACE association. We found that active Pak2 increased the Nef/mNAKC-induced paxillin-TACE association, whereas active Pak1 inhibited this interaction (FIG. 2C, red double arrows; controls in FIG. 17B). Conversely, the inhibitory Pak2R reduced paxillin-TACE binding, whereas Pak1R promoted it (black double arrows).

Figure 2D:
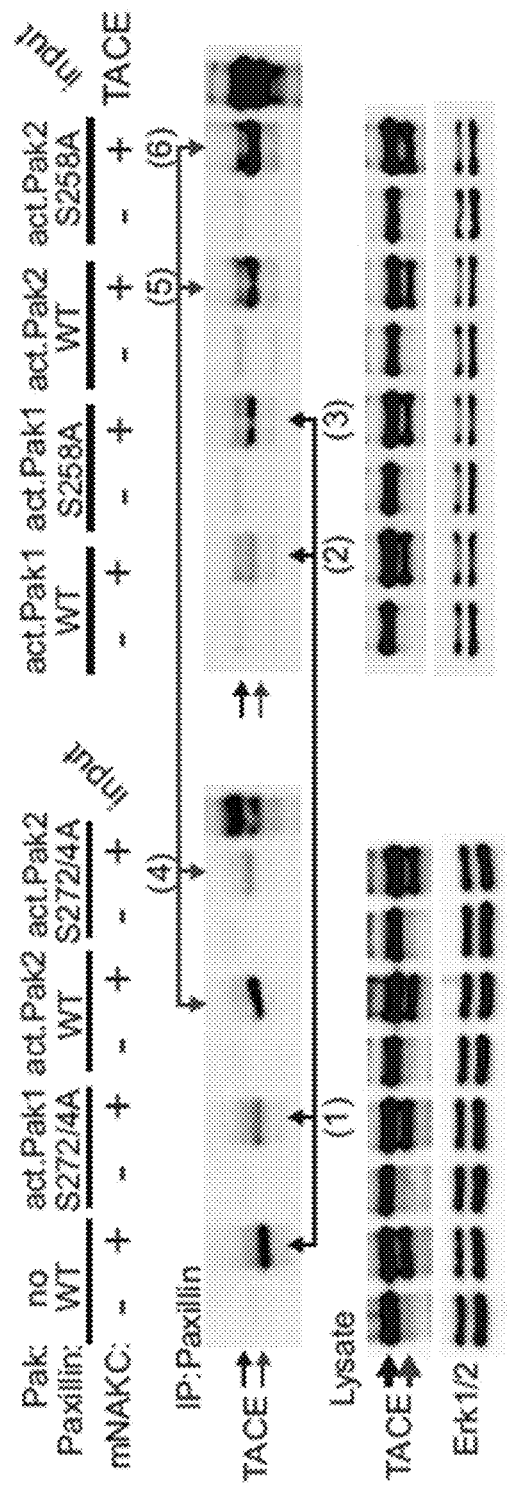

To further explore the seemingly opposing roles of Pak1 and Pak2, paxillin phosphorylation mutants were coexpressed with Nef/mNAKC and constitutive active Pak2 and Pak1, again scoring for TACE-paxillin association. As shown in FIG. 2D (controls in FIG. 18A), active Pak1 inhibited TACE association with paxillin-S272/274A (1) and wildtype paxillin (2) but not with paxillin S258A (3). Conversely, active Pak2 did not increase TACE association with paxillin-272/274A (4), but did so with wildtype paxillin (5) and paxillin S258A (6). Thus, binding of TACE to paxillin was negatively regulated by Pak1 via S258 and positively regulated by Pak2 via S272/274 phosphorylation.

Figure 2E:
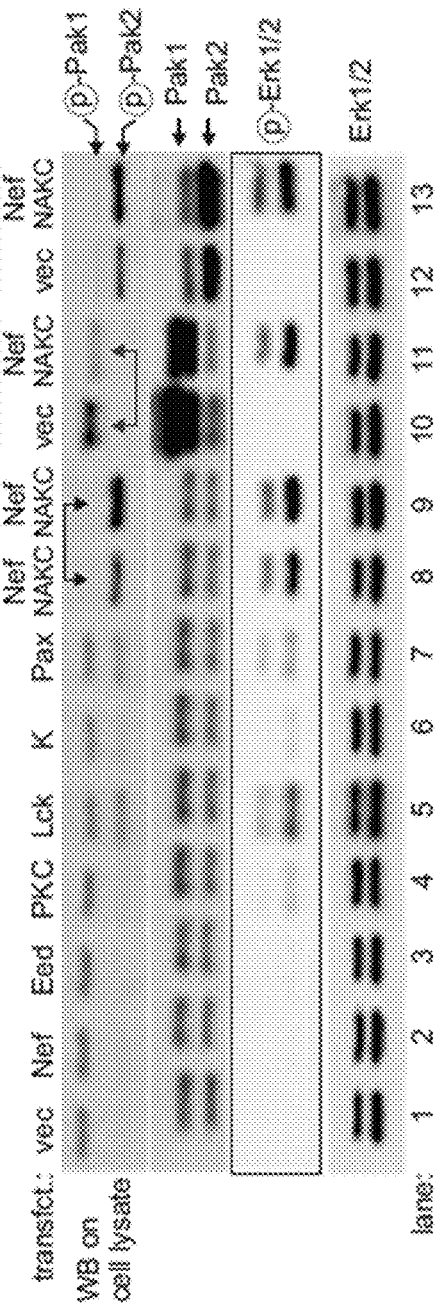

Nef is known to activate Pak2 (Renkema et al., 2001). Nevertheless we asked whether Nef/NAKC would modulate Pak1 activity. Upon expression of single NAKC factors, Pak1 seemed to be active whereas Pak2 was mostly inactive as judged by the use of a phospho-specific anti-Pak1/2 antibody (FIG. 2E, lane 1-7; controls in FIG. 18B). When Nef/NAKC was expressed, Pak2 was activated as expected and, interestingly, Pak1 turned inactive (lane 8). Notably, Pak2 activity increased when paxillin was added (black double arrow). Even the activity of constitutive active Pak1 strongly decreased when Nef/NAKC was coexpressed (FIG. 2E, red double arrow). Conversely, the activity of constitutive active Pak2 increased (lanes 12, 13). Thus the Nef signaling complex modulated the activity of both Pak kinase in an opposing manner.

Figure 3B:
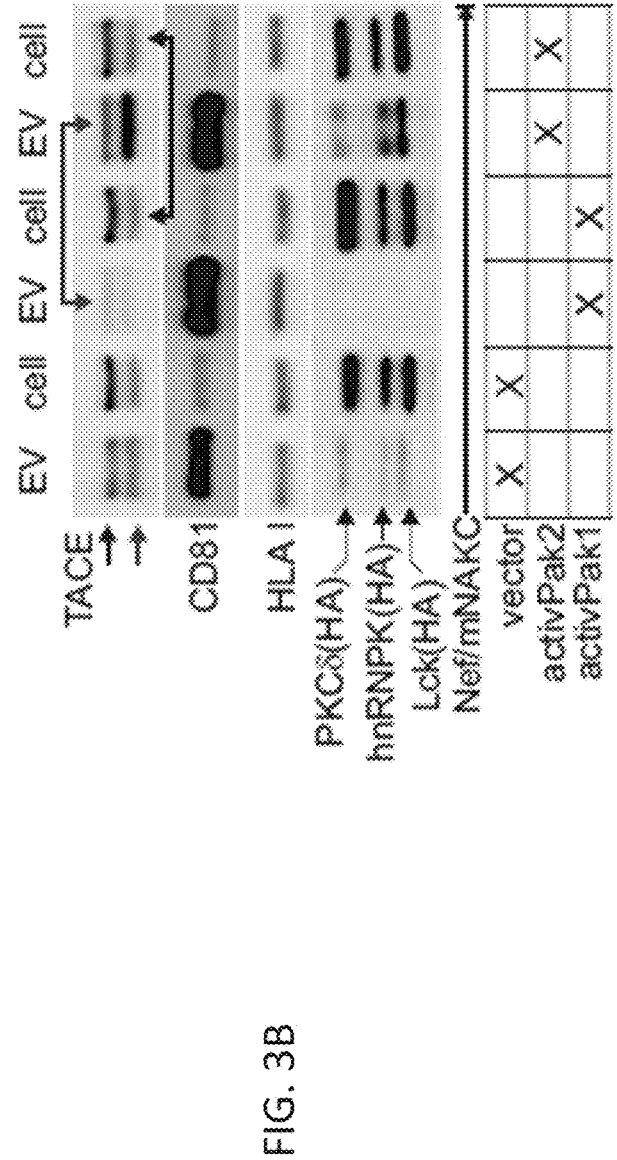

As expected, the Pak kinases influenced TACE uptake by EV. Whereas active Pak2 greatly increased TACE levels in EV, active Pak1 inhibited this process almost completely (FIG. 3B, red double arrow). Conversely, Pak1 and Pak2 had no influence on the amount of activated TACE in cell lysates (black double arrow).

Pak2 Phosphorylation of Paxillin Shuttles TACE into Lipid Rafts

Figure 3C:
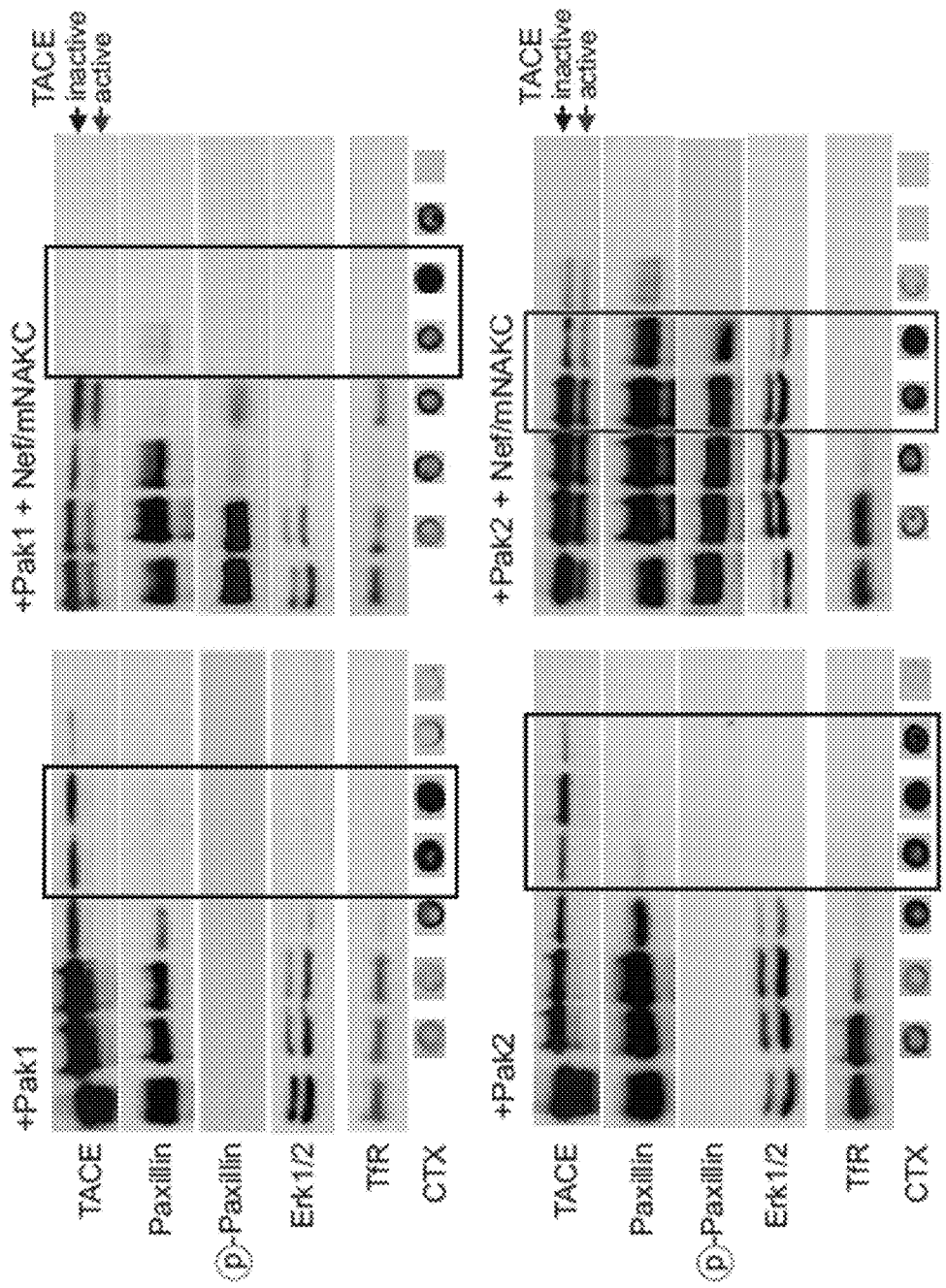

Previously a membrane transport pathway was identified that sorted proteins into exosomes depending on lipid raft-based micodomains and ceramide (Trajkovic et al., 2008). To analyze whether the Pak kinases regulated TACE secretion via lipid rafts, subcellular fractions were analyzed after transient transfection of paxillin, Pak1/2 and Nef/mNAKC into 293T cells. In the absence of Nef/mNAKC, inactive TACE was present in lipid rafts and expression of Pak1 or Pak2 made no difference (FIG. 3C, left panels). Upon coexpression of Nef/mNAKC, TACE was activated independently of Pak1 or Pak2 expression (right panels). In the presence of Pak2, however, activated TACE, (phospho)-paxillin and Erk1/2 were significantly enriched in lipid rafts (red quadrangle), whereas Pak1 excluded all proteins, including inactive TACE (FIG. 3C, right upper panel). Thus Pak1 and Pak2 regulated the shuttling of TACE into rafts, but were not involved in the activation of the protease (see also FIG. 3B).

Melanoma Cells Upload ADAM10 into EV by the Same Mechanism as HIV-1 Nef

Since cancer-derived EV were shown to contain TACE and/or ADAM10, we asked whether cancer cells activated the same signaling complex as Nef. We first assessed expression of TACE and ADAM10, the presence of phosphorylated paxillin (Y118), phosphorylated Erk1/2 and activated Pak1 and Pak2 in primary melanocytes and in 31 melanoma cell lines. In contrast to melanocytes, melanoma cells contained phosphorylated Erk1/2 (21/31; 68%), phosphorylated paxillin (27/31; 87%), phosphorylated Pak2 (21/31; 68%) and active ADAM10 (30/31; 97%) (FIGS. 4A and 19A). As judged by the anti-phopho-Pak antibody, Pak1 seemed less active than Pak2, at least in cytoplasmic lysates. TACE was only expressed at low levels. All cell lines secreted EV at varying levels, which contained predominantly active ADAM10 (FIG. 4B and data not shown). Notably, all EV also contained paxillin (FIG. 4B), similar to Nef/mNAKC-induced EV (FIG. 15B).

Next we asked whether paxillin would bind to ADAM10 similar as seen with TACE and if Pak1/2 would modulate this interaction. Paxillin was immunoprecipitated from two melanoma cell lines (FIG. 4C; ML1 and 3) and analyzed for ADAM10 binding. In both lines paxillin bound predominantly the active form of ADAM10 (FIG. 4C, first lane, red arrows, controls in FIG. 19B). In addition, the Pak1 and -2 mutants were transfected into both cell lines, and paxillin-ADAM10 association was analyzed. The results were identical as seen in FIG. 2 with TACE. Active Pak2 and inhibitory Pak1R increased paxillin-ADAM10 association (FIG. 4C, double red arrows), whereas active Pak1 and inhibitory Pak2R prevented this interaction (double black arrows).

Figures 4C, 4D:
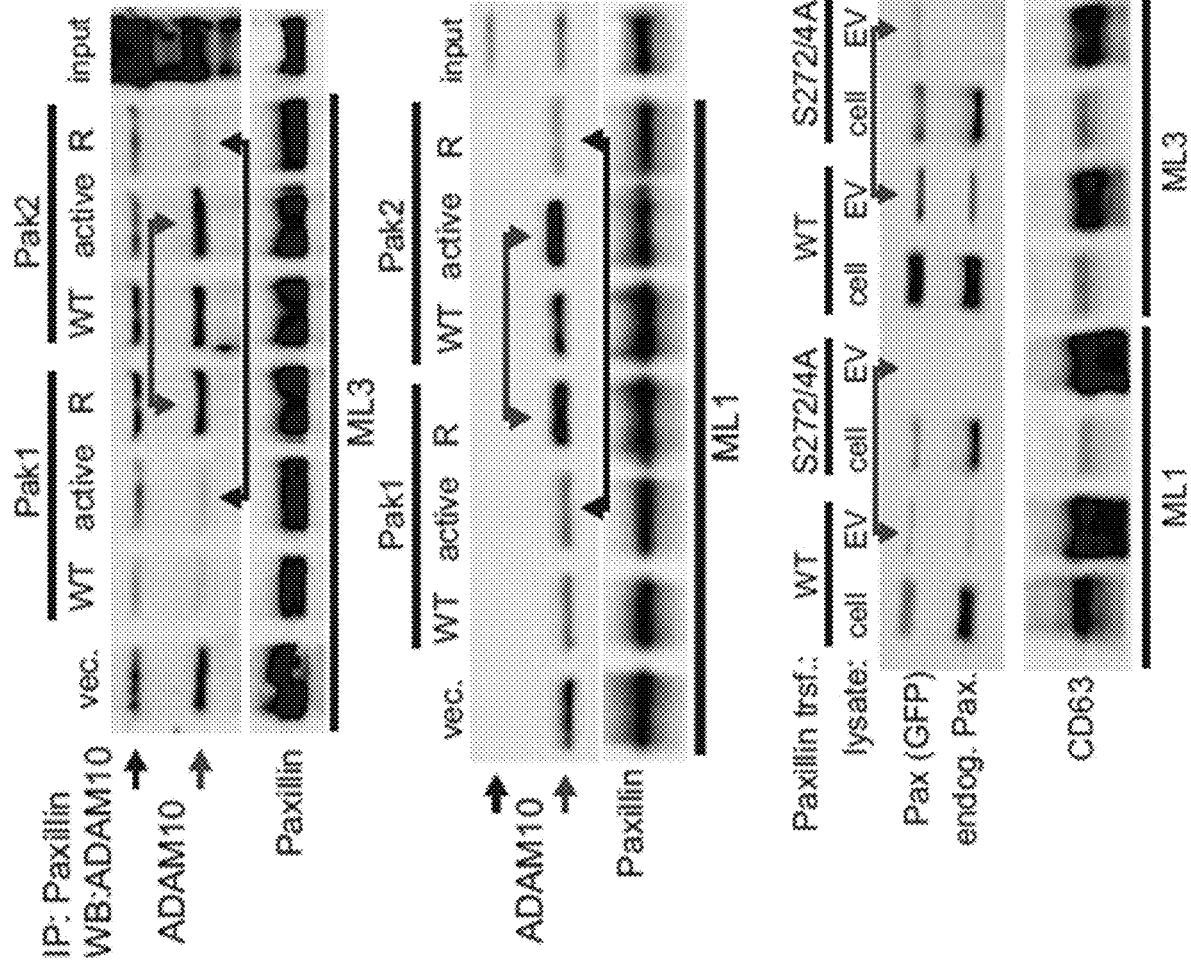

For further confirmation, the paxillin 5272/4A mutant was transfected into the same melanoma lines and secreted EV were analyzed for the presence of paxillin. As expected, paxillin was reduced in EV lysates of both cell lines (FIG. 4D). Surprisingly this also included endogenous wt paxillin, possibly because the transfected mutant was squelching limiting factors. Taken together, uploading of ADAM10 into melanoma EV occurred by the same mechanism as in Nef-expressing cells.

Nef-Activated TACE Cleaves proTNFα in Endosomal Compartments

While TACE seemed to be activated by Nef/mNAKC, it was not clear whether and where the protease was functionally active. To address this question, we developed a convenient assay. We constructed a GFP-proTNF-RFP fusion protein (G-proTNF-R; FIG. 5A), expecting that the full-length protein would give a yellow signal, which upon TACE-mediated cleavage would mature into prodomain-associated green (GFP) and TNFα-associated red (RFP) fluorescence. Furthermore, we reasoned the construct might reveal the subcellular compartments where proTNFα was cleaved.

In 293T cells the transfected G-proTNF-R construct gave a double positive (GFP/RFP) signal in FACS and a yellow staining in confocal images (FIGS. 5B and E). Upon coexpression of Nef/mNAKC and TACE, this signal decreased by approximately 40%, indicating that the fusion protein was cleaved (FIG. 5B; summary and controls in FIG. 5C). Increased cleavage was also demonstrated by immunoblotting (FIG. 5D; controls in FIG. 20A). In addition, we measured an increased activity of endogenous TACE in Nef/mNAKC transfected 293T cells using a commercial, substrate-based activity assay (FIG. 20B). In all experiments the effect was reversed upon exposure of cultured cells to TAPI, confirming the ADAM-dependence of this process.

Figure 5E:
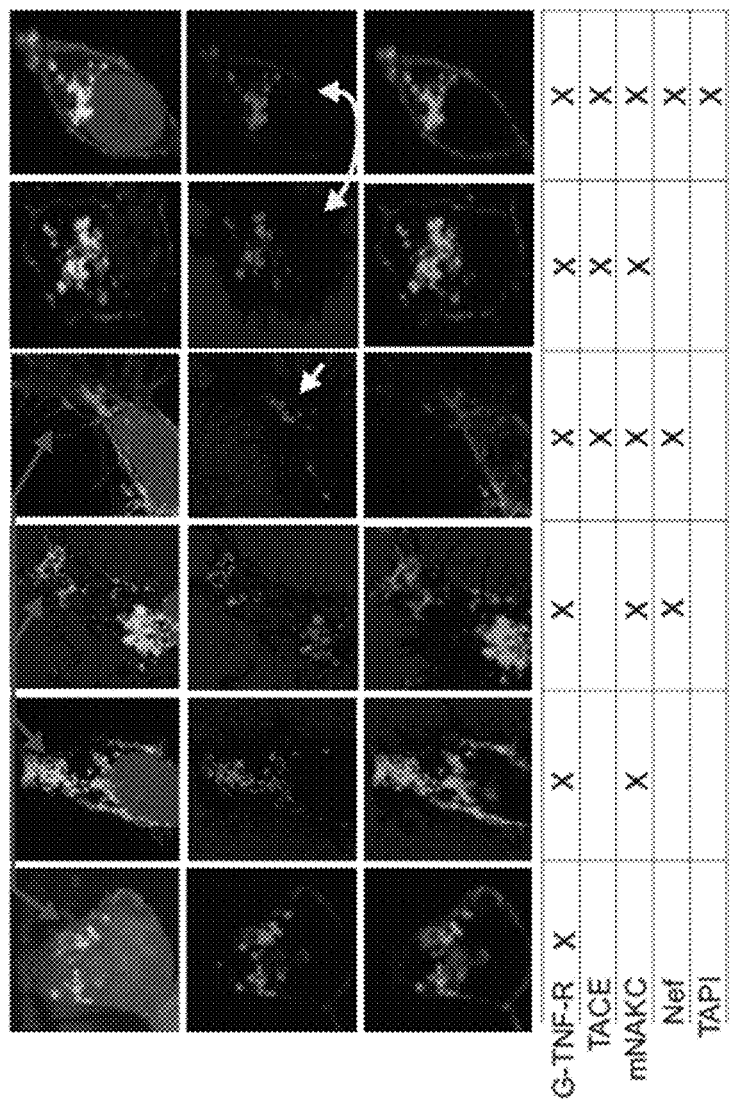
Figure 5F:
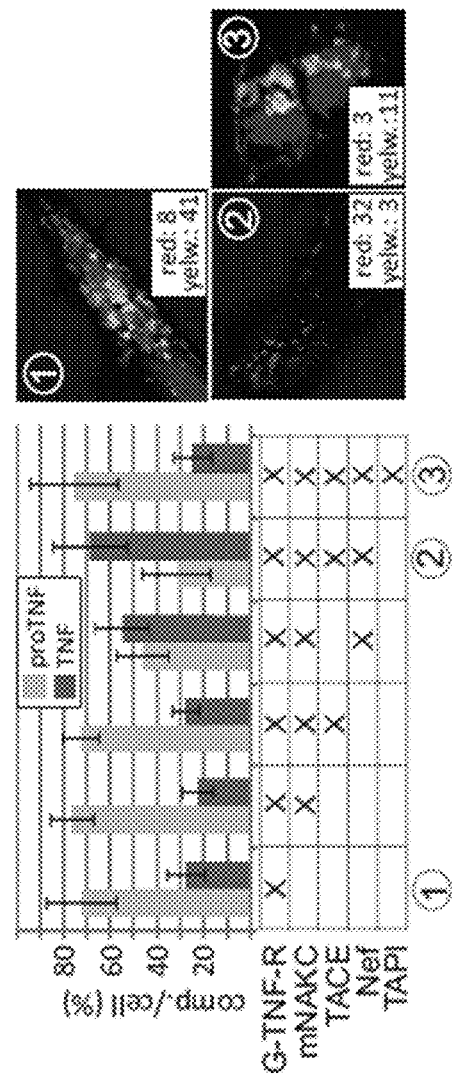

Confocal analysis revealed a successive separation of yellow endosomes into green (GFP) and red (RFP) vesicular compartments and membranes (FIG. 5E, compare red arrows, detailed in FIG. 21), until mainly red-fluorescent compartments remained when Nef, mNAKC and TACE were coexpressed (white arrow). These images also revealed that proTNFα was not only cleaved at the plasma membrane (FIG. 5E, yellow arrow) but to a larger extent in intracellular compartments, similar as suggested before (Solomon et al., 1997). To quantify this process, yellow and red endosomal compartments were counted for each condition in 20 randomly selected cells on a single confocal level (examples in FIG. 5F). The results confirmed that Nef and TACE cooperatively induced and enhanced G-proTNF-R endosomal cleavage (FIG. 5F). In addition, these results revealed the requirement of Nef for this process since mNAKC alone had no effect.

Figure 5G:
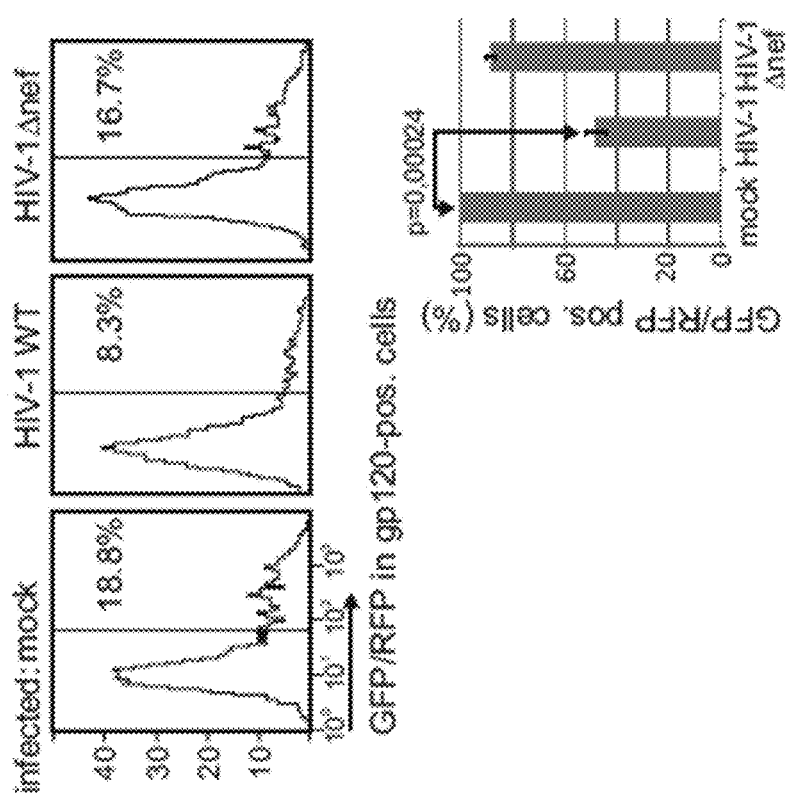

The G-proTNF-R construct enabled us to test Nef-mediated TACE activation in HIV-infected cells. HeLaCD4 cells were first transfected with G-proTNF-R and, 12 hours later, infected with HIV-1 (pNL4-3) or a nef-deleted isotype (pNL4-3Δnef). To increase infection efficiency, viral particles were pseudotyped with VSV-G. On day 3, cells were analyzed for the GFP/RFP signal in productively infected cells (appearance of gp120). As shown in FIG. 5G, only in cells producing wt HIV-1 a significant reduction of unprocessed G-proTNF-R (GFP/RFP signal) was observed (approximately 56%, see bar diagram). This confirmed that proTNFα cleavage occurred in infected cells and was Nef-dependent. A similar result was obtained when 293T cells were transfected with the HIV-1 proviral DNA and a nef-deleted isogenic version (FIG. 20C).

TACE-Uploaded EV Cleave proTNFα

Figure 6A:
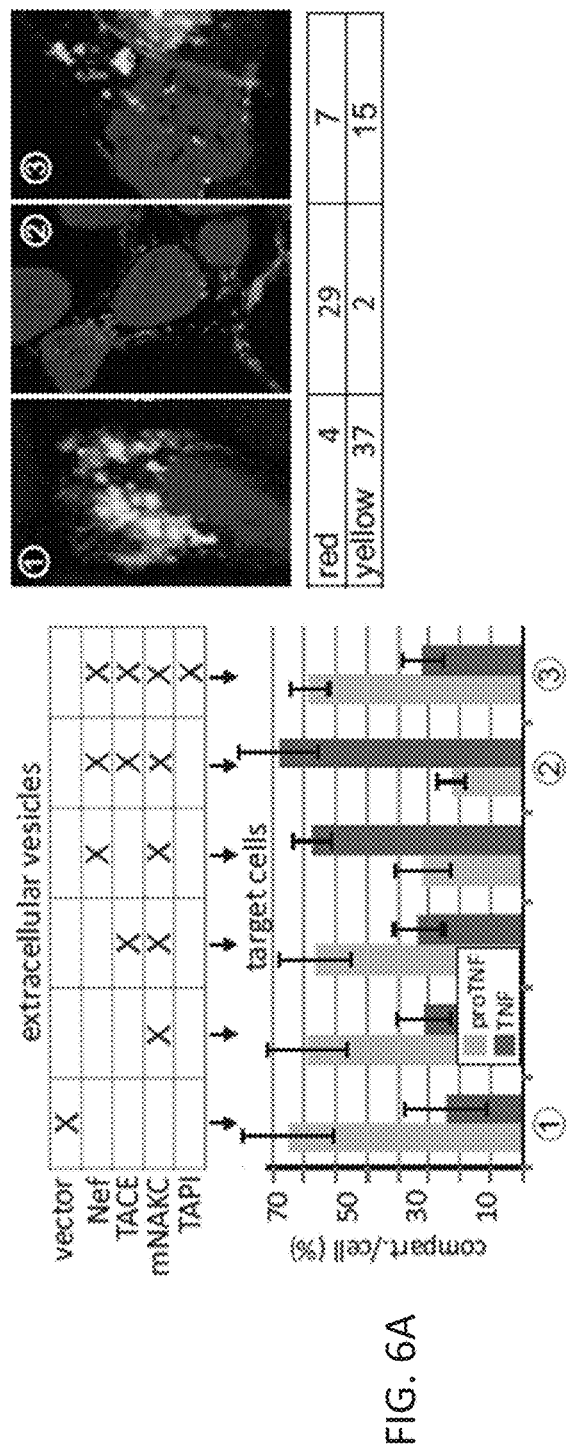
FIG. 6A-6E: Nef/NAKC-induced EV induce proTNFα cleavage.

Using the G-proTNF-R construct we were also able to analyze the function of TACE/ADAM10-loaded EV. A number of reports had demonstrated that EV induce the secretion of cytokines in recipient cells (Atay et al., 2011; Qazi et al., 2010). Therefore we reasoned that TACE-containing EV might cleave proTNFα. EV were prepared from transfected cells as indicated (FIG. 6A) and incubated with target 293T cells containing G-proTNF-R. Subsequently we assessed yellow and red vesicular compartments (examples in bottom of FIG. 6A). The results were similar as in FIG. 5F revealing increased intracellular processing of G-proTNF-R predominantly with EV derived from Nef/mNAKC/TACE-transfected cells (FIG. 6A, bar diagram). These results implied that TACE-uploaded EV reached the perinuclear region and fused with G-proTNF-R containing compartments, similar to what was recently demonstrated for breast cancer tumor vesicles (Koumangoye et al., 2011).

Figure 6B:
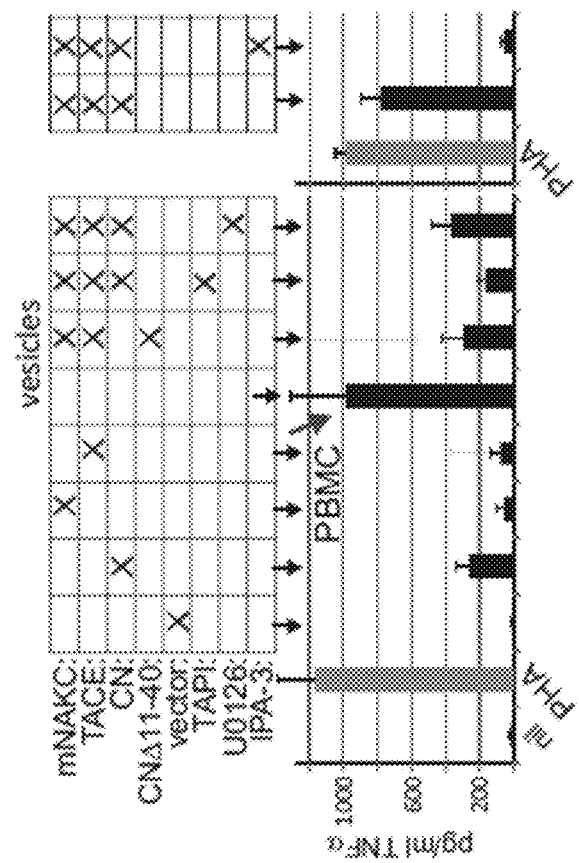
Figure 6D:
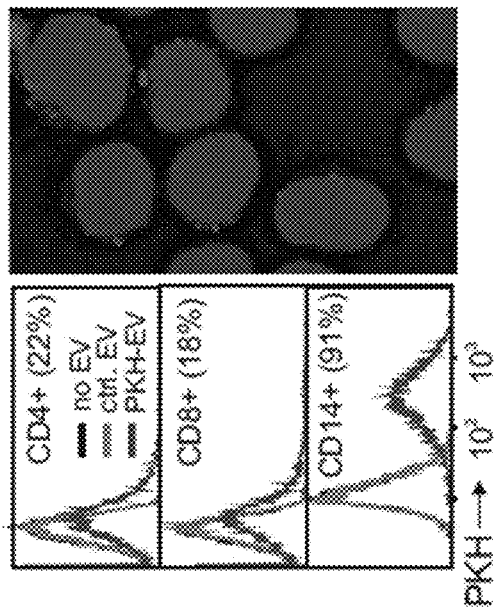
Figure 6C:
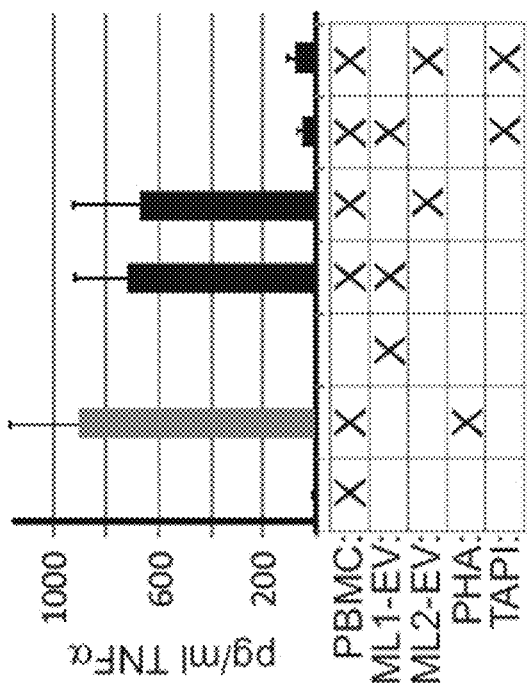

For confirmation we incubated EV with resting PBMC (6 hours) and measured TNFα release. EV derived from 293T cells expressing mNAKC, TACE and a CD8-Nef fusionprotein (CN) had the most potent capacity to stimulate TNFα release (FIG. 6B, red arrow). A comparable TNFα release was seen when PBMC were stimulated with PHA (5 μg/ml). Conversely, expression of TACE alone or in concert with an N-terminal deletion mutant of Nef (CNΔ11-40) that does not assemble NAKC (Wolf et al., 2008), yielded EV with a greatly reduced TNFα cleavage capacity. TNFα release was also significantly reduced when EV-producing cells were incubated with the ADAM inhibitor TAPI or the inhibitor of the TACE-activating kinase Erk1/2 (U0126) or a Pak kinase inhibitor (IPA-3) (FIG. 6B). EV purified from supernatants of two primary melanoma cell lines also induced TNFα release in an ADAM-dependent manner (FIG. 6C). When PKH-labeled EV were incubated (2 hours) with resting PBMC, mainly monocytes (CD14+ cells, 91%) but also lymphocytes picked up the red labeled vesicles (FIG. 6D), similar as demonstrated by others (Tian et al., 2010). Together these data suggested that TACE/ADAM10-up-loaded EV had the capacity to stimulate TNFα release from target cells.

Plasma from HIV and Melanoma Patients Harbors ADAM-Containing EV

Figure 6E:
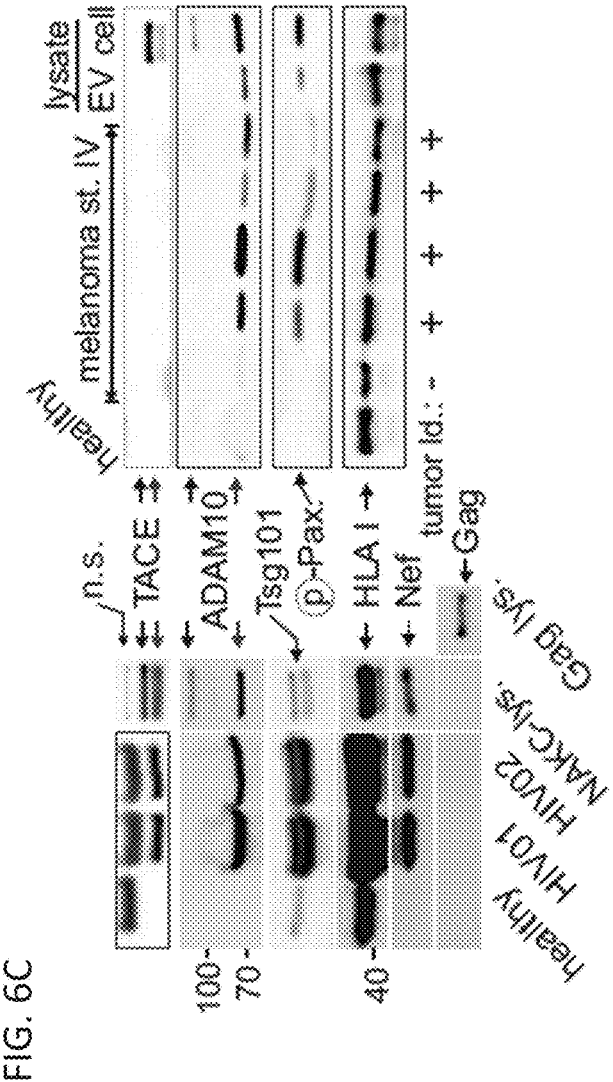

To extend these data into an in-vivo context we analyzed EV purified from plasma of 2 HIV-1-infected individuals and 5 stage IV melanoma patients w/wo tumor load. Lysates (50 μg) of these EV (yield from ~4 ml plasma) were analyzed by immunoblot. In contrast to a non-infected control, plasma from HIV-1 patients (HIV01, HIV02) harbored high concentrations of EV as judged by the strong signals for Tsg101 and HLA class I (FIG. 6E, left panels). As anticipated, these vesicles contained activated TACE and, interestingly, also activated ADAM10. Importantly, the EV also harbored Nef, but no viral capsid protein p24 (FIG. 6E, left panels), excluding the presence of viral particles. EV from melanoma patients revealed a different phenotype containing predominantly ADAM10, similar as seen in vitro (see FIG. 4B) (FIG. 6E right panels). Also, and similar to in vitro produced EV (FIG. 16B), plasma EV contained phosphorylated paxillin (FIG. 6E, right panels). Taken together these results confirmed our in vitro findings and revealed a surprisingly high concentration of EV with activated ADAM proteases in plasma from HIV-1 as well as melanoma patients.

SUMMARY

In this report we describe how the Nef signaling complex interacts with the integrin-associated adaptor protein paxillin, leading to the activation and secretion of ADAM proteases through extracellular vesicles. The mechanism is activated in two very different diseases and hence may be of particular relevance. Presumably its molecular function serves to stimulate cytokine release and/or the shedding of activating ligands creating a favorable microenvironment for pathogens and cancer cells.

From our data it appears likely that the Nef signaling complex contains all the crucial factors to activate TACE/ADAM10 (summary in FIGS. 7A-7C). Within the Nef complex paxillin may have a key role, as the large adaptor protein connects to ADAM-interacting integrins and to proteins of the Nef signaling complex, including hnRNPK, Lck, Erk1/2, and Pak (Ostergaard et al., 1998; Ishibe et al., 2004; Deakin and Turner, 2008). Supporting this assumption the paxillin LD4 domain was essential for TACE activation. Furthermore, Pak kinases and paxillin form a regulatory circuit in Nef/NAKC-transfected as well as in melanoma tumor cells. Taken all facts together, paxillin stands out as a likely orchestrator or signaling hub for the activation of TACE and ADAM10.

Unexpectedly, the polycomb group protein Eed associated with the inactive TACE precursor. As Eed is also a direct interactor of Nef and integrins (Witte et al., 2004; Rietzler et al., 1998), its translocation to the membrane could be the first step in TACE/ADAM10 activation. This conclusion allows some speculation about the molecular role of Eed. We suggested that Eed recruitment derepresses the HIV-1 promoter (Wolf et al., 2008; Witte et al., 2004) and the same may be true for the TNFα promoter as reported previously (Jacob et al., 2011). This would fit well with a cofunction of Eed to activate TACE and could also explain its role in nSMase2 activation after TNFR1 stimulation. In this scenario TACE activation, TNFα secretion and TNFR1 stimulation are coupled events to initiate an autocrine stimulation loop. Downstream nSMase2 facilitates the generation of EV, explaining increased vesicle formation through Nef or integrin activation. Taken together, Eed may have a multifaceted role in TNFα activation and secretion.

Coexpression of three NAKC proteins (PKCδ, hnRNPK, Lck) was sufficient to activate Erk1/2 and TACE, raising the question about the role of Nef in this process. First, Nef clearly enhanced TACE activation, likely by recruiting factors to the membrane. Second, Nef was essential for the efficient cleavage of G-proTNF-R. We would speculate that Nef's well documented ability to modulate the endocytosis machinery (Baur, 2011) serves to bring activated TACE efficiently to endosomal compartments containing proTNFα. This function may also be required to steer vesicles to the perinuclear region once they are ingested by target cells.

Increased TNFα processing after HIV infection suggests that infected cells start their own TNFα production. This would stimulate the viral microenvironment and HIV-1 transcription in an auto-as well as paracrine fashion. This could explain the particular relevance of Nef for viral replication and its early expression even before viral integration (Wu and Marsh, 2001). In the lymphatic tissue microenvironment with small intercellular spaces this mechanism could rapidly build up stimulating TNFα concentrations. In fact, ex vivo tissue models show a particularly strong effect of Nef on HIV-1 replication and spread (Glushakova et al., 1999). This mechanism may also explain the high plasma levels of ADAM substrates (e.g. TNFα receptor, TNFα) in infected individuals (Graziosi et al., 1996; Zangerle et al., 1994). Because of its obvious impact on viral replication we assume that the activation of TACE is the main function of Nef.

Support for this conclusion comes from our finding that Pak2 is involved in this mechanism. The role of Pak2 in Nef function has been an enigma ever since the interaction was reported (Sawai et al., 1994; Renkema et al., 1999; Van den Broeke et al., 2010). Notably, most substrates of Pak2 are linked to paxillin, including beta-PIX and Merlin. Merlin associates with paxillin (Fernandez-Valle et al., 2002) and is phosphorylated at serine 518 after expression of Nef (Wei et al., 2005). Intrestingly, activated (i.e. phosphorylated) Merlin inhibits Pak1 (Kissil et al., 2003), thus linking Merlin directly to the here described Pak1/Pak2/paxillin regulatory circuit. In fact, Nef/NAKC strongly inhibited Pak1 activity. Taken together, Nef-mediated activation of Pak2 leads to the phosphorylation of paxillin at S272/274 and Merlin at S518. Since both events promote paxillin-TACE association, this reveals the surprising role of Pak2, namely to secrete activated TACE via EV.

In view of the large number of substrates of ADAM proteases, the uncontrolled release of ADAM-containing EV could be detrimental for host organisms, potentially contributing to some of the common clinical features seen in HIV-1 infection and cancer, including weight loss, wasting and immunodeficiency. Although still speculative, support for this assumption comes from our finding that plasma of cancer and HIV-1-infected patients contains surprisingly high levels of TACE/ADAM10 loaded vesicles. If their potentially detrimental role is confirmed, interference with these vesicles could open an unexpected avenue of treatment in both, HIV-1 infection and cancer.

REFERENCE LIST

Arduise, C., Abache, T., Li, L., Billard, M., Chabanon, A., Ludwig, A., Mauduit, P., Boucheix, C., Rubinstein, E., and Le, N. F. (2008). Tetraspanins regulate ADAM10-mediated cleavage of TNF-alpha and epidermal growth factor. J. Immunol. 181, 7002-7013.

Atay, S., Gercel-Taylor, C., and Taylor, D. D. (2011). Human trophoblast-derived exosomal fibronectin induces pro-inflammatory IL-1beta production by macrophages. Am. J. Reprod. Immunol. 66, 259-269.

Baur, A. S. (2011). HIV-Nef and AIDS pathogenesis: are we barking up the wrong tree? Trends Microbiol. 19, 435-440.

Baur, A. S., Sass, G., Laffert, B., Willbold, D., Cheng-Mayer, C., and Peterlin, B. M. (1997). The N-terminus of Nef from HIV-1/SIV associates with a protein complex containing Lck and a serine kinase. Immunity. 6, 283-291.

Blobel, C. P. (2005). ADAMs: key components in EGFR signalling and development. Nat. Rev. Mol. Cell Biol. 6, 32-43.

Caswell, P. T., Vadrevu, S., and Norman, J. C. (2009). Integrins: masters and slaves of endocytic transport. Nat. Rev. Mol. Cell Biol. 10, 843-853.

de Hoog, C. L., Foster, L. J., and Mann, M. (2004). RNA and RNA binding proteins participate in early stages of cell spreading through spreading initiation centers. Cell 117, 649-662.

Deacon, N. J., Tsykin, A., Solomon, A., Smith, K., Ludford-Menting, M., Hooker, D. J., McPhee, D. A., Greenway, A. L., Ellett, A., Chatfield, C., Lawson, V. A., Crowe, S., Maerz, A., Sonza, S., Learmont, J., Sullivan, J. S., Cunningham, A., Dwyer, D., Dowton, D., and Mills, J. (1995). Genomic structure of an attenuated quasi species of HIV-1 from a blood transfusion donor and recipients. Science 270, 988-991.

Deakin, N. O. and Turner, C. E. (2008). Paxillin comes of age. J. Cell Sci. 121, 2435-2444. Diaz-Rodriguez, E., Montero, J. C., Esparis-Ogando, A., Yuste, L., and Pandiella, A. (2002). Extracellular signal-regulated kinase phosphorylates tumor necrosis factor alpha-converting enzyme at threonine 735: a potential role in regulated shedding. Mol. Biol. Cell 13, 2031-2044.

Dong, J. M., Lau, L. S., Ng, Y. W., Lim, L., and Manser, E. (2009). Paxillin nuclear-cytoplasmic localization is regulated by phosphorylation of the LD4 motif: evidence that nuclear paxillin promotes cell proliferation. Biochem. J. 418, 173-184.

Fernandez-Valle, C., Tang, Y., Ricard, J., Rodenas-Ruano, A., Taylor, A., Hackler, E., Biggerstaff, J., and Iacovelli, J. (2002). Paxillin binds schwannomin and regulates its density-dependent localization and effect on cell morphology. Nat. Genet. 31, 354-362.

Glushakova, S., Grivel, J. C., Suryanarayana, K., Meylan, P., Lifson, J. D., Desrosiers, R., and Margolis, L. (1999). Nef enhances human immunodeficiency virus replication and responsiveness to interleukin-2 in human lymphoid tissue ex vivo. J. Virol. 73, 3968-3974.

Graziosi, C., Gantt, K. R., Vaccarezza, M., Demarest, J. F., Daucher, M., Saag, M. S., Shaw, G. M., Quinn, T. C., Cohen, O. J., Welbon, C. C., Pantaleo, G., and Fauci, A. S. (1996). Kinetics of cytokine expression during primary human immunodeficiency virus type 1 infection. Proc. Natl. Acad. Sci. U.S.A 93, 4386-4391.

Higginbotham, J. N., Demory, B. M., Gephart, J. D., Franklin, J. L., Bogatcheva, G., Kremers, G. J., Piston, D. W., Ayers, G. D., McConnell, R. E., Tyska, M. J., and Coffey, R. J. (2011). Amphiregulin exosomes increase cancer cell invasion. Curr. Biol. 21, 779-786.

Ishibe, S., Joly, D., Liu, Z. X., and Cantley, L. G. (2004). Paxillin serves as an ERK-regulated scaffold for coordinating FAK and Rac activation in epithelial morphogenesis. Mol. Cell 16, 257-267.

Jacob, E., Hod-Dvorai, R., Ben-Mordechai, O. L., Boyko, Y., and Avni, O. (2011). Dual function of polycomb group proteins in differentiated murine T helper (CD4+) cells. J. Mol. Signal. 6, 5.

Kestler, H. W., Ill, Ringler, D. J., Mori, K., Panicali, D. L., Sehgal, P. K., Daniel, M. D., and Desrosiers, R. C. (1991). Importance of the nef gene for maintenance of high virus loads and for development of AIDS. Cell 65, 651-662.

Kissil, J. L., Wilker, E. W., Johnson, K. C., Eckman, M. S., Yaffe, M. B., and Jacks, T. (2003). Merlin, the product of the Nf2 tumor suppressor gene, is an inhibitor of the p21-activated kinase, Pak1. Mol. Cell 12, 841-849.

Koumangoye, R. B., Sakwe, A. M., Goodwin, J. S., Patel, T., and Ochieng, J. (2011). Detachment of breast tumor cells induces rapid secretion of exosomes which subsequently mediate cellular adhesion and spreading. PLoS. One. 6, e24234.

Le Gall, S. M., Bobe, P., Reiss, K., Horiuchi, K., Niu, X. D., Lundell, D., Gibb, D. R., Conrad, D., Saftig, P., and Blobel, C. P. (2009). ADAMs 10 and 17 represent differentially regulated components of a general shedding machinery for membrane proteins such as transforming growth factor alpha, L-selectin, and tumor necrosis factor alpha. Mol. Biol. Cell 20, 1785-1794.

Lenassi, M., Cagney, G., Liao, M., Vaupotic, T., Bartholomeeusen, K., Cheng, Y., Krogan, N. J., Plemenitas, A., and Peterlin, B. M. (2010). HIV Nef is secreted in exosomes and triggers apoptosis in bystander CD4+ T cells. Traffic. 11, 110-122.

Manninen, A., Hiipakka, M., Vihinen, M., Lu, W., Mayer, B. J., and Saksela, K. (1998). SH3-Domain binding function of HIV-1 Nef is required for association with a PAK-related kinase. Virology 250, 273-282.

Moss, M. L., Sklair-Tavron, L., and Nudelman, R. (2008). Drug insight: tumor necrosis factor-converting enzyme as a pharmaceutical target for rheumatoid arthritis. Nat. Clin. Pract. Rheumatol. 4, 300-309.

Muratori, C., Cavallin, L. E., Kratzel, K., Tinari, A., De, M. A., Fais, S., D'Aloja, P., Federico, M., Vullo, V., Fomina, A., Mesri, E. A., Superti, F., and Baur, A. S. (2009). Massive secretion by T cells is caused by HIV Nef in infected cells and by Nef transfer to bystander cells. Cell Host. Microbe 6, 218-230.

Murphy, G. (2008). The ADAMs: signalling scissors in the tumour microenvironment. Nat. Rev. Cancer 8, 929-941.

Nayal, A., Webb, D. J., Brown, C. M., Schaefer, E. M., Vicente-Manzanares, M., and Horwitz, A. R. (2006). Paxillin phosphorylation at Ser273 localizes a GIT1-PIX-PAK complex and regulates adhesion and protrusion dynamics. J. Cell Biol. 173, 587-589.

Ostergaard, H. L., Lou, O., Arendt, C. W., and Berg, N. N. (1998). Paxillin phosphorylation and association with Lck and Pyk2 in anti-CD3- or anti-CD45-stimulated T cells. J. Biol. Chem. 273, 5692-5696.

Philipp, S., Puchert, M., Adam-Klages, S., Tchikov, V., Winoto-Morbach, S., Mathieu, S., Deerberg, A., Kolker, L., Marchesini, N., Kabelitz, D., Hannun, Y. A., Schutze, S., and Adam, D. (2010). The Polycomb group protein EED couples TNF receptor 1 to neutral sphingomyelinase. Proc. Natl. Acad. Sci. U.S.A 107, 1112-1117.

Qazi, K. R., Torregrosa, P. P., Dahlberg, B., Grunewald, J., Eklund, A., and Gabrielsson, S. (2010). Proinflammatory exosomes in bronchoalveolar lavage fluid of patients with sarcoidosis. Thorax 65, 1016-1024.

Raymond, A. D., Campbell-Sims, T. C., Khan, M., Lang, M., Huang, M. B., Bond, V. C., and Powell, M. D. (2010). HIV Type 1 Nef Is Released from Infected Cells in CD45(+) Microvesicles and Is Present in the Plasma of HIV-Infected Individuals. AIDS Res. Hum. Retroviruses.

Renkema, G. H., Manninen, A., Mann, D. A., Harris, M., and Saksela, K. (1999). Identification of the Nef-associated kinase as p21-activated kinase 2. Curr. Biol. 9, 1407-1410.

Renkema, G. H., Manninen, A., and Saksela, K. (2001). Human immunodeficiency virus type 1 Nef selectively associates with a catalytically active subpopulation of p21-activated kinase 2 (PAK2) independently of PAK2 binding to Nck or beta-PIX. J. Virol. 75, 2154-2160.

Rietzler, M., Bittner, M., Kolanus, W., Schuster, A., and Holzmann, B. (1998). The human WD repeat protein WAIT-1 specifically interacts with the cytoplasmic tails of beta7-integrins. J. Biol. Chem. 273, 27459-27466.

Sawai, E. T., Baur, A., Struble, H., Peterlin, B. M., Levy, J. A., and Cheng-Mayer, C. (1994). Human immunodeficiency virus type 1 Nef associates with a cellular serine kinase in T lymphocytes. Proc. Natl. Acad. Sci. U.S.A 91, 1539-1543.

Schiavoni, l., Trapp, S., Santarcangelo, A. C., Piacentini, V., Pugliese, K., Baur, A., and Federico, M. (2004). HIV-1 Nef enhances both membrane expression and virion incorporation of Env products. A model for the Nef-dependent increase of HIV-1 infectivity. J. Biol. Chem. 279, 22996-23006.

Skog, J., Wurdinger, T., van, R. S., Meijer, D. H., Gainche, L., Sena-Esteves, M., Curry, W. T., Jr., Carter, B. S., Krichevsky, A. M., and Breakefield, X. O. (2008). Glioblastoma microvesicles transport RNA and proteins that promote tumour growth and provide diagnostic biomarkers. Nat. Cell Biol. 10, 1470-1476.

Solomon, K. A., Covington, M. B., DeCicco, C. P., and Newton, R. C. (1997). The fate of pro-TNF-alpha following inhibition of metalloprotease-dependent processing to soluble TNF-alpha in human monocytes. J. Immunol. 159, 4524-4531.

Stoeck, A., Keller, S., Riedle, S., Sanderson, M. P., Runz, S., Le, N. F., Gutwein, P., Ludwig, A., Rubinstein, E., and Altevogt, P. (2006). A role for exosomes in the constitutive and stimulus-induced ectodomain cleavage of L1 and CD44. Biochem. J. 393, 609-618.

Thery, C., Amigorena, S., Raposo, G., and Clayton, A. (2006). Isolation and characterization of exosomes from cell culture supernatants and biological fluids. Curr. Protoc. Cell Biol. Chapter 3, Unit.

Tian, T., Wang, Y., Wang, H., Zhu, Z., and Xiao, Z. (2010). Visualizing of the cellular uptake and intracellular trafficking of exosomes by live-cell microscopy. J. Cell Biochem. 111, 488-496.

Trajkovic, K., Hsu, C., Chiantia, S., Rajendran, L., Wenzel, D., Wieland, F., Schwille, P., Brugger, B., and Simons, M. (2008). Ceramide triggers budding of exosome vesicles into multivesicular endosomes. Science 319, 1244-1247.

Tumbarello, D. A., Brown, M. C., and Turner, C. E. (2002). The paxillin LD motifs. FEBS Lett. 513, 114-118.

Turner, C. E. (2000). Paxillin and focal adhesion signalling. Nat. Cell Biol. 2, E231-E236. Turner, C. E., Brown, M. C., Perrotta, J. A., Riedy, M. C., Nikolopoulos, S. N., McDonald, A. R., Bagrodia, S., Thomas, S., and Leventhal, P. S. (1999). Paxillin LD4 motif binds PAK and PIX through a novel 95-kD ankyrin repeat, ARF-GAP protein: A role in cytoskeletal remodeling. J. Cell Biol. 145, 851-863.

Van den Broeke, C., Radu, M., Chernoff, J., and Favoreel, H. W. (2010). An emerging role for p21-activated kinases (Paks) in viral infections. Trends Cell Biol. 20, 160-169.

Wei, B. L., Arora, V. K., Raney, A., Kuo, L. S., Xiao, G. H., O'Neill, E., Testa, J. R., Foster, J. L., and Garcia, J. V. (2005). Activation of p21-activated kinase 2 by human immunodeficiency virus type 1 Nef induces merlin phosphorylation. J. Virol. 79, 14976-14980.

Witte, V., Laffert, B., Rosorius, O., Lischka, P., Blume, K., Galler, G., Stilper, A., Willbold, D., D'Aloja, P., Sixt, M., Kolanus, J., Ott, M., Kolanus, W., Schuler, G., and Baur, A. S. (2004). HIV-1 Nef mimics an integrin receptor signal that recruits the polycomb group protein Eed to the plasma membrane. Mol. Cell 13, 179-190.

Wolf, D., Giese, S.l., Witte, V., Krautkramer, E., Trapp, S., Sass, G., Haller, C., Blume, K., Fackler, O. T., and Baur, A. S. (2008a). Novel (n)PKC kinases phosphorylate Nef for increased HIV transcription, replication and perinuclear targeting. Virology 370, 45-54.

Wolf, D., Witte, V., Clark, P., Blume, K., Lichtenheld, M. G., and Baur, A. S. (2008). HIV Nef enhances Tat-mediated viral transcription through a hnRNP-K-nucleated signaling complex. Cell Host. Microbe 4, 398-408.

Wolf, D., Witte, V., Laffert, B., Blume, K., Stromer, E., Trapp, S., D'Aloja, P., Schurmann, A., and Baur, A. S. (2001). HIV-1 Nef associated PAK and PI3-kinases stimulate Akt-independent Bad-phosphorylation to induce anti-apoptotic signals. Nat. Med. 7, 1217-1224.

Wu, Y. and Marsh, J. W. (2001). Selective transcription and modulation of resting T cell activity by preintegrated HIV DNA. Science 293, 1503-1506.

Zangerle, R., Gallati, H., Sarcletti, M., Weiss, G., Denz, H., Wachter, H., and Fuchs, D. (1994). Increased serum concentrations of soluble tumor necrosis factor receptors in HIV-infected individuals are associated with immune activation. J. Acquir. Immune. Defic. Syndr. 7, 79-85.

The invention claimed is:

1. A method for in vitro detecting physiological enzymatic activity of a protease, wherein the protease is ADAM17, in protease-containing extracellular vesicles (EV), the method comprising:

providing a modified peptide by combining a protease-sensitive peptide comprising 5 or more amino acids with (a) a fluorophore modification and a quencher modification, wherein the fluorophore modification is lipophilic, conferring membrane translocation potential to the peptide, or (b) an N- and/or C-terminal sequence comprising 5-20 membrane-penetrating amino acids with a fluorophore modification and a quencher modification, wherein the modified peptide comprises a protease-specific cleavage site located between the fluorophore modification and the quencher modification; and detecting physiological enzymatic activity of the protease in enriched and/or purified protease-containing EV from a plasma sample using the modified peptide, wherein the enriched and/or purified EV are EV enriched and/or purified by performing an enrichment and/or purification method comprising an antibody-based method or use of a sucrose gradient or exosome isolation reagent, and wherein said EV comprise EV that do not express CD81.

2. The method of claim 1, wherein the enriched and/or purified EV are EV that have further been treated via a centrifugation method.

\* \* \* \* \*